(12) United States Patent
Vann

(10) Patent No.: US 6,573,089 B1
(45) Date of Patent: Jun. 3, 2003

(54) METHOD FOR USING AND MAKING A FIBER ARRAY

(75) Inventor: Charles S. Vann, Burlingame, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/705,647

(22) Filed: Nov. 2, 2000

Related U.S. Application Data

(60) Division of application No. 09/590,761, filed on Jun. 8, 2000, which is a division of application No. 09/479,181, filed on Jan. 7, 2000, which is a continuation-in-part of application No. 09/227,799, filed on Jan. 8, 1999, now abandoned.

(51) Int. Cl.[7] .......................... C12M 1/34; C12Q 1/68; C12P 19/34; G01N 33/00; C07H 21/02
(52) U.S. Cl. ...................... 435/287.2; 435/6; 435/91.1; 435/287.1; 436/94; 536/23.1
(58) Field of Search ............... 435/6, 91.1, 91.2, 435/283, 283.1, 285.2, 287.1, 287.2; 436/94, 501; 536/23.1, 24.3, 24.33, 25.3; 422/50, 55, 68.1, 82.05, 82.07, 82.08, 82.09, 82.12

(56) References Cited

U.S. PATENT DOCUMENTS

| | | | |
|---|---|---|---|
| 4,447,546 A | 5/1984 | Hirschfeld | |
| 4,503,012 A | 3/1985 | Starr | |
| 4,668,636 A | 5/1987 | Ringrose et al. | |
| 4,682,710 A | 7/1987 | Turner, Jr. et al. | |

(List continued on next page.)

FOREIGN PATENT DOCUMENTS

| | | |
|---|---|---|
| DE | 4419586 | 12/1995 |
| EP | 633 465 A1 | 1/1995 |
| WO | WO 93/21513 | 10/1993 |
| WO | WO 94/12863 | 6/1994 |

(List continued on next page.)

OTHER PUBLICATIONS

Girvitz et al., A rapid and efficient procedure for the purification of DNA from agarose gel. Anal. Biochem. 106, 492–496, 1980.*
Weiler et al., Combining the preparation of oligonucleotide arrays and synthesis of high-quality primers. Anal. Biochem. 243, 218–227, 1996.*
Webster's II New Riverside University Dictionary, pp. 733 and 803.*
Piunno et al., Fiber-optic DNA sensor for fluorometric nucleic acid determination. Anal. Chem. 67, 2635–2643, 1995.*
Michael et al., "Randomly Ordered Addressable High-Density Optical Sensor Arrays"; *Analytical Chemistry* vol. 70, No. 7; Apr. 1, 1998; pp. 1242–1248.
Herne et al.; "Characterization of DNA Probes Immobilized on Gold Surfaces"; *J. Am. Chem. Soc.* vol. 119; Jun. 13, 1997; pp. 8916–8920.

(List continued on next page.)

*Primary Examiner*—Ethan C. Whisenant
*Assistant Examiner*—Frank Lu
(74) *Attorney, Agent, or Firm*—Pennie & Edmonds LLP

(57) ABSTRACT

An apparatus and method are provided for contacting at least two chemical species, comprising a support plate having a channel for receiving a mobile chemical species and a fiber, having a second chemical species immobilized thereon, disposed on the support plate. At least a portion of the fiber is exposed to the channel such that the mobile chemical species is capable of contacting the second chemical species. An apparatus and method for reading the fiber array, an apparatus and method for making the fiber array, and methods of using the fiber array of the present invention are also provided.

17 Claims, 40 Drawing Sheets

U.S. PATENT DOCUMENTS

| | | |
|---|---|---|
| 4,691,850 A | 9/1987 | Kirschmann et al. |
| 4,810,658 A | 3/1989 | Shanks et al. |
| 4,822,746 A | 4/1989 | Walt |
| 4,974,927 A | 12/1990 | Kimura |
| 5,114,864 A | 5/1992 | Walt |
| 5,143,853 A | 9/1992 | Walt |
| 5,192,510 A | 3/1993 | Zoha et al. |
| 5,202,231 A | 4/1993 | Drmanac et al. |
| 5,219,726 A | 6/1993 | Evans |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,320,808 A | 6/1994 | Holen et al. |
| 5,320,814 A | 6/1994 | Walt et al. |
| 5,341,962 A | 8/1994 | Way et al. |
| 5,429,807 A | 7/1995 | Matson et al. |
| 5,512,490 A | 4/1996 | Walt et al. |
| 5,525,464 A | 6/1996 | Drmanac et al. |
| 5,530,779 A | 6/1996 | Baldini et al. |
| 5,532,129 A | 7/1996 | Heller |
| 5,565,322 A | 10/1996 | Heller |
| 5,585,069 A | 12/1996 | Zanzucchi et al. |
| 5,599,695 A * | 2/1997 | Pease et al. ............... 435/91.1 |
| 5,605,662 A | 2/1997 | Heller et al. |
| 5,632,957 A | 5/1997 | Heller et al. |
| 5,633,972 A | 5/1997 | Walt et al. |
| 5,661,028 A | 8/1997 | Foote |
| 5,675,151 A | 10/1997 | Oka et al. |
| 5,677,195 A | 10/1997 | Winkler et al. |
| 5,700,897 A | 12/1997 | Klainer et al. |
| 5,744,305 A | 4/1998 | Fodor et al. |
| 5,787,032 A | 7/1998 | Heller et al. |
| 5,807,522 A | 9/1998 | Brown et al. |
| 5,814,524 A | 9/1998 | Walt et al. |
| 5,843,651 A | 12/1998 | Stimpson et al. |
| 5,863,502 A * | 1/1999 | Southgate et al. ............ 422/58 |
| 6,023,540 A | 2/2000 | Walt et al. |
| 6,060,288 A | 5/2000 | Adams et al. |
| 6,078,705 A | 6/2000 | Neuschäfer et al. |
| 6,146,593 A | 11/2000 | Pinkel et al. |

FOREIGN PATENT DOCUMENTS

| | | |
|---|---|---|
| WO | WO 95/02566 | 1/1995 |
| WO | WO 96/17957 | 6/1996 |
| WO | WO 97/27324 | 7/1997 |
| WO | WO 98/15355 | 4/1998 |
| WO | WO 98/31836 | 7/1998 |
| WO | WO 98/40726 | 9/1998 |
| WO | WO 98/50782 | 11/1998 |
| WO | 98-53300 | 11/1998 |
| WO | 98/58079 | 12/1998 |
| WO | WO 99/18434 | 4/1999 |
| WO | WO 99/45357 | 9/1999 |
| WO | WO 99/67641 | 12/1999 |
| WO | WO 00/13004 | 3/2000 |
| WO | WO 00/16101 | 3/2000 |
| WO | WO 00/29832 | 5/2000 |
| WO | WO 00/39587 | 7/2000 |
| WO | WO 00/44491 | 8/2000 |
| WO | WO 00/47996 | 8/2000 |
| WO | WO 00/48000 | 8/2000 |
| WO | WO 00/63437 | 10/2000 |

OTHER PUBLICATIONS

Wang et al.; "Mismatch–Sensitive Hybridization Detection by Peptide Nucleic Acids Immobilized on a Quartz Crystal Microbalance"; *Anal. Chem.* vol. 69, No. 24; Dec. 15, 1997; pp. 5200–5202.

Ferguson, et al.; "A Fiber–Optic DNA Biosensor Microarray for the Analysis of Gene Expression"; *Nature Biotechnology* vol. 14; Dec. 1996; pp. 1681–1684.

Abel, et al.; "Fiber–Optic Evanescent Wave Biosensor for the Detection of Oligonucleotides"; *Analytical Chemistry* vol. 68, No. 17; Sep. 1, 1996; pp. 2905–2912.

Milanovich et al.; "Clinical Measurements Using Fiber Optics and Optrodes"; *SPIE, Novel Optical Fiber Techniques for Medical Applications*, vol. 494; Apr. 21, 1984; pp. 18–24.

Li et al.; "Dual–Analyte Fiber–Optic Sensor for the Simultaneous and Continuous Measurement of Glucose and Oxygen"; *Anal. Chem.*, vol. 67, No. 20.; Oct. 15, 1995; pp. 3746–3752.

Walt et al.; "Improved Fiber–Optic Chemical Sensor for Penicillin"; *Anal. Chem.*, vol. 67, No. 24; Dec. 15, 1995; pp. 4471–4476.

Dickinson et al.; "A Chemical–Detecting System Based on a Cross–Reactive Optical Sensor Array"; *Nature*, vol. 382; Aug. 22, 1996; pp. 697–700.

Ferguson et al.; "Simultaneous Monitoring of pH, $CO_2$ and $O_2$ Using an Optical Imaging Fiber", *Analytical Chimica Acta*, vol. 240; 1997; pp. 123–131.

Browne et al.; "Intrinsic Sol–Gel Clad Fiber–Optic Sensors with Time–Resolved Detection"; *Anal. Chem.*; vol. 68, No. 14; Jul. 15, 1996; pp. 2289–2295.

Freeman et al.; "Oxygen Probe Based on Tetrakis(alkylamino)ethylene Chemiluminescence"; *Anal. Chem.*; vol. 53, No. 1; Jan. 1981; pp. 98–102.

Wolfbeis et al.; "Fiber–Optic Fluoresensor for Oxygen and Carbon Dioxide"; *Anal. Chem.*; vol. 60, No. 19; Oct. 1, 1998; pp. 2028–2030.

Jordan et al.; "Physiological pH Fiber–Optic Chemical Sensor Based on Energy Transfer"; *Anal. Chem.*; vol. 59, No. 3; Feb. 1, 1987; pp. 437–439.

Lubbers et al.; "Optical Fluorescence Sensors for Continuous Measurement of Chemical Concentrations in Biological Systems"; *Sensors and Actuators*; vol. 4; 1983; pp. 641–654.

Munkholm et al.; "Polymer Modification of Fiber Optic Chemical Sensors as a Method of Enhancing Fluorescence Signal for pH Measurement"; *Anal. Chem.*; vol. 58, No. 7; Jun. 1986; pp. 1427–1430.

Seitz; "Chemical Sensors Based on Fiber Optics"; *Anal. Chem.*; vol. 56, No. 1; Jan. 1984; pp. 16A–34A.

Peterson et al.; "Fiber Optic pH Probe for Physiological Use"; *Anal. Chem.*; vol. 52, No. 6; May 1980; pp. 864–869.

Saari et al.; "pH Sensor Based on Immobilized Fluoresceinamine"; *Anal. Chem.*; vol. 54, No. 4; Apr. 1982; pp. 821–823.

Collison et al.; "Chemical Sensors for Bedside Monitoring of Critically Ill Patients"; *Anal. Chem.*; vol. 6, No. 7; Apr. 1, 1990; pp. 425–437.

Schwab et al.; "Versatile, Efficient Raman Sampling with Fiber Optics"; *Anal. Chem.*; vol. 56, No. 12; Oct. 1984; pp. 2199–2204.

Saarl et al.; "Immobilized Morin as Fluorescence Sensor for Determination of Aluminum (III)"; *Anal. Chem.*; vol. 55, No. 4; Apr. 1983; pp. 667–670.

Seitz; "Chemical Sensors Based on Immobilized Indicators and Fiber Optics"; *CRC Critical Review in Analytical Chemistry*; vol. 19, Issue 2; 1988; pp. 135–173.

Tan et al.; "Submicrometer Intracellular Chemical Optical Fiber Sensors"; *Science*; vol. 258; Oct. 30, 1992; pp. 778–781.

Janata; "Chemical Sensors"; *Anal. Chem.*; vol. 64, No. 12; Jun. 15, 1992; pp. 196R–219R.

Orellana et al.; Fiber–Optic Sensing of Carbon Dioxide Based on Excited–State Proton Transfer to a Luminescent Ruthenium (II) Complex; *Anal. Chem.*; vol. 64, No. 19; Oct. 1, 1992; pp. 2210–2215.

Michael et al.; "The Use of Optical–Imaging Fibers for the Fabrication of Array Sensors"; *American Chemical Society Symposium Series*, vol. 690, Ch. 23; pp. 273–289.

Peterson et al.; "Fiber–Optic Sensors for Biomedical Applications"; *Science*; vol. 224(4645); Apr. 13, 1984; pp. 123–127.

Fuh et al.; "Single Fibre Optic Fluorescence pH Probe"; *Analyst*; vol. 112; Aug. 1987; pp. 1159–1163.

Hirschfeld et al.; "Laser–Fiber–Optic "Optrode" for Real Time In Vivo Blood Carbon Dioxide Level Monitoring"; *Journal of Lightwave Technology*; vol. Lt–5, No. 7; Jul. 1987; pp. 1027–1033.

Barnard et al.; "A Fibre–Optic Chemical Sensor with Discrete Sensing Sites"; *Nature*; vol. 353; Sep. 26, 1991; pp. 338–340.

Mignani et al.; "In–Vivo Biomedical Monitoring by Fiber–Optic Systems"; *Journal of Lightwave Technology*; vol. 13, No. 7; Jul. 1995; pp. 1396–1406.

Healey et al.; "Fiberoptic DNA Sensor Array Capable of Detecting Point Mutations"; *Analytical Biochemistry*; vol. 251; 1997; pp. 270–279.

Graham et al.; "Gene Probe Assays on a Fibre–Optic Evanescent Wave Biosensor"; *Biosensors & Bioelectronics*; vol. 7; 1992; pp. 487–493.

Piunno et al.; "Fiber Optic Biosensor for Fluorimetric Detection of DNA Hybridization"; *Analytica Chimica Acta*; vol. 288; 1994; pp. 205–214.

Gordon et al.; "Optical Waveguide Device for DNA Hybridization Analysis"; *Oxford University Press*; vol. 30; 1996; pp. 164–168.

Stimpson et al.; "Real–time Detection of DNA Hybridization and Melting on Oligonucleotide Arrays by Using Optical Wave Guides"; *Proc. Natl. Acad. Sci.*; vol. 92; Jul. 1995; pp. 6379–6383.

Stimpson et al.; "The Utility of Optical Waveguide DNA Array Hybridization and Melting for Rapid Resolution of Mismatches, and for Detection of Minor Mutant Components in the Presence of a Majority of Wild Type Sequence: Statistical Model and Supporting Data"; *Genetic Analysis: Biomolecular Engineering*; vol. 13; 1996; pp. 73–80.

Smith, "Fiber Eases Single–Molecule Detection", *Photonics Spectra*, Feb. 2000, p. 23.

Fang and Tan, "Imaging Single Fluorescent Molecules at the Interface of an Optical Fiber Probe by Evanescent Wave Excitation", *Anal. Chem.*, vol. 71; 1999, pp. 3101–3105.

Abrams, "Fiber Optic Sensor Achieves High Sensitivity", *Biophotonics International*, p. 31 (1998).

Duveneck et al., "Fiber Optic Evanescent Wave Biosensor", *SPIE Chemical and Medical Sensors*, 1510:138–145 (1991).

Earp, "Fiber Optic SPR Sensors", http://ww.chem.vt.edu/chem–dept/students/Earp/links.html (1998).

Hobbs, "Fluorescence Reveals Toxins on Antibody–Coated Fiberoptic Probe", *Laser Focus World*, (May 1992).

Krull et al., "Fiber Optic Chemoreception", Fiber Optic Chemical Sensors and Biosensors, vol. II, pp. 315–341, CRC Press.

Mauro et al., "Fiber–Optic Fluorometric Sensing of Polymerase Chain Reaction–Amplified DNA Using an Immobilized DNA Capture Protein", *Analytical Biochemistry*, 235:61–72 (1996).

Strachan and Gray, "A Rapid General Method for the identification of PCR Products Using a Fibre–Optic Biosensor and Its Application to the Detection of Listeria", *Letters in Applied Microbiology*, 21:5–9 (1995).

Thompson and Ligler, "Chemistry and Technology of Evanescent Wave Biosensors", Biosensors with Fiberoptics, pp. 111–138, Humana Press.

Xu and Yeung, "Direct Measurement of Single–Molecule Diffusion and Photodecomposition in Free Solution", *Reports*, Oct. 28, 1996; accepted Jan. 7, 1997.

Agrawal et al., "Efficient Methods For Attaching Non–Radioactive Labels To The 5' Ends Of Synthetic Oligodeoxyribonucleotides", *Nucleic Acids Research*, vol. 14, pp. 6227–6245, 1986.

Atkinson et al., "Solid–Phase Synthesis of Oligodeoxyribonucleotides by the Phosphitetriester Method", *Oligonucleotide Synthesis*, pp. 45–49, 1985.

BRL Catalog (1988) p. 181. Published By BRL Life Technologies.

Bannwarth et al., "Formation Of Carboxamides With N,N, N',N'–Tetramethyl (Succinimido) Uronium Tetrafluoroborate In Aqueous/Organic Solvent Systems", *Tetrahedron Letters*, vol. 132, pp. 1157–1160, 1991.

Bunin et al., "The Combinatorial Synthesis and Chemical and Biological Evaluation of a 1,4–benzodiazepine Library", *Proc. Natl. Acad. Sci. USA*, vol. 91, pp. 4708–4712, 1994.

Bunin et al., "A General and Expedient Method For The Solid–Phase Synthesis of 4,–Benzodiazepine Derivatives", *J. Am. Chem. Soc.*, vol. 114, pp. 10997–10998, 1992.

Cole Parmer Catalog (1995–1996) p. 124. Published by Cole Parmer Instrument Company.

Connolly, Bernard A., "The Synthesis Of Oligonucleotides Containing A Primary Amino Group At The 5'–Terminus", *Nucleic Acids Research*, vol. 15, pp. 3131–3139, 1987.

DeWitt et al., ""Diversomers": An Approach to Nonpeptide, Nonoligomeric Chemical Diversity" *Proc. Natl. Acad. Sci. USA*, vol. 90, pp. 6909–6913, 1993.

Durand et al., "Circular Dichroism Studies Of An Oligodeoxyribonucleotide Containing A Hairpin Loop Made Of A Hexaethlylene Glycol Chain: Conformation And Stability" *Nucleic Acids Research*, vol. 18, pp. 6353–6359, 1990.

Duveneck et al., "Novel Bioaffinity Sensors For Trace Analysis Based On Luminescence Excitation By Planar Waveguides", *Sensors and Actuators*, B 38–39; 88–95, 1997.

Egholm et al., "Peptide Nucleic Acids (PNA). Oligonucleotide Analogues With An Achiral Peptide Backbone", *J. Am. Chem. Soc.*, vol. 114, pp. 1895–1897, 1992.

Ferguson et al., "A Fiber–Optic DNA Biosensor Microarray for the Analysis of Gene Expression", *Nature Biotechnology*, vol. 14, pp. 1681–1684, 1996.

Kato et al., "Immobilization of DNA Onto A Polymer Support and Its Potentiality as Immunoadsorbent", *Biotechnology and Bioengineering*, vol. 51, pp. 581–590, 1996.

Ghosh et al., "Covalent Attachment of Oligonucleotides To Solid Supports", *Nucleic Acids Research*, vol. 15, pp. 5353–5372, 1987.

Goodchild et al., "Conjugates of Oligonucleotides and Modified Oligonucleotides: A Review of Their Synthesis and Properties" *Bioconjugate Chemistry*, vol. 1, pp. 165–186, 1990.

Gordon et al., "Applications of Combinatorial Technologies to Drug Discovery. 2. Combinatorial Organic Synthesis, Library Screening Strategies, and Future Directions", *Journal of Medicinal Chemistry*, vol. 37, pp. 1385–1401, 1994.

Gryaznov et al., "Oligodeoxyribonucleotide N3'—>P5' Phosphoramidates: Synthesis and Hybridization Properties", *J. Am. Chem. Soc.*, vol. 116, pp. 3143–3144, 1994.

Jung, et al., "Multiple Peptide Synthesis Methods and Their Applications", *Angewandte Chemie*, vol. 31, pp. 367–486, 1992.

Knorr et al., "New Coupling Reagents In Peptide Chemistry", *Tetrahedron Letters*, vol. 30, pp. 1927–1930, 1989.

Lloyd–Williams et al., "Solid–Phase Peptide Synthesis" (Chapter 2) *Chemical Approaches to the Synthesis Of Peptides And Proteins*, pp. 19–93, 1997.

Lund et al., "Assessment of Methods For Covalent Binding Of Nucleic Acids To Magnetic Beads, DYNABEADS, And The Characteristics Of The Bound Acids In Hybridization Reactions", *Nucleic Acids Research*, vol. 16, pp. 10861–10880.

Maskos et al., "A Study Of Oligonucleotide Reassociation Using Large Arrays Of Oligonucleotides Synthesised On A Glass Support", *Nucleic Acids Research*, vol. 21, pp. 4663–4669, 1993.

Maskos et al., "Parallel Analysis of Oligodeoxyribonucleotide (Oligonucleotide) Interactions. I. Analysis Of Factors Influencing Oligonucleotide Duplex Formation", *Nucleic Acids Research*, vol. 20, pp. 1675–1678, 1992.

Maskos et al., "Oligonucleotide Hybridisations On Glass Supports: A Novel Linker For Oligonucleotide Synthesis and Hybridisation Properties Of Oligonucleotides Synthesised *in situ*", *Nucleic Acids Research*, vol. 20, pp. 1679–1684, 1992.

Nelson et al., "BiFunctional Oligonucleotide Probes Synthesized Using A Novel CPG Support Are Able To Detect Single Base Pair Mutations", *Nucleic Acids Research*, vol. 17, pp. 7187–7194, 1989.

Nelson et al., "A New And Versatile Reagent For Incorporating Multiple Primary Aliphatic Amines Into Synthetic Oligonucleotides", *Nucleic Acids Research*, vol. 17, pp. 7179–7186, 1989.

O'Donnell et al., "High–Density, Covalent Attachment of DNA to Silicon Wafers for Analysis By MALDI–TOF Mass Spectrometry", *Analytical Chemistry*, vol. 69, pp. 2438–2443, 1997.

Pease et al., "Light–generated Oligonucleotide Arrays For Rapid DNA Sequence Analysis", *Proc. Natl. Acad. Sci. USA*, vol. 91, pp. 5022–5026, 1994.

Pilevar et al., "Tapered Optical Fiber Sensor Using Near–Infrared Fluorophores To Assay Hybridization", *Analytical Chemistry*, vol. 70, pp. 2031–2037, 1998.

Rasmussen et al., "Covalent Immobilization of DNA onto Polystyrene Microwells: The Molecules Are Only Bound At The 5' End", *Analytical Biochemistry*, vol. 198, pp. 138–142, 1991.

Simon et al., "Peptoids: A Modular Approach To Drug Discovery", *Proc. Natl. Acad. Sci. USA*, vol. 89, pp. 9367–9371, 1992.

Singer, B., "Alkyl Bases, Nucleosides and Nucleotides", *CRC Practical Handbook of Biochemistry and Molecular Biology*, pp. 385–395, 1985.

Southern et al., "Analyzing and Comparing Nucleic Acid Sequences by Hybridization to Arrays of Oligonucleotides: Evaluation Using Experimental Models", *Genomics*, vol. 13, pp. 1008–1017, 1992.

Thompson et al., "Synthesis and Applications of Small Molecule Libraries", *Chem. Rev.*, vol. 96, pp. 555–600, 1996.

Timofeev et al., "Regioselective Immobilization of Short Oligonucleotides To Acrylic Copolymer Gels", *Nucleic Acids Research*, vol. 24, pp. 3142–3148, 1996.

Uhlman et al., "Antisense Oligonucleotides: A New Therapeutic Principle", *Chemical Reviews*, vol. 90, pp. 544–584, 1990.

Websters II New Riverside University Dictionary, p. 474; 1994.

Wilcheck et al., "Improved Method For Preparing N–Hydroxysuccinimide Ester–Containing Polymers For Affinity Chromatography", *Bioconjugate Chem.*, vol. 5, pp. 491–492, 1994.

Wiley & Sons, Inc., "Surface Treatment", *The Wiley Encyclopedia of Packaging Technology second edition*, pp. 567–874, 1997.

Zhang et al., "Single–Base Mutational Analysis Of Cancer And Genetic Diseases Using Membrane Bound Modified Oligonucleotides", *Nucleic Acids Research*, vol. 19, pp. 3929–3933, 1991.

\* cited by examiner

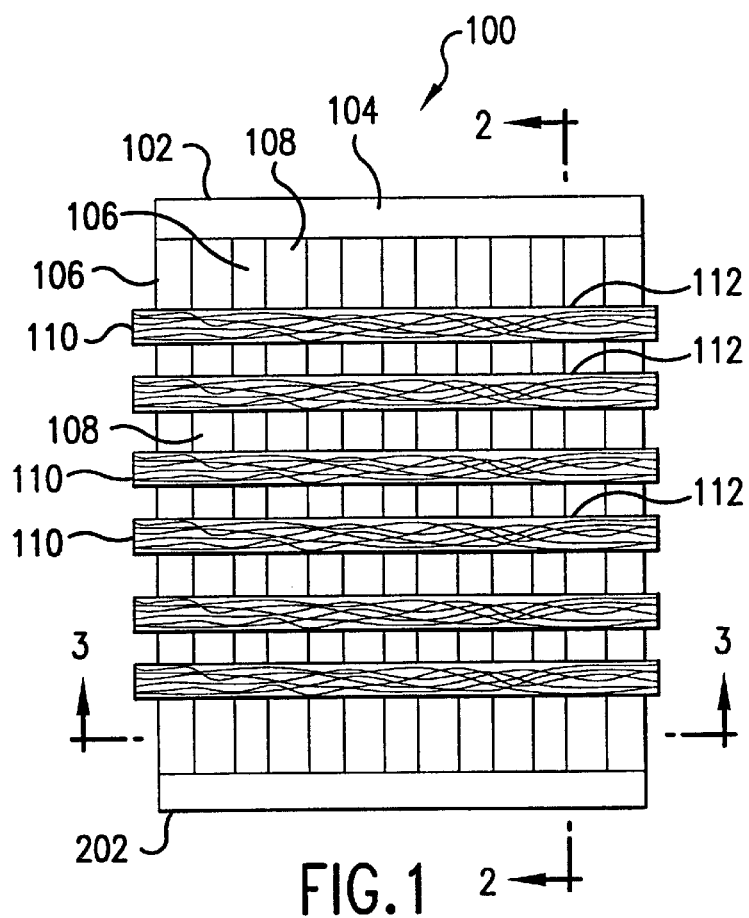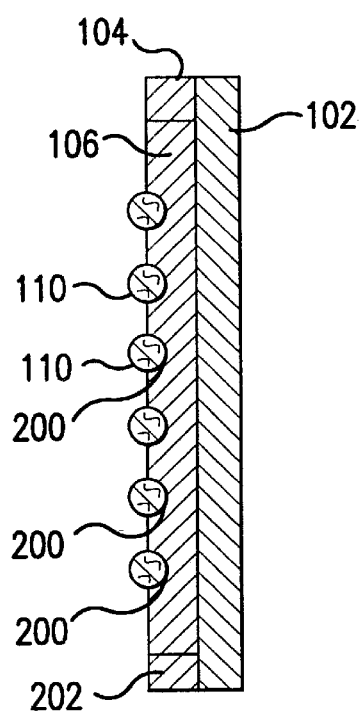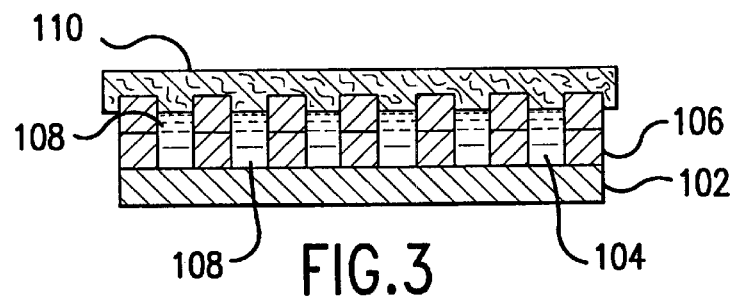

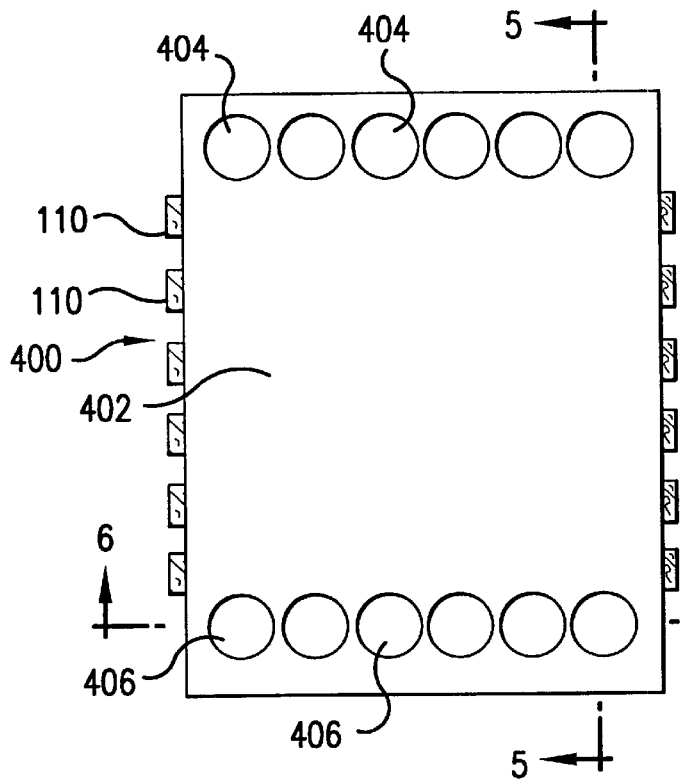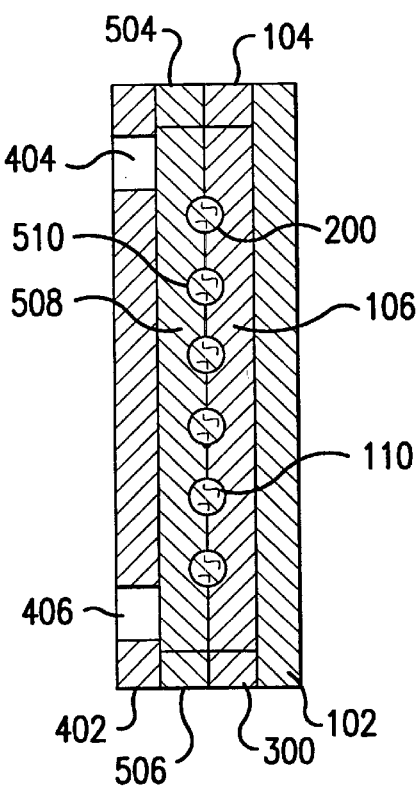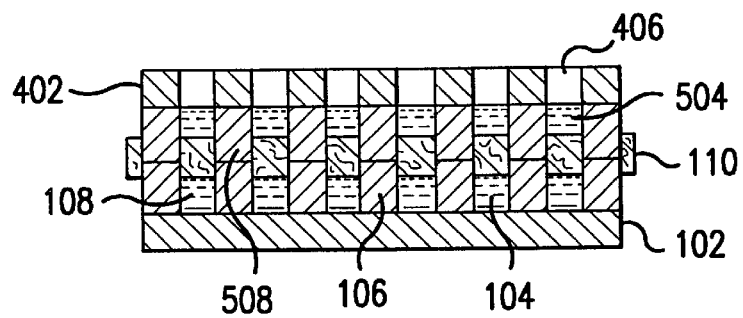

METHOD FOR USING AND MAKING A FIBER ARRAY

This is a division of Ser. No. 09/590,761, filed Jun. 8, 2000, which is a division of Ser. No. 09/479,181, filed Jan. 7, 2000, which is a continuation-in-part of application Ser. No. 09/227,799, filed Jan. 8, 1999, now abandoned.

BACKGROUND OF THE INVENTION

1. Field of the Invention

The invention relates generally to micro-arrays for contacting small quantities of chemical species. More specifically, the invention relates to micro-arrays for contacting an oligonucleotide probe with an oligonucleotide target, a reader for reading the micro-array, and a method and apparatus for making the micro-array.

2. Description of Related Art

Presently, micro-arrays are being used for a wide range of applications such as gene discovery, disease diagnosis, drug discovery (pharmacogenomics) and toxicological research (toxicogenomics). A micro-array is an orderly arrangement of immobilized chemical compounds. Micro-arrays provide a medium for matching known and unknown DNA samples based on base-pairing rules. The typical method involves contacting an array of immobilized chemical compounds with a target of interest to identify those compounds in the array that bind to the target. Arrays are generally described as macro-arrays or micro-arrays, the difference being the size of the sample spots. Macro-arrays contain sample spot sizes of about 300 microns or larger whereas micro-arrays are typically less than 200 microns in diameter and typically contain thousands of spots.

DNA micro-arrays, or DNA (gene) chips are typically fabricated by high-speed robotics on glass or nylon substrates, for which probes with known identity are used to determine complementary binding. A "probe" is a tethered nucleic acid with known sequence, whereas a "target" is the free nucleic acid sample whose identity is being detected.

One array-based application that requires very high density miniaturized arrays is sequencing by hybridization (SBH). In one common format of SBH (format II), a spatially-addressable array of the complete set of oligonucleotide probes of length n is constructed. The oligonucleotide probes are typically covalently attached to a flat, solid substrate, such as a glass slide. Each address in the array has a unique n-mer attached thereto, and the sequence of the probe is defined by its spatial address (xy coordinates). The array is contacted with a labeled target nucleic acid under conditions which discriminate between the formation of perfectly complementary probe-target hybrids and hybrids containing mismatches. Thus, only those addresses of the array which have attached thereto oligonucleotide probes that are completely complementary to a portion of the target nucleic acid produce a signal. The array is then scanned for signals, the sequences of complementary probes determined from their spatial addresses, and the sequence of the target nucleic acid determined by overlapping the common sequences of the probes.

Two other SBH formats also exist. In format I SBH, the target nucleic acid is immobilized on a solid support, e.g., a nylon or nitrocellulose filter, and the immobilized target interrogated with labeled probes. Typically, the target is interrogated with a single probe at a time, or alternatively with a plurality of probes, each of which bears a different distinguishable label (this latter mode is termed "multiplexing"). To reduce the number of manipulations required, the target nucleic acid can be spotted onto a filter in a grid or array, and each spot or address in the array interrogated with a single probe or plurality of multiplexed probes.

In yet another format of SBH, (format III), an array of immobilized oligonucleotide probes similar to that used for format II SBH is contacted with an unlabeled target nucleic acid under conditions which discriminate between perfectly complementary and mismatched hybrids. The array is then contacted with a labeled probe under conditions which discriminate between perfectly complementary and mismatched labeled probe target complexes. Following hybridization, the array is subjected to conditions which covalently join probes which are hybridized adjacently to the target (e.g., a ligase). The unligated labeled probe, and optionally target nucleic acid, is then washed away. The array is then scanned for signal. Since the solution-phase probe was labeled, only those addresses where [ligatia] ligation took place produce a signal. The sequence of the target nucleic acid is determined by overlapping the common sequences of the ligated probes.

For a review of the three types of SBH and their respective advantages, see U.S. Pat. Nos. 5,202,231; 5,525,464; WO 98/31836; WO 96/17957 and the references cited therein.

The length of target nucleic acid which can be sequenced using SBH techniques depends on the lengths of the oligonucleotide probes. Generally, sequencing a target nucleic acid a few hundred nucleotides in length requires the oligonucleotide probes to be at least 8 nucleotides in length. Sequencing longer target nucleic acids, or sequencing though regions of tandem repeats, requires even longer probes. Some have estimated that sequencing a target nucleic acid over one thousand nucleotides in length would require oligonucleotide probes of at least 12 to 14 nucleotides in length. Because the methods require the use of complete sets of probes, i.e., every possible sequence of length n, the probe sets required for the method are extremely large. For example, the complete set of 8-mer probes consists of $4^8$ or 65,356 unique sequences. The complete set of 10-mer probes consists of $4^{10}$ or 1,048,576 unique sequences and the complete set of 14-mer probes consists of $4^{14}$ or 268,435,456 unique sequences. In order to make the assays practical, the entire probe array must typically be on the order of 1 $cm^2$ in area.

To meet the needs of applications requiring high-density miniaturized arrays of immobilized compounds, such as SBH and its related applications, two general methods have been developed for synthesizing the immobilized arrays: in situ methods in which each compound in the array is synthesized directly on the surface of the substrate and deposition methods in which pre-synthesized compounds capable of being covalently attached to the surface of the substrate are deposited, typically by way of robot dispensing devices, at the appropriate spatial addresses. The in situ methods typically require specialized reagents and complex masking strategies, and the deposition methods typically require precise robotic delivery of very defined quantities of reagents.

For example, Fodor et al., 1991, Science 251:767–773 describe an in situ method which utilizes photo-protected amino acids and photo lithographic masking strategies to synthesize miniaturized, spatially-addressable arrays of peptides. This in situ method has recently been expanded to the synthesis of miniaturized arrays of oligonucleotides (U.S. Pat. No. 5,744,305). Another in situ synthesis method for making spatially-addressable arrays of immobilized oligonucleotides is described by Southern, 1992, Genomics 13:1008–1017; see also Southern & Maskos, 1993, Nucl. Acids Res. 21:4663–4669; Southern & Maskos, 1992, Nucl. Acids Res. 20:1679–1684; Southern & Maskos, 1992, Nucl. Acids Res. 20:1675–1678. In this method, conventional oligonucleotide synthesis reagents are dispensed onto physically masked glass slides to create the array of immobilized oligonucleotides.

U.S. Pat. No. 5,807,522 describes a deposition method for making micro arrays of biological samples that involves dispensing a known volume of reagent at each address of the array by tapping a capillary dispenser on the substrate under conditions effective to draw a defined volume of liquid onto the substrate.

One of the biggest drawbacks of both the in situ and deposition micro fabrication techniques is the inability to verify the integrity of the array once it has been fabricated. Absent analyzing the compound immobilized at each address, the integrity of the deposition chemistry simply cannot be verified. Such an analysis would be extremely labor intensive, and may even be impossible for extremely high-density arrays, as the quantity of compound immobilized may not be sufficient for analysis and subsequent use.

Moreover, since each array is fabricated de novo, the integrity of each array synthesized is suspect. Without being able to verify that the array has been fabricated with high fidelity, the absence of a signal at a particular address cannot be unambiguously interpreted. The absence of signal could be due to a failed synthesis or immobilization at that address.

Deposition methods suffer additional drawbacks, as well. Automatic deposition generally uses a robotic fluid delivery system. The robot moves to specific locations on the microcard, delivering a specified amount of fluid. The fluid is deposited onto the microcard by either a non-contact ejector (such as ink jet nozzles) or a contact ejector (such as a pen, quill, or fiber) which actually touches the microcard surface to release the fluid. Ink jets, pens, and quills are adaptations of common devices, and each have reliability problems. Ink jets work fine when the fluid has been carefully optimized for the nozzle. However, when depositing many different fluids through the same nozzle, optimization of each fluid is impractical. Pens and quills are very useful for deposition onto a small number of plates but are too slow for cost-effective production. While a fiber piston delivery system shows promise as a reliable means of fluid deposition, it requires an unwieldy number of fibers for a very large number of reaction sites.

In addition to problems with the reliability of ejectors, the total time to deposit thousands of different probe fluids with existing automated ejector devices increases the cost of a microcard beyond the cost of other approaches, i.e. the automated process is not cost-effective. Somewhat surprisingly, this is not due to the speed of fluid deposition by the robot, which is relatively fast. Rather, it is the combination of other on-line procedures such as wicking, cleaning, and loading slides that makes the total deposition time unacceptable. To have thousands of independent probe liquids means that the robot can only deposit a few spots on one slide (assuming some duplication) before it has to load (wick) another probe fluid into the reservoirs of its ejector or quill. Wicking usually involves providing an open vessel containing the probe fluid such that the robot can move the ejector/quill into the fluid and load the fluid through vacuum or capillary action into a reservoir in the ejector/quill. This process can take several seconds, and must be conducted whenever dispensing a new probe fluid. Also, before introducing a new probe fluid, the ejector/quill must be cleaned to prevent contamination of the new probe fluid with the previous one. This cleaning usually involves flushing the ejector/quill with a cleaning solvent and drying them with flowing gas. The cleaning process also takes several seconds and must be conducted whenever dispensing a new probe fluid. Furthermore, the loading (and unloading) of slides into the robot's workspace also adds to the overall processing time. Since wicking, cleaning, and loading are on-line procedures, they all add to the total time of deposition. Spotting many slides at a time improves the robotic deposition time but still requires the same wicking and cleaning time before depositing a different fluid. Therefore, wicking, cleaning, and loading time alone make the process too time consuming and expensive to consider as a viable alternative.

Consequently, neither in situ nor existing automated approaches are a reliable or cost-effective means of mass-producing micro arrays. Therefore, there is a need for methods of making microarrays that avoid the problems associated with currently available in situ and deposition methods and which provide a matrix or array of contact points for contacting small quantities of at least two chemical species. Furthermore, there is a need for a more advantageous structure for the micro arrays that can provide an increased number of mix points as well as an improved contact efficiency between the chemical species.

Machines for synthesizing chemical chains or compounds onto a solid substrate have been in existence for many years. Typically such synthesizers make oligonucleotides by adding one phosphoramodite (base) at a time onto solid beads. The bases, A, T, C or G, are strung together into a chain of the desired sequence and length. The process of adding these bases may vary from manufacturer to manufacturer. The solid substrate is usually a batch of small polystyrene or glass beads (typically less than 1 mm diameter). A plurality of beads are placed in a container and fluids are passed through the beads. The process usually comprises adding these bases by the following process (1) detritylation, (2) applying base A, T, C or G, (3) adding an activator, (4) applying caping agent A and B, (5) washing with a first solvent, (6) applying an oxidizer, and (7) washing with a second solvent. This process adds one base onto the beads and is repeated for each base desired. The only process variable is the base A, T, C or G which is determined by the compound or chain desired. After all the desired bases are added, the oligos are cleaved (separated) from the beads by an ammonia solution. An extraction process, such as High-pressure Liquid Cromotography (HPLC), separates and purifies the oligos from the ammonia. The final oligo product is in a liquid form that is often marked and stored before being used or sold. The user, typically using a robot, must then conduct another set of steps to deposit and immobilize the liquid oligos onto a solid substrate for analysis purposes.

The disadvantage with existing synthesizers is that the final product is often not application ready. The product is in a liquid form that must typically be inventoried, stored, and usually reapplied onto another substrate, such as a titer-plate or micro-slide, to be analyzed. A more efficient process would be to synthesize the oligos on the same substrate that is ultimately analyzed. Furthermore, if the synthesis process could be automated such that the substrate is continuously fed through the solution, rather than the solution being fed through the substrate, the synthesized product could be placed directly onto the analysis device without the need for inventory, storage, or re-application.

SUMMARY OF THE INVENTION

According to one aspect of the invention there is provided a fiber array for contacting at least two chemical species. The fiber array comprises a support plate having a channel for receiving a mobile chemical species and a fiber, having a second chemical species immobilized thereon, disposed on the support plate. At least a portion of the fiber is exposed to the channel such that the mobile chemical species is capable of contacting the second chemical species. More specifically, the fiber array may be constructed as a matrix of multiple parallel fibers disposed perpendicular to multiple parallel channels, thereby creating a matrix of contact points or mix points between each fiber and each channel.

The invention also provides a method for contacting at least two chemical species and for analyzing the contact between the at least two chemical species. The method for contacting the chemical species comprises immobilizing a chemical species on a fiber, placing the fiber on a support having a channel, and disposing a second, mobile chemical species into the channel such that the mobile chemical species contacts the fiber. The method for analyzing the contact between the two chemical species, comprises immobilizing an immobilized chemical species on at least a first one of a plurality of optical fibers, placing the plurality of fibers on a support having a plurality of channels, disposing a mobile chemical species into at least a first one of the plurality of channels such that the mobile chemical species contacts at least the first one of a plurality of optical fibers, directing light into an end of the at least first one of a plurality of optical fibers, and viewing the excitation light emitted from the surface of at least first one of a plurality of optical fibers. It should be appreciated that the excitation light is that light emitted from the fiber and may also be referred to below as binding light that is produced as indicative of an interaction between two chemical species.

The invention also provides a method for making a microchip having a plurality of contact points, comprising immobilizing each of a plurality of known chemical species on a separate fiber and placing each of the fibers on a support having a plurality of parallel and fluidly independent channels for receiving an analyte, wherein the plurality of fibers are arranged in parallel on the support and substantially normal to the plurality of channels, thereby forming a matrix of contact positions between a portion of each of the fibers and each of the plurality of channels, such that each of the fibers is contacted by the analyte.

The invention also provides an apparatus for detecting the binding of the two chemical species. The apparatus comprises a photo-detector for receiving excitation light emitted from a mobile chemical species bound to an immobilized chemical species on a fiber. The apparatus also comprises a light source, a focusing lens for directing the light to an end of the fiber, and an electrical measuring device electrically connected to the photo-detector.

According to the invention there is furthermore provided a method for detecting the binding of two chemical species, comprising the steps of directing light to a fiber having an immobilized chemical species that has been contacted with a mobile chemical species, and detecting excitation light emitted from the chemical species bound to the immobilized chemical species.

In another aspect of the invention, a fiber wheel mixing apparatus is provided for contacting at least two chemical species. The fiber wheel mixing apparatus comprises a wheel having a perimeter sidewall, at least one fiber disposed on the perimeter sidewall, and an immobilized chemical species disposed on the fiber. Methods for making the fiber wheel mixing apparatus and for using the fiber wheel mixing apparatus are also provided.

The fiber wheel mixing apparatus of the present invention presents a low-cost method for contacting two or more chemical species. Each wheel can include hundreds to thousands of fiber segments providing hundreds to thousands of mix points. By preparing and storing such wheels in advance, a customized fiber wheel mixing apparatus can be rapidly prepared to provide hundreds of thousands to a million mix points or more. This type of mass contacting apparatus provides a significantly enhanced throughput over typical conventional spotting techniques. The throughput would also scale linearly with the length of the fiber and the number of fibers disposed on each wheel. Furthermore, by employing multiple wheels, multiple samples can be simultaneously mixed and tested. Because the processing time for multiple samples is not much greater than that for processing a single sample, labor cost per sample can also be reduced.

According to the invention there is further provided an apparatus for synthesizing a chemical compound on a fiber, comprising at least one depositor capable of depositing a chemical species precursor on a fiber, a transporter for bringing the fiber and the chemical species precursor into proximity with one another such that the chemical species precursor is deposited on the fiber, and a selector for controlling the order in which each of a plurality of chemical species precursors is deposited on the fiber, whereby a predetermined chemical species is synthesized on the fiber.

Still further according to one aspect of the invention there is provided a method for synthesizing the chemical species on the fiber comprising the steps of determining an order for depositing a plurality of chemical species precursors on a fiber, and depositing each of the precursors on the fiber in the order to synthesize a predetermined chemical species.

Finally, according to the invention there is provided a method for analyzing the contact between two chemical species comprising the steps of synthesizing a predetermined chemical species on a fiber, contacting the fiber with a mobile chemical species, passing light to the fiber, detecting excitation light emitted from the fiber.

The invention further provides a system for reading a microchip. The system comprises a plurality of optical fibers each having a polynucleotide probe immobilized thereon and each having a first end. The system also includes a support for the plurality of fibers having a plurality of parallel and fluidly independent channels for receiving a first analyte, wherein the plurality of fibers are arranged in parallel on the support and substantially normal to the plurality of channels, thereby forming a matrix of contact positions between each of the fibers and each of the plurality of channels, such that each of the fibers is contacted by the first analyte. The system further comprises a light source for generating light, a focusing lens for focusing the light on an end of each of the fibers, a light detecting device positioned to receive the excitation light emitted from each of the contact positions, and a motion device connected to the support to align each of the ends with the light.

Other features and advantages of the invention will appear from the following description from which the preferred embodiments are set forth in detail in conjunction with the accompanying drawings.

BRIEF DESCRIPTION OF THE DRAWINGS

FIG. 1 is a top plan view of a fiber array according to the present invention;

FIG. 2 is a cross-sectional view along line 2—2 of the fiber array of FIG. 1 according to the present invention;

FIG. 3 is a cross-sectional view along line 3—3 of the fiber array of FIG. 1 according to the present invention;

FIG. 4 is a top plan view of another embodiment of a fiber array according to the present invention;

FIG. 5 is a cross-sectional view along line 5—5 of the fiber array of FIG. 4 according to the present invention;

FIG. 6 is a cross-sectional view of another embodiment of the fiber array 10A of FIG. 4;

DETAILED DESCRIPTION OF THE PREFERRED EMBODIMENTS

Figure 7:
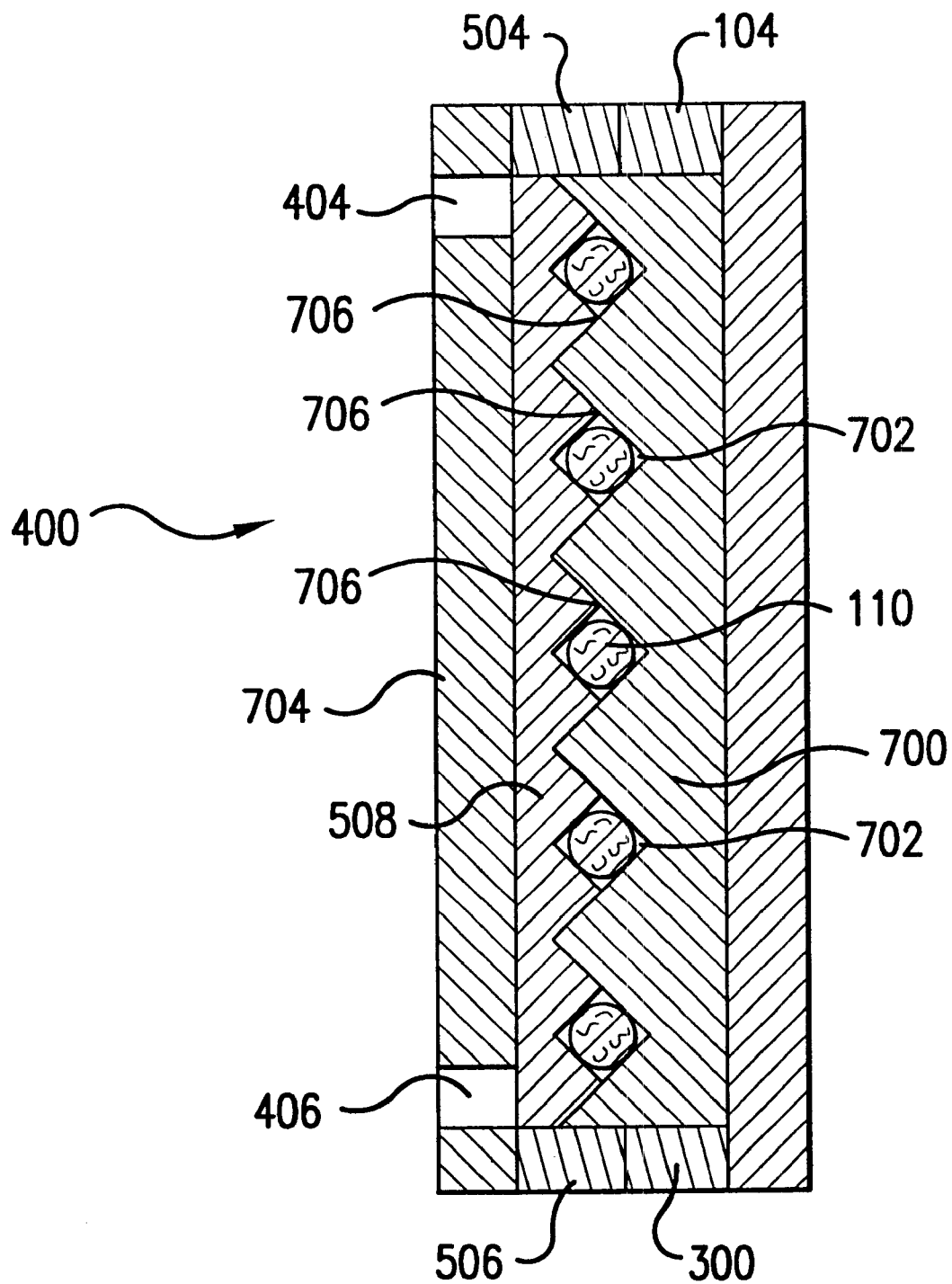
FIG. 7 is a cross-sectional view along line 6—6 of the fiber array of FIG. 4 according to the present invention.

The fiber array of the present invention provides a simple and reliable system for contacting at least two chemical species. Through the use of fibers, the fiber arrays of the invention provide myriad advantages over currently available micro-arrays. For example, fibers having one or a plurality of chemical species immobilized thereon can be prepared in advance and stored, thereby permitting rapid assembly of customized arrays. Quite significantly, customized arrays comprising different types of chemical species can be prepared as conveniently and rapidly as arrays comprised of a single type of chemical species.

Moreover, the arrays of the invention provide reliability that is presently unattainable in the art. For the conventional described above, verifying the integrity of the array prior to use is virtually impossible—chemical species immobilized at each spot in the array would have to be individually analyzed—a task which would be quite labor intensive and, given the small quantities of chemical species immobilized at a spot, may even be impossible. In the arrays of the instant invention, the integrity of the chemical species immobilized on a fiber can be determined by simply analyzing a small portion of the entire fiber. Thus, through the use of fibers, the invention provides, for the first time, the ability to construct arrays of from a few to as many as thousands, millions, or even billions of immobilized compounds rapidly, reproducibly, and with a degree of fidelity that is unprecedented in the art.

In addition, because the chemistry for fabricating an array can be performed in advance, the fiber array of the present invention also avoids wicking, cleaning, and on-line loading associated with immobilizing the chemical with current deposition methods.

Construction of the fiber array is relatively simple. The placement of the fiber on the array is generally only sensitive in one direction, since each fiber can be placed anywhere along its axis. Spotting a micro-array, however, requires the handling of thousands of drops which have to be placed in very specific locations defined by two dimensions. Furthermore, spotting may result in contamination between contact points, whereas, fibers, each having different chemical species immobilized thereon, may be placed next to each other with a reduced potential for such contamination. In situ methods require the development of specialized chemistries and/or masking strategies. In contrast, the arrays of the present invention do not suffer from these drawbacks. They can take advantage of well-known chemistries, and do not require deposition of precise volumes of liquids at defined xy-coordinates. The size of the fiber array of the present invention also allows for a large number of contact points with a relatively small array, thereby reducing the costs of making the array. The fiber array of the present invention also provides for a large number of contact points without the need for significant duplication.

Use of the fiber array of the present invention allows the first chemical to be easily dispensed into channels in the array in order to contact the fibers. In addition, different chemical species may be dispensed into each of the channels, which allows each contact point to be unique. Further, preferred fiber arrays of the present invention provide for a relatively high signal to noise ratio, since the use of fibers with optical properties allows for more controlled illumination of the contact points. The fiber array of the present invention is particularly suited for use in performing nucleic array by hybridization assays for applications such as sequencing by hybridization and detecting polymorphisms among others.

FIGS. 1–3 are various views of one embodiment of a fiber array according to the present invention. FIG. 1 is a top plan view of a fiber array 100 comprising a support plate 102, a pair of end walls 104, 202 and a plurality of channel walls 106 which extend from one end of the support plate 102 to the opposite end. The channel walls 106 form a plurality of channels 108, which also extend from one end of the support plate 102 to the opposite end, for receiving a fluid containing a chemical species of interest. Preferably, the channel walls 106 and the channels 108 are essentially parallel.

The fiber array 100 further comprises a plurality of fibers 110 each having immobilized thereon a chemical species of interest to be contacted with the chemical species dispensed in the channels 108. The fibers 110 are disposed on the plurality of channel walls 106 such that each fiber 110 is physically separated from each adjacent fiber 110. Preferably, the fibers 110 are placed in a position essentially parallel to each other and essentially normal to the channels such that a portion of each fiber 110 is in fluid contact with the fluid in each channel 108. This arrangement of the fibers 110 relative to the channels 108 effectively creates a matrix or array of contact points 112 or mix points between the chemical species in the fluid in each of the channels 108 and the chemical species immobilized on each fiber 110.

FIG. 2 is a cross-sectional view along line 2—2 of FIG. 1 of the fiber array 100 according to the present invention. The channel walls 106 are designed to receive the fibers 110. As shown, the channel walls 106 have a groove 200 on top of the channel walls 106 to receive the fibers 110. This allows the fibers 110 to extend into the channels 108 to provide for direct contact between at least a bottom portion of each of the fibers 110 and the fluid in the channels 108. One of skill in the art would recognize that a different geometry for the groove 200 can be used based upon the geometry of the fibers 110.

FIG. 3 is a cross-sectional view along line 3—3 of FIG. 1 of the fiber array 100 according to the present invention. The channels 108 are formed by the channel walls 106 and the top of the support plate 102 and extend along the support plate 102 until terminated by end walls 104, 202. Again, a bottom portion of each fiber 110 is exposed to each channel 108 such that placing a fluid in channel 108 will result in contact between the chemical species in the fluid and the chemical species immobilized on each of the fibers 110.

The support plate 102, end walls 104, 202 and channel walls 106 may be made of any material that is essentially inert to the chemical species of interest. One of ordinary skill in the art would be able to select an appropriate material for these features. In one embodiment the support plate 102, end walls 104, 202 and channel walls 106 may be made of a hydrophobic material to reduce seepage of fluid through the channel walls 106, thereby wetting only the fibers 110 and reducing the amount of fluid required. It should be appreciated that the dimensions of the support plate 102, end walls 104, 202 and channel walls 106, including the number of channels 108, may be altered depending upon the size of the array desired and the amount of fluid available to dispense in the channels 108. However, it is important to keep the height of the channel walls 106, the grooves 200, and the distance between the channel walls 106 of such relative proportions to insure sufficient exposure of the surface area of the fibers 110 to the fluid in the channels 108. Further, it should be appreciated that the thickness of the channel walls 106 may also be altered to optimize the overall size of the fiber array 100. Without limiting the dimensions of an array that could be made according to the present invention, typical dimensions for the support plate may range from 1 cm to 1000 cm. The thickness of the channel walls may range from 10 μm to 1000 μm, and the channel width may range from of 10 μm to 1000 μm. The height of the channel walls may range from 10 μm to 1000 μm.

The fiber 110 can be composed of virtually any material or mixture of materials suitable for immobilizing the particular type of chemical species. For example, as will be discussed in conjunction with FIG. 12, the fiber may be an electrically conductive wire. Alternatively, the fiber may be an optical fiber. Moreover, the use of the term "fiber" is not intended to imply any limitation with respect to its composition or materials of construction or geometry. Preferably, the fiber 110 will not melt, degrade, or otherwise deteriorate under the conditions used to immobilize the chemical species or under the desired assay conditions. In addition, the fiber 110 should be composed of a material or mixture of materials that does not readily release the immobilized chemical species under the desired assay conditions. The actual choice of material will depend upon, among other factors, the identity of the chemical species immobilized and the mode of immobilization and will be apparent to those of skill in the art.

As will be discussed in more detail in conjunction with the preparation of the fiber 110, below, in embodiments employing covalent attachment of the chemical species, the fiber 110 is preferably composed of a material or mixture of materials that can be readily activated or derivatized with reactive groups suitable for effecting covalent attachment. Non-limiting examples of suitable materials include acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVA), polyvinylidene fluoride (PVDF), polychlorotrifluoroethylene (PCTFE), polyethylene-chlorotrifluoroethylene (ECTFE), polyvinyl alcohol (PVA), silicon styrene-acrylonitrile (SAN), styrene maleic anhydride (SMA), metal oxides, and glass.

In a preferred embodiment, the fiber 110 is an optical fiber. The optical fiber is typically between about 10 μm and 1000 μm in diameter and can be comprised of virtually any material so long as it is an optical conductor at the wave length of interest. For example, the optical fiber may be an organic material such as polymethacrylate, polystyrene, polymethyl phenyl siloxane, or deuterated methyl methacrylate, or it may be an inorganic material such as glass. In certain embodiments of the invention, a beam of light directed through such optical fiber can be used to detect and/or quantify the interaction between the chemical species in the fluid and the chemical species on the fibers (described below).

It should be appreciated that each fiber 110 may actually contain a different chemical species, or multiple chemical species, in different positions along the fiber 110 or in multiple layers on the fiber 110. Therefore, the preparation of each fiber 110 and immobilization of the desired chemical species thereto will vary depending upon the type of fiber 110 used, the mode of immobilization, and the identity of the chemical species. Various methods for preparing fibers having a variety of chemical species immobilized thereon are discussed in detail in a later section.

The number of fibers 110 comprising fiber array 100 will vary depending upon the size of the matrix desired or the number of different chemical species desired to be reacted with the chemical species in the channels 108. The fibers 110 may be almost any length; however, the length should preferably be sufficient to traverse all of the channels 108. It should be appreciated, however, that the fibers 110 may actually be of any length, diameter, or shape.

In general operation and use of the fiber array 100, a fluid containing one chemical species of interest is dispensed into the channels 108. The fluid may be dispensed using any method known in the art for dispensing a fluid, such as pumping, aspirating, gravity flow, electrical pulsing, vacuum or suction, capillary action, or electro-osmosis. (One device for dispensing fluid onto the fiber array 100 is described below in connection with FIG. 10.) Enough fluid is dispensed to insure contact with a portion of some or all of the fibers 110. The fiber is contacted with the fluid under conditions and for a period of time conducive to promoting interaction between the two chemical species. In instances where excess chemical species in the fluid interferes with the detection of the interaction, the fluid may be removed and the fibers optionally washed prior to detection. The interaction, if any, between the chemical species in the fluid and that on the fibers 110 is then analyzed at one or more contact points 112.

In some instances such as assays involving hybridization of nucleic acids, it may be desirable to control the temperature of the fiber array during the assay. This can be achieved using a variety of conventional means. For example, if the device is constructed of an appropriate conductor, such as anodized aluminum, the device may be contacted with an appropriately controlled external heat source. In this instance, the fiber array would act essentially as a heat block. Alternatively, the channels 108 could be outfitted with heaters and thermocouples to control the temperature of the fluid disposed within the channels.

The method by which the interaction is analyzed will depend upon the particular array. For example, where the two chemical species each constitute one member of a binding pair of molecules (for example, a ligand and its receptor or two complementary polynucleotides), the interaction can be conveniently analyzed by labeling one member of the pair, typically the chemical species in solution, with a moiety that produces a detectable signal upon binding. Only those contact points 112 where binding has taken place will produce a detectable signal.

Any label capable of producing a detectable signal can be used. Such labels include, but are not limited to, radioisotopes, chromophores, fluorophores, lumophores, chemiluminescent moieties, etc. The label may also be a compound capable of producing a detectable signal, such as an enzyme capable of catalyzing, e.g., a light-emitting reaction or a colorimetric reaction. Preferably, the label is a moiety capable of absorbing or emitting light, such as a chromophore or a fluorophore.

Alternatively, both chemical species are unlabeled and their interaction is indirectly analyzed with a reporter moiety that specifically detects the interaction. For example, binding between an immobilized antigen and a first antibody (or visa versa) could be analyzed with a labeled second antibody specific for the antigen-first antibody complex. For polynucleic acids, the presence of hybrids could be detected by intercalating dyes, such as ethidium bromide, which are specific for doublestranded nucleic acids.

Those of skill in the art will recognize that the above-described modes of detecting an interaction between the two chemical species at a contact point are merely illustrative. Other methods of detecting myriad types of interactions between chemical species are well known in the art and can be readily used or adapted for use with the fiber arrays of the present invention.

It should be appreciated that since each channel 108 is fluidly isolated from each other channel 108, a different chemical species may be dispensed into each channel 108. If each fiber 110 has a different chemical species immobilized thereon, this would create a matrix of contact points 112 in which each contact point 112 is unique. Furthermore, while not a preferred mode of operation, chemical species may be serially or simultaneously dispensed into the same channels 108. Sequential dispersing is particularly useful, for example, where the chemical species immobilized on fiber 110 is synthesized in situ on the fiber 110.

FIGS. 4–6 are various views of another embodiment of a fiber array 400 according to the present invention. Fiber array 400 is similar to fiber array 100, but with the addition of a cover plate 402. FIGS. 4–6 are essentially the same views as FIGS. 1–3, but show a cover plate 402. It should be appreciated that while a cover plate is convenient in operation and use of the fiber array, it is not necessary.

FIG. 4 is a top plan view of fiber array 400, according the present invention. Cover plate 402 comprises a plurality of channel inlet ports 404, which are each fluidly connected to separate channels 108 at one end of the channels 108, and a plurality of channel outlet ports 406, which are also each fluidly connected to separate channels 108 at the opposite end of the channels 108. The channel inlet ports 404 provide an opening through which the fluid containing a chemical species of interest is dispensed into a respective channel 108. The channel outlet ports 406 allow the fluid to exit the fiber array 400. Similar to the support plate 102, cover plate 402 may be made of any material that is essentially inert to the chemical species of interest, and one of ordinary skill in the art would be able to select an appropriate material. Further, it should be appreciated that cover plate 402 may be transparent to facilitate detection of the interaction between the chemical species being contacted.

FIG. 5 is a cross-sectional view of the fiber array 400 along line 5—5 of FIG. 4. The cover plate 402 comprises a pair of end walls 504, 506 which mate with the end walls 104, 202, respectively, of the support plate 102. The cover plate 402 further comprises a plurality of channel walls 508 which also mate with the channel walls 106 to seal each channel 108 such that fluid cannot pass from one channel to another. The channel walls 508 also have grooves 510 for receiving the fibers 110. The channel walls 508 and the channel walls 106 also mate to enclose and secure those portions of the fibers 110 laying within the grooves 510, 200. It should be appreciated that the cover plate 402 may be secured to the support plate 102 by any method for adhering two materials depending upon their specific composition. For example, diffusion bonding, inert adhesives, laser or ultrasonic welding, or fasteners may all be used. Other methods for securing two structures together are well known in the art.

FIG. 6 is a cross-sectional view of the fiber array 400 along line 6—6 of FIG. 4. The channels 108 extend above and below the fibers 110 such that the longitudinal portions of the fibers 110 exposed to the channels 108 may be surrounded by the fluid introduced into the channels 108. The channel outlet ports 46 extend through the cover plate 42 to allow the fluid to pass from the channels 108 through the cover plate 42 and out of the fiber array 400. The channel inlet ports are constructed in a similar fashion to allow the fluid to pass through the cover plate 42 into the channels 108.

The operation and use of the fiber array 400 with the cover plate 402 is essentially the same as the fiber array 100 without the cover plate 402. However, the cover plate 402 fluidly seals each of the channels 108, thereby allowing for other methods to be used to move the fluid through the channels 108. For example, a pump may be used to pressurize the fluid in the channels 108, thereby forcing the fluid through the channels. Alternatively, centrifugal force may be used to force the fluid through the channels.

FIG. 7 is a cross-sectional view of another embodiment of the fiber array 400 of FIG. 4 illustrating a preferred design for securing the fibers 110 between the support plate and the cover plate. As shown, support plate 700 comprises grooves 702 for receiving the fibers 110. Cover plate 704 comprises a plurality of teeth 706 which correspond and mate with the grooves 702. This configuration allows the cover plate to be more easily aligned in securing it to the support plate 700, since any tooth 706 may be mated with any groove 702. It should be appreciated that any design or shape for the teeth and the groove may be used. Moreover, it should be appreciated that the fiber array 400 may be constructed without grooves for securing the fibers 110, and the fibers may simply be pinched between the support plate and the cover plate upon securing the support plate to the cover plate.

Figure 8:
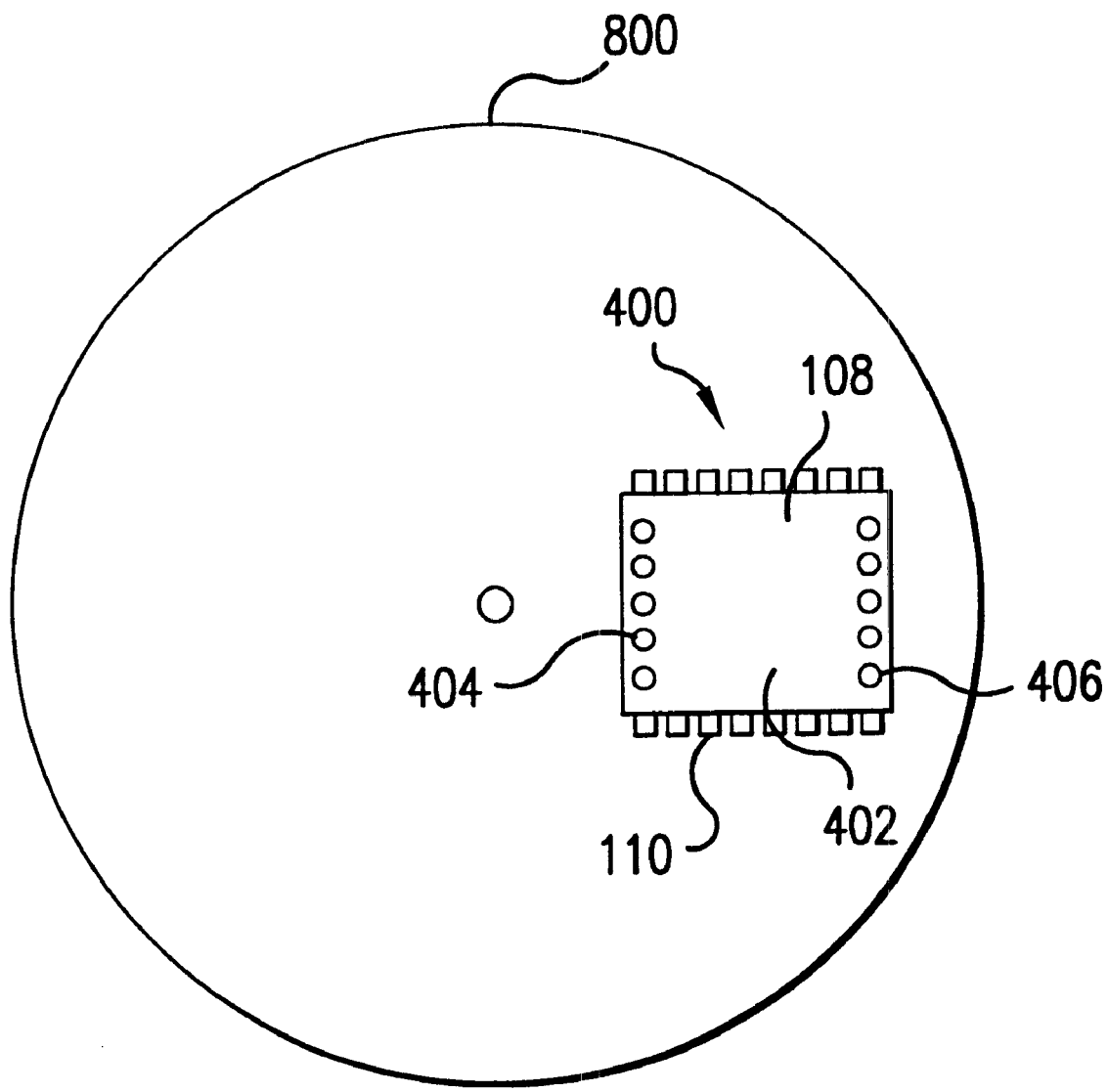
FIG. 8 is a top plan view of a device for moving the fluid through the channels of a fiber array according to the present invention.

FIG. 8 is a top plan view of a device for moving the fluid through the channels 108 of the fiber array 400 having a cover plate 402. Rotating plate 800 is any device which can be rotated about its center axis. The fiber array 400 is secured to the rotating plate 800 such that the channel inlet ports 404 are located near the center of the rotating plate 800, and the channels 108 extend radially outward toward the outer perimeter of the rotating plate 800. The fiber array 400 may be secured to the rotating plate 800 by any means known in the art such as hooks, clips, screws, bolts, magnets and the like. As the rotating plate 800 is rotated about its axis, centrifugal force will move the fluid from the end of the channels 108 near the channel inlet ports 404 through the channels 108 toward the channel outlet ports 406, thereby moving the fluid past each fiber 110. The channel outlet ports 406 may be sealed to prevent the fluid from exiting the fiber array during rotation. It should be recognized that additional fiber arrays may be placed on the rotating plate 800 at the same time.

Figure 9:
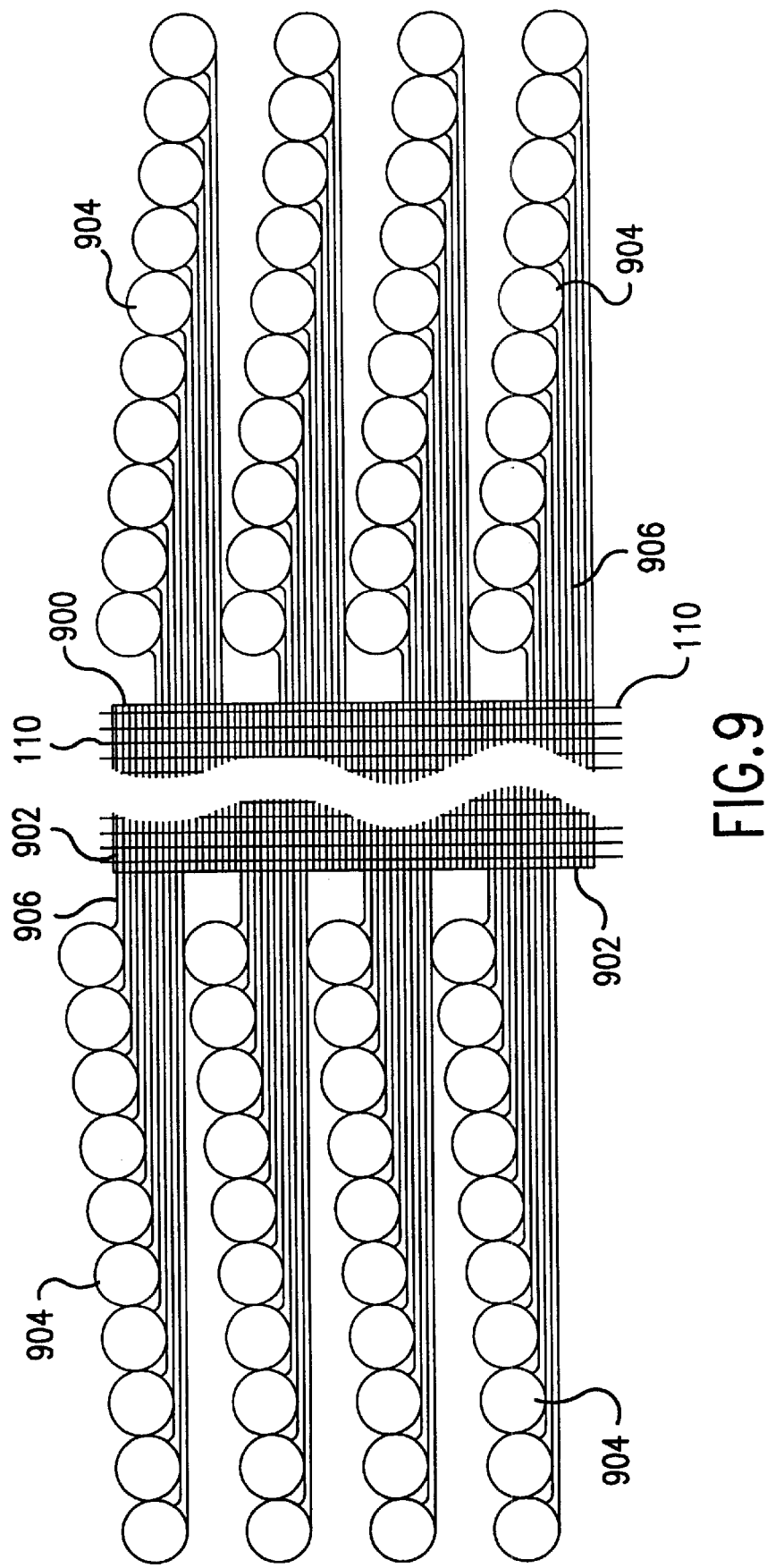
FIG. 9 is a top plan view of another embodiment of a fiber array according to the present invention.

FIG. 9 is a top plan view of another embodiment of a fiber array 900 according to the present invention. The fiber array 900 is similar to the fiber array described in connection with FIGS. 1–8, comprising a plurality of fibers 110 and a plurality of channels 902 intersecting the fibers 110. Preferably, the fibers 110 are essentially parallel to each other, and the channels 902 are essentially perpendicular to the fibers 110. The fiber array 900, however, additionally comprises a plurality of channel inlet ports 904 which are each connected to a respective channel inlet line 906. Each channel inlet line 906 is connected to one end of a respective channel 902 and allows fluid to pass from each of the channel inlet ports 904 to its respective channel 902 within the fiber array 900. The opposite end of each channel 902 is sealed.

The channel inlet ports 904 are arranged to facilitate dispensing the fluid into each channel inlet port 904 with ease and without resort to techniques and micro-sized equipment for dispensing fluid into extremely small openings. With a larger opening, each channel inlet port 904 can accommodate a larger apparatus for dispensing fluid such as a pipette or syringe, thereby reducing the error associated with the transfer of small volumes of fluid.

To provide such larger openings, the channel inlet ports 904 are positioned adjacent to the fiber array 900 and are connected to their respective channels 902 by a channel inlet line 906. FIG. 9 shows several groups of ten channel inlet ports 904, each arranged on alternating sides of the fiber array 900. Each channel inlet port 904 within one group is offset in two directions from its adjacent channel inlet port 904. Specifically, each channel inlet port 904 is offset in a direction parallel to the channels by a distance equivalent to the size of the opening of the channel inlet port 904 and in a direction parallel to the fibers 110 by a distance equivalent to one channel width. This necessitates that each channel inlet line 906 will be of increasing length. However, in this manner the size of the channel inlet port 904 can be maintained, as well as the alignment between the channel inlet port 904, its respective channel inlet line 906 and its respective channel 902.

The channel inlet ports 904 are arranged in this fashion until the width of all of the adjacent channel inlet ports 904 in one group, as measured in a direction parallel to the fibers, is equivalent to the size of the opening of one channel inlet port 904. This arrangement of a group of channel inlet ports 904 is then repeated on the opposite side of the fiber array 900. This alternating arrangement of groups of channel inlet ports 904 and their respective channel inlet lines 906 can be continued along the fiber array 900 indefinitely. While this is the preferred arrangement of the channel inlet ports 904 and their respective channel inlet lines 906, it should be appreciated that the channel inlet ports 904 may actually be positioned in any fashion along the fiber array 900.

It should be noted that the channels 902 are also positioned in an alternating fashion corresponding to the groups of channel inlet lines 906, since one end of each channel 902 is sealed. Therefore, in alternating fashion, a number of channels 902, equivalent to the number of channel inlet lines 906, will have their open ends on one side of the fiber array 900 and the next group of channels 902 will have their open ends on the other side of the fiber array 900. Further, since the channels 902 are sealed at one end there is no channel outlet port. Therefore, in operation, a sufficient quantity of fluid is simply dispensed into the channel inlet ports 904 and is not removed from the channels 902.

Figure 10:
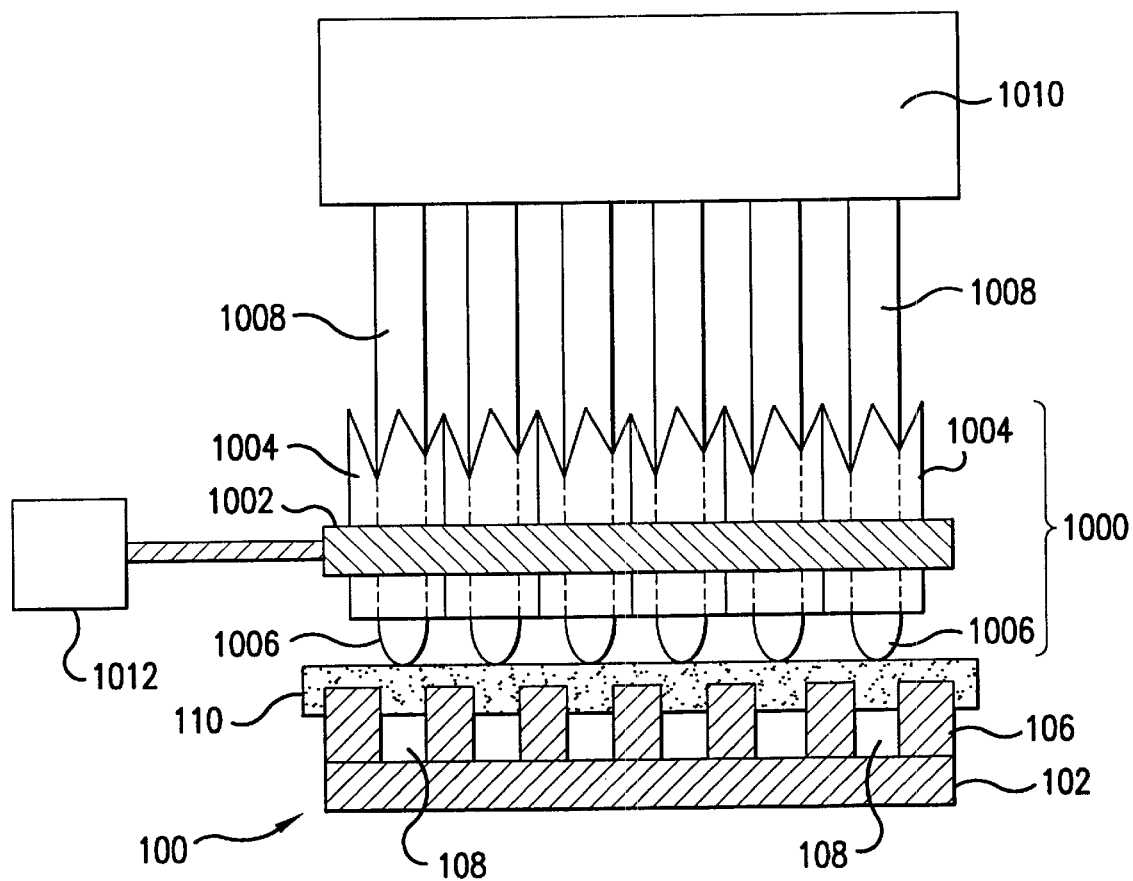
FIG. 10 is a cross-sectional view of a fluid dispensing device for use a the fiber array according to the present invention.

FIG. 10 is a cross-sectional view of a fluid dispensing device for use with the fiber array 100 of FIGS. 1—3. The fluid dispensing device 1000 comprises a fluid dispenser body 1002 which fixedly holds a plurality of fluid dispensers 1004, each having a fluid dispenser opening 1006. Each fluid dispenser 84 is aligned over a channel 108 such that there is one fluid dispenser 1004 for each channel 108. It should be appreciated, however, that a greater or lesser number of fluid dispensers 1004 may be used to feed additional channels or to provide more than one dispenser per channel. Fluid is fed to each fluid dispenser opening 1006 by a fluid feed line 1008 which is fluidly connected to a fluid delivery system 1010. The fluid delivery system 1010 may be any system known in the art that is capable of metering and delivering fluid to a fluid line, such as a pump, an aspirator, by capillary action, by moving a given quantity of fluid from a reservoir through the fluid feed lines 1008 and out of the fluid dispenser openings 1006. The fluid dispenser openings 1006 permit the fluid to be disposed either into the channels 108 or onto the fibers 110. The dispenser openings 1006 may be simply openings at the end of the fluid feed line 1008, nozzles, pipette tips, syringe or needle tips, capillary tubes, quills, or ink jets. Other devices through which a fluid is conveyed are well known in the art. It should be appreciated that the fluid delivery system 1010 should also have the capability of metering and delivering different fluids to each of the fluid feed lines 1008. This permits the ability to contact each of the fibers with a different chemical species.

The fluid dispenser body 1002 is connected to a motion device 1012 which acts to move the fluid dispenser body 1002 in a direction parallel to the channels 108. This permits the fluid dispensing device 1000 to dispense fluid at various locations along each channel 108 or onto each fiber 110. In addition, the motion device 1012 may move the fluid dispenser body 1002 in a direction parallel to the fibers. This allows for the use of fewer fluid dispensers 1004, since a given set of fluid dispensers 1004 may be moved and aligned to dispense fluid into another set of corresponding channels 108. The motion device 1012 may be any type of mechanical device which operates to move an object within a horizontal plane, such as a conveyor or a rotating screw system to certain xy-coordinates. Motion devices of this type are well known in the art.

In operation, a chemical species to be contacted with the chemical species immobilized on the fibers 110 may be placed in a carrier fluid held in a reservoir within the fluid delivery system 1010. Upon demand, for example by computer control, the fluid dispenser body 1002 is moved to a desired location above the fiber array 100, and the fluid delivery system 1010 delivers the fluid to the fluid dispensers 1004 and ultimately to the respective channels 108 or onto the respective fibers 110. Depending upon the geometry of the fiber array and the volume of the channels 108, the amount of fluid dispensed will vary; however, a sufficient amount of fluid should be dispensed to insure adequate contact with the fibers 110. The fluid dispenser body 1002 can then be moved to another location, either along the same channel 108 or to a different channel 108 to dispense additional fluid. It should be appreciated that each fluid dispenser 1004 may dispense a different fluid, or a second fluid may be dispensed after the first fluid is dispensed. In this latter case, rinsing of the fluid feed lines 1008 and the fluid dispensers 1004 before dispensing the second fluid may be appropriate.

Figure 11:
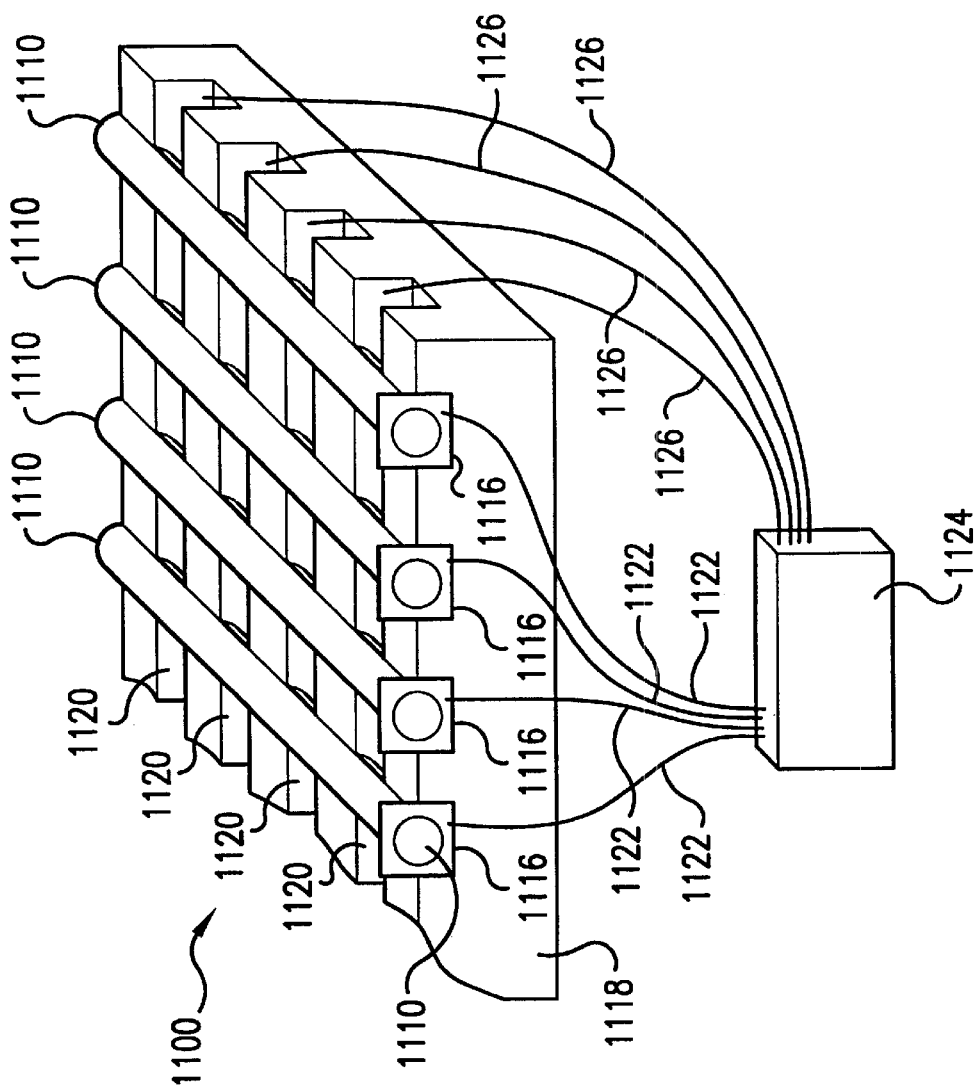
FIG. 11 is a perspective view of a portion of another embodiment of a fiber array according to the present invention.

FIG. 11 is a perspective view of a portion of another embodiment of a fiber array according to the present invention which uses electro-osmosis to move a fluid through the channels of the fiber array to assist in contacting the fluid and the fibers. The fiber array 1100 is essentially the same as those previously described; however, the fibers 1110 are conductive. The fibers 1110 may be made conductive by applying a conductive coating (not shown), which underlies the chemical species (not shown) immobilized on the fibers 1110, such as silver or gold. Alternatively, the fibers 1110 may be made conductive by constructing the fiber 1110 itself of a materially that is electrically conductive and which optionally transmits light, such as indium tin oxide. A conductive contact 1116 surrounds the fibers 1110 at the edge of the support plate 1118. The conductive contact 1116 serves as a means for electrically connecting a power supply 1124 to each of the fibers 1110 using wires 1122. Wires 1126 connect the power supply 1124 to the fluid in channels 1120 thereby completing the circuit.

In operation, the fibers 1110 would be charged and made electrically conductive by supplying power from the power supply 1124 to the conductive contact 1116 of each fiber 1110, and therefore, to the conductive coating of each fiber 1110. The fluid dispensed into the channels 1120 would comprise, in addition to the chemical species of interest, an electrolyte that would be in contact with the power supply 1124 using wires 1126, thereby completing the circuit. The application of power to the fibers 1110 causes the fluid containing the chemical species of interest to move through the channel 1120 through electro-osmosis. Power may then be supplied to an adjacent fiber to move the fluid further along the channel 1120. It should be appreciated that power may be supplied sequentially to single fibers or to groups of fibers. It should also be appreciated that the voltage necessary for electro-osmosis may vary with the electrolyte used, the chemical species of interest and the materials used to construct the channel walls, which preferably should be non-conductive, such as glass or plastic. Typical voltages applied to the fibers may range from a few volts to several kilovolts. Therefore, power supply 1124 must be capable of providing such a range of voltages.

Additionally, electrophoretic forces may be used to provide a greater degree of contact between the chemical species of interest in the fluid and those immobilized on the fiber. Using the embodiment of FIG. 11, the polarity of the fiber and the electrolytic fluid may be reversed using the power supply 1124 in an oscillating fashion at frequencies in the kilohertz range. By reversing the polarity in an alternating fashion, the chemical species of interest in the fluid may be drawn closer to the chemical species on the fiber and then pushed away in the event that the desired interaction does not occur. The process of drawing the chemical species in the fluid close to the fiber may increase the efficiency of contact between the chemical species. The process of pushing the chemical species in the fluid away from the fiber may increase the accuracy of the interactions by reducing the number of false interactions wherein an interaction is detected due to non-specific binding to the fiber, but not a true interaction between the chemical species of interest. The voltages and oscillating frequencies necessary to accomplish this will be dependent upon the composition of the fluid and the chemical species of interest. It should be appreciated, however, that the force used to push the chemical species in the fluid away from the fiber must not be so great as to disrupt a true interaction with the chemical species on the fiber. The use of electrophoresis is further described in U.S. Pat. Nos. 5,605,662 and 5,632,957, both of which are incorporated herein by reference.

Figure 11A:
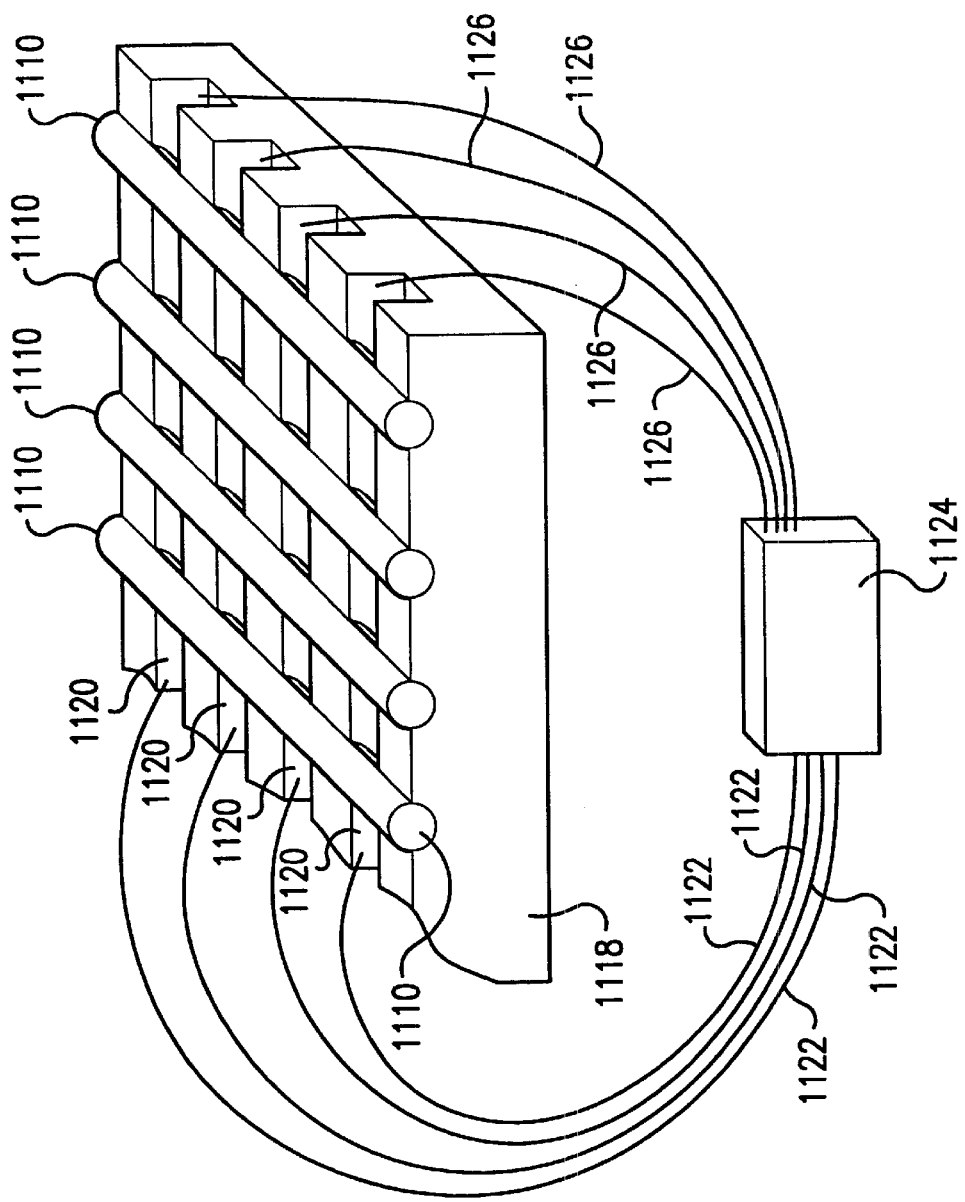
FIG. 11A is a perspective view of a portion of yet another embodiment of a fiber array according to the present invention.

FIG. 11A is a perspective view of a portion of yet another embodiment of a fiber array according to the present invention. In this embodiment, the wires 1122 may be positioned within the fluid at the end of the channel distal from the end where wires 1126 are positioned. Both sets of wires 1122 and 1126 are connected to the power supply 1124, thereby completing the circuit. In addition, it should be appreciated that the invention may easily be adapted to provide a charged surface, using, for example, a channel wall, that enables electro-osmosis or electrophoresis.

As described above, the fiber array of the present invention is used to contact at least two chemical species and to detect and/or quantify an interaction between these species. One of skill in the art would be able to select an appropriate detection method for use with the fiber array of the present invention, such as those previously described. In some cases, especially those instances where the interaction between the chemical species in solution and that immobilized on the fiber cause a difference in the absorbance or emission of light, such as those instances where the chemical species disposed within the channels 108 are labeled with a fluorophore, it is desirable to measure the amount and/or wavelength of light emanated from each of the contact points 112 as a result of the interaction between the chemical species in the channels 108 and on the fibers 110 using a light evaluating device such as the human eye, a camera, or spectrometer. To accomplish this, the entire support plate 102 may be illuminated; however, this may create undesirable background illumination and reduce the signal to noise ratio in the light evaluating device. Therefore, it may be desirable to more selectively illuminate a portion of the fiber array, for example a single fiber or a group of fibers for evaluation, thereby providing greater distinction between contact points 112.

Figure 12:
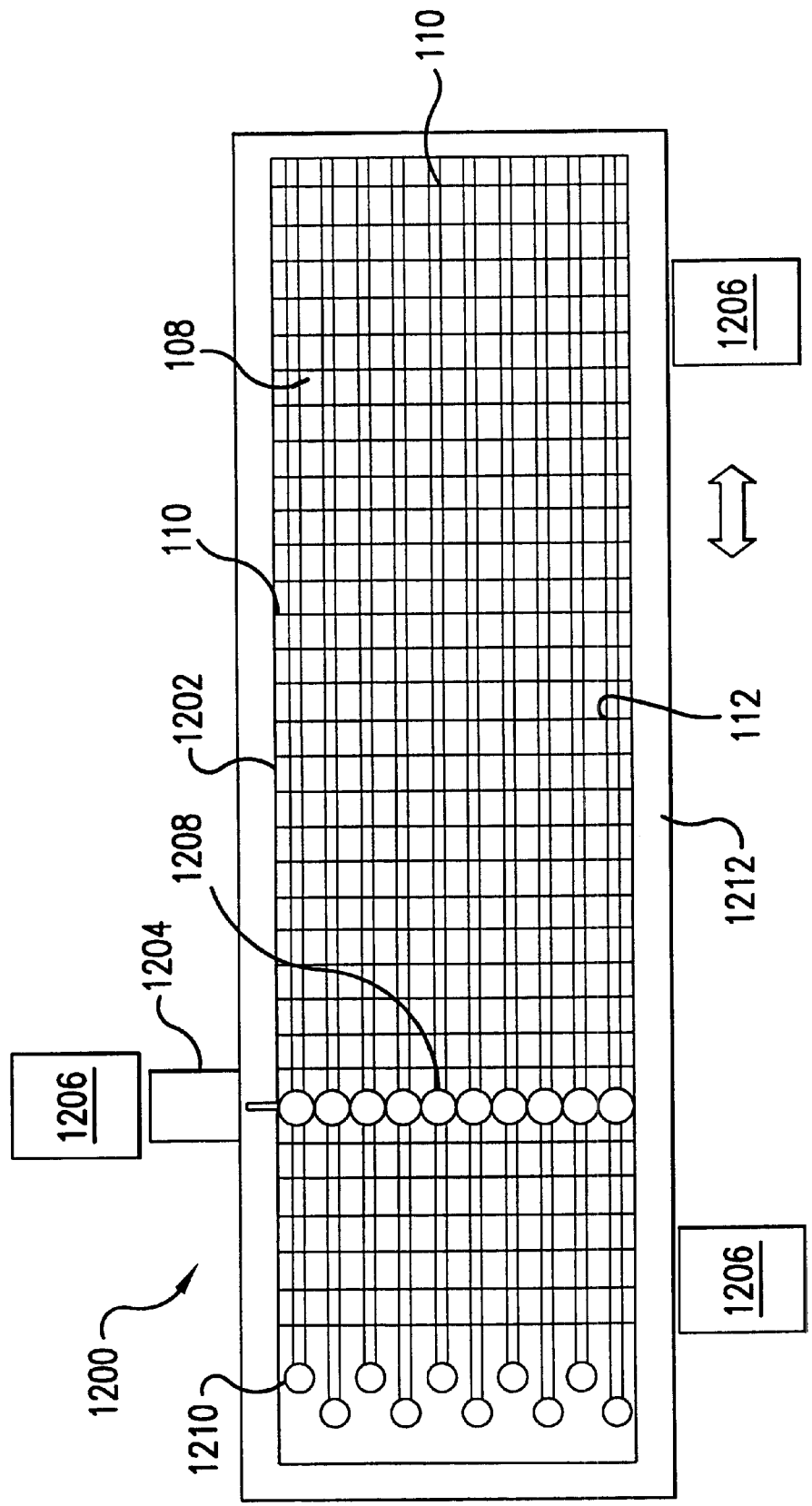
FIG. 12 is a schematic of an embodiment of a fiber array reader according to the present invention.

FIG. 12 is a schematic of an embodiment of a fiber array reader 1200 according to the present invention. The fiber array 1202 may be the same as the fiber array 100 shown in FIGS. 1–3, the fiber array 400 having a cover plate 402 as in FIGS. 4–6, or the fiber array 900 as in FIG. 9; however, the fibers 110 are optical fibers. For purposes of the present invention, an optical fiber is any material used as a fiber which is transparent to a given wavelength or wavelengths of light. The fiber array reader 1200 consists of a light source 1204, such as an excitation laser or an arc lamp, which produces a beam of light having the desired wavelength, which is directed to the end of a fiber 110. A motion device 1206 is used to move the light source 1204 and the fiber array 1202, relative to one another. Either the light source 1204 is moved, the fiber array 1202 is moved, or both are moved relative to one another by the motion device 1206. Any motion device 1206 known in the art maybe used such as a stepper motor or a conveyor powered by a reversible motor capable of moving the conveyor back and forth. A motion detection system with motion sensors (not shown), such as infrared light sensors, may be used to monitor the position of the motion device 1206. The reader 1200 may further comprise light evaluating devices or detectors 1208 which may comprise any device capable of receiving and at least qualitatively evaluating light such as the human eye, a camera (e.g., confocal or CCD camera) or a spectrometer. The detectors 1208 are positioned above contact or mix points 112 which occur at the intersection of the fibers 110 and the channels 108. The reader 1200 may also include a heater 1212 to ramp temperature as will be discussed infra in relation to FIG. 17.

In operation, a fluid is inserted into input holes 1210 at one end of a channel 108. The fiber 110 is thereby contacted with the fluid containing a chemical species under conditions conducive to interaction between the chemical species immobilized on fiber 110 and the chemical species in solution. Each channel may receive a different or similar fluid.

Figure 13:
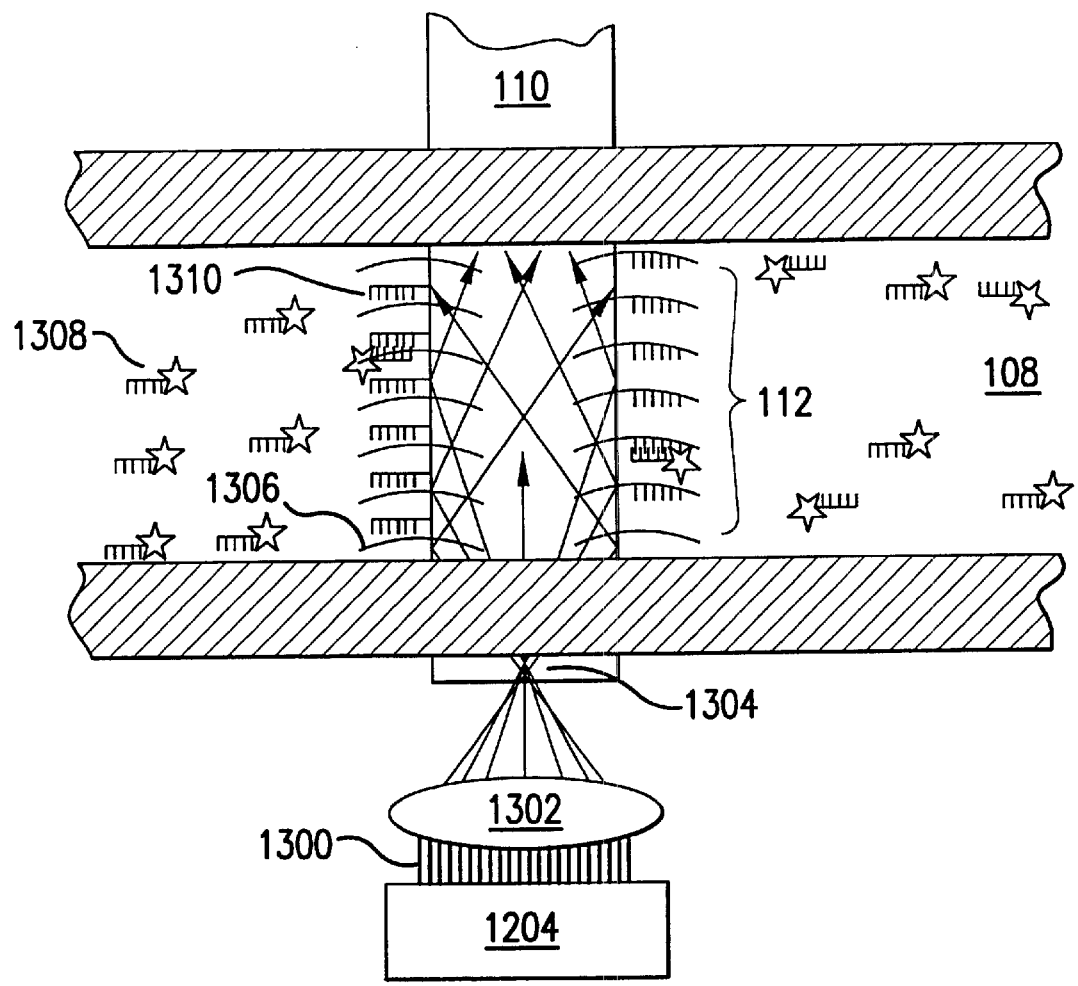
FIG. 13 is a schematic of the interface between the light source and the fiber shown in FIG. 11.

FIG. 13 is a schematic view of the interface between the light source 1204 and the fiber 110 shown in FIG. 12 once the fluid containing a chemical species has contacted the fiber 110. The light source 1204 generates light rays 1300 that are focused by a lens 1302 into an end of a given fiber 110 (or group of fibers) and that reflect internally inside of the fiber 110. A preferred lens 1302 is a cylindrical lens that forms the rays 1300 into a focal point 1304 at the end of the fiber 110. The focal point 1304 may form a plane perpendicular to the fiber 110 so that of the fiber 110 and the light source 1204 do not require exact alignment. The light reflecting inside the fiber 110 creates an evanescent wave 1306 on the surface of the fiber 110 illuminating the fiber surface. In a DNA hybridization application, the fluid containing the chemical species or sample fragment 1308 could be a DNA fragment labeled with a fluoraphore. A probe DNA fragment 1310 is attached to the fiber 110 as explained supra. If the structure of the sample fragment 1308 matches the structure of the probe DNA fragment 1310, the sample fragment 1308 will hybridize with the probe DNA fragment 1310 and remain at the fiber surface. Since the evanescent wave 1306 only illuminates near the fiber surface, the sample fragment 1308 labeled with the fluorophore will be illuminated and fluoresce if hybridized to a probe DNA fragment 1310, while mismatch DNA will not hybridize and therefore, not fluoresce, since it is not near the fiber surface. Thus, hybridization of the sample fragment 1308 to a particular probe DNA fragment 1310 is indicated by the presence of fluorescent light when a sample fragment 1308 is injected into the channel 108 and exposed to the fibers 110. If the interaction between the sample fragment 1308 and the probe DNA fragment 1310 causes an increase or decrease in the absorbance of a particular wavelength of light, the area around a contact point 112 will emit either a greater or lesser quantity of light as compared with contacts point 112 where no interaction occurred. The intensity of this evanescent wave 1306 exponentially dissipates with distance from the surface of the fiber 110 and almost disappears beyond 300 nanometers. Therefore, only the fiber 110, and the chemical species on the fiber, probe DNA fragment 1310, receiving the beam of light 1300 are illuminated. The material around the fiber 110 is not illuminated. Thus, the signal to noise ratio received by the light evaluating device or detector is improved. Because of their selective illumination, the optical fiber arrays of the invention can be advantageously used with assays where the chemical species in solution is labeled with a fluorophore without first having to remove the excess, unreacted labeled species. The labeled species only produce a detectable fluorescence signal if they interact with the chemical species immobilized on optical fiber 110; labeled species free in solution are not illuminated and do not fluoresce. Of course, where desired, the excess unlabeled chemical species can be removed prior to detection.

It should be appreciated that the wavelength of light used for illuminating the fibers will depend upon the optical absorption band of the fluorescent molecule. In addition, the light evaluating device needs to be able to detect the excitation light.

Referring to FIGS. 12 and 13, after measuring the light at a given contact point 112, or set of contact points along a given fiber 110, or set of fibers, the light evaluating device 1208 may be moved, manually or automatically, to the next contact point 112, or set of contact points along the same fiber 110, or next set of fibers. Alternatively, there may be a light evaluating device 1208 fixed at each contact point 112. Once all of the contact points 112 along a given fiber, or set of fibers, have been evaluated, the motion device 1206 may move the light source 1204 and the focusing lens 1302 to the next fiber 110, or set of fibers, such that the beam of light 1300 is aligned appropriately with the end of the next fiber 110, set of fibers. Alternatively the light evaluating device 1108 may be fixed, and the array 1102 may be moved as described supra. It should be appreciated, however, that any contact point 112, or set of contact points may be evaluated in any sequence and in any time interval. One advantage of selectively illuminating certain fibers or groups of fibers, compared to illuminating the entire plate, is a reduction in noise from fibers and contact points that are adjacent to those being evaluated by the light evaluating device 1208. This reduces the potential confusion as to which contact points 112 are being observed.

Figure 14:
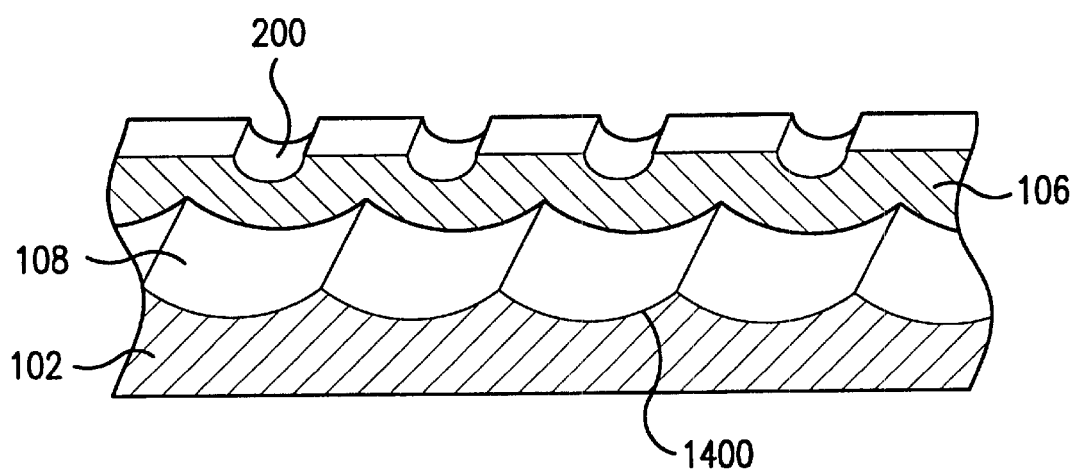
FIG. 14 is a perspective view of an embodiment of a plurality of channels used in a fiber array according to the present invention.

FIG. 14 shows a perspective view of an embodiment of a channel 108 used in a fiber array in connection with the use of a light source to illuminate the fibers 110. As shown, the bottom of the channel 108 has multiple curves positioned beneath where each fiber 110 would lay. In addition, the channel 108 may have a reflective coating 1400. The curvature of the bottom of the channel 108 and the reflective coating 1400 act to reflect the light back towards the light evaluating device to improve the strength of the light signal received from each contact point. The reflective coating 1400 may be made from any material that reflects light, such as, for example, aluminum, gold and mixtures thereof. Furthermore, the reflective coating 1400 may be multi-layered. It should be appreciated that while only one channel 108 is shown, each channel 108 may be similarly designed.

Figure 15:
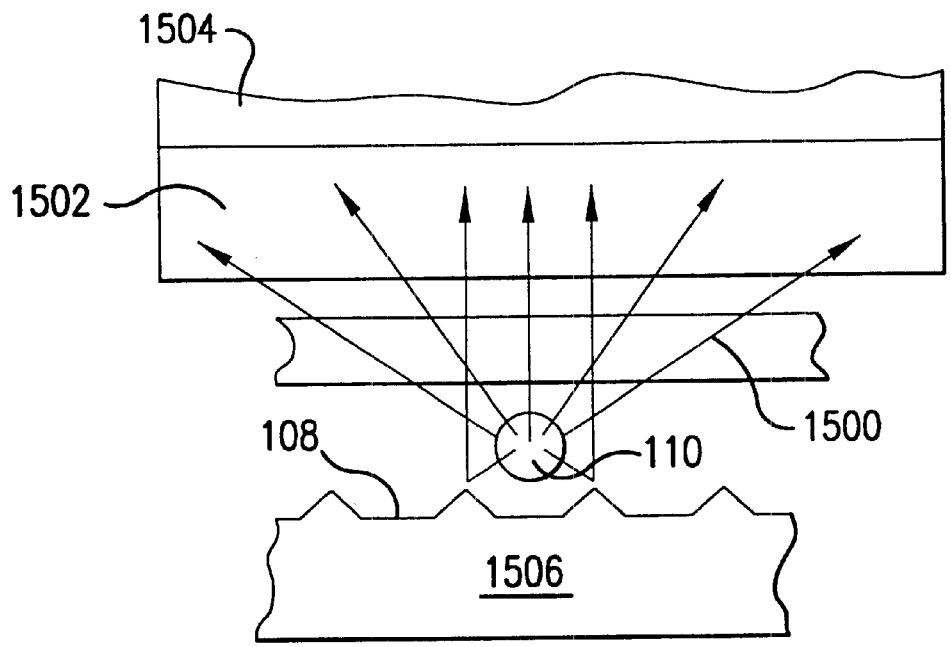
FIG. 15 is an end view of another embodiment of a plurality of channels used in a fiber array according to the present invention.
Figure 16:
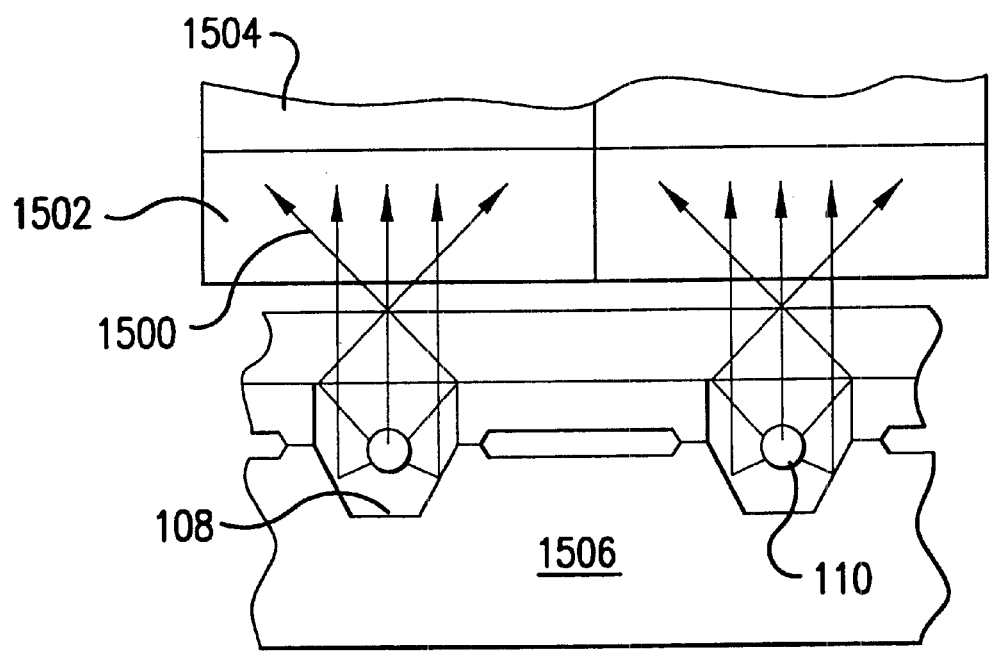
FIG. 16 is an side view of the embodiment shown in FIG. 14.

FIG. 15 is an end view of another embodiment of the channels 108 shown in FIG. 14, and FIG. 16 is a side view of the embodiment shown in FIG. 15. The amount of fluorescent light 1500 collected into the detector optic 1502 can be increased by designing the curve of the channels 108 to reflect light in a preferred direction. A preferred detector optic 1502 is a fiber optic with a much larger diameter than the fiber 110. The detector optic 1502 directs the collected light into a-photo-detector 1504, producing an electrical signal that is proportional to amount of light 1500. The preferred photo-detector 1504 is a solid-state diode or a photo multiplier tube. The channel curving can be in all dimensions, and the reflection efficiency may vary, but the general intent is to redirect light into the detector optic 1502 that would otherwise be lost into the channel substrate 1506.

Figure 17:
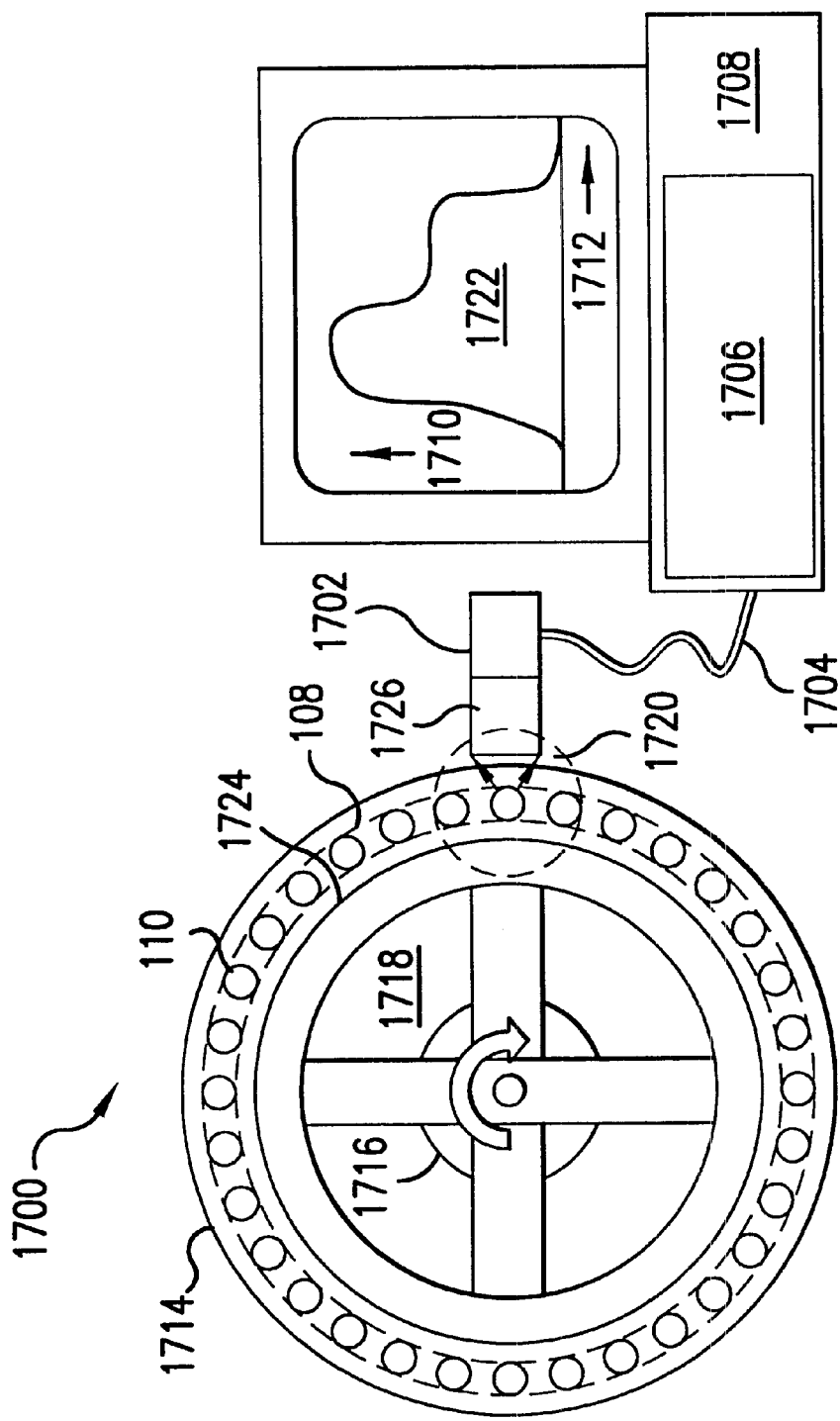
FIG. 17 is another embodiment of a fiber array reader according to the present invention.

FIG. 17 is another embodiment of a fiber array reader 1700. An electrical signal is sent from a photo-detector 1702 through a cable 1704 to an analog to digital converter 1706 where a digital signal is generated for interpretation and plotting by a computer 1708. For example, the signal data 1722 could be plotted as intensity 1710 over time 1712. The fiber array 1714 can be arranged in a circular arrangement as shown to allow for continuous reading of the fibers 110. A motor 1716 rotates a hub 1718, supporting the fiber array 1714, at some specified rate, such as for example one revolution per second. A laser 1720 is fixed such that the light from laser 1720 forms a focused line at the fiber-end, as discussed supra. In other words, the fibers 110 are sequentially rotated into the focused line of laser light. Because the laser line or plane is much narrower than the spacing between the fiber's 110 diameters, the fibers need not be accurately placed along that line for the light to enter the fiber. Furthermore, the fibers need not be accurately aligned in the orthogonal dimension either, as the fibers 110 are guaranteed to rotate into a fixed line of light.

A heater/cooler 1724 uniformly controls the temperature of the fiber array 1714. The signal from each fiber 110 is analyzed each rotation of the hub 1718 and a plot for each fiber mix-point is generated independent of any other fiber. Furthermore, the temperature is ramped over a range guaranteed to pass though the optimum temperature for binding of a mobile and an immobilized chemical species. The optimum temperature for DNA hybridization is the optimum hybridization temperature for that particular probe, as each probe has a different optimum hybridization temperature. Thus, each probe is observed at its optimum hybridization even though each probe in the fiber array 1714 has a different optimum hybridization temperature.

Figure 18:
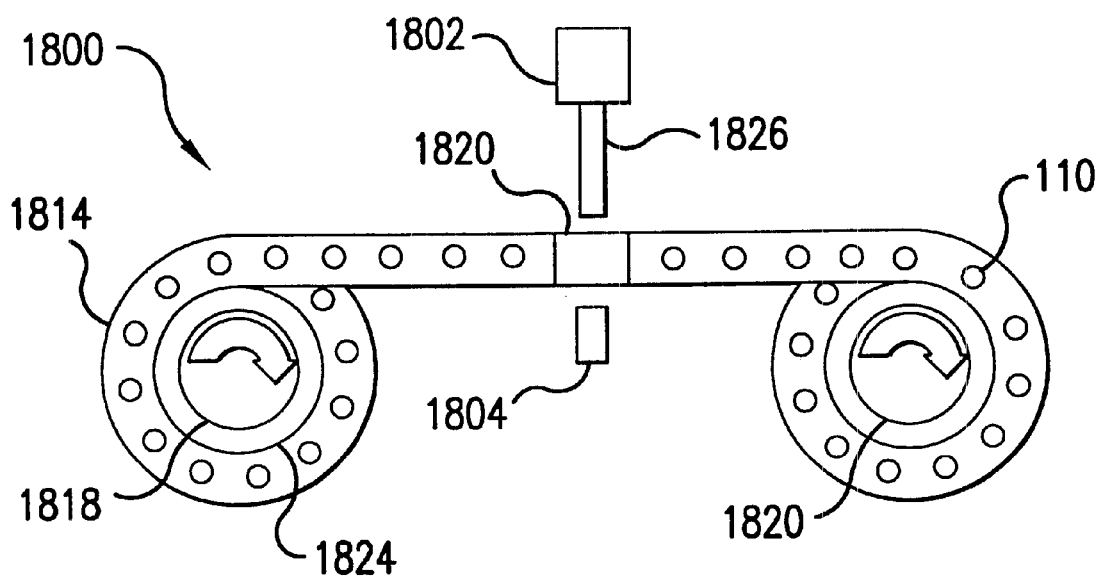
FIG. 18 is yet another embodiment of a fiber array reader according to the present invention.

FIG. 18 shows yet another embodiment of a fiber array reader 1800. In the case of very long fiber arrays 1814, the fiber array 1814 can be rolled into a format similar to a typical audio-cassette tape. In this configuration, one or more motors (not shown) move the array off one hub 1818 and onto another hub 1820 with each fiber 110 passing under a fixed detector optic 1826. Heater/cooler units 1824 may be provided in both hubs 1818 and 1820. A laser 1870 is also provided. An ultrasonic mixing device 1804, preferably fixed in space, may be added to improve mixing of the fluids.

Figure 19:
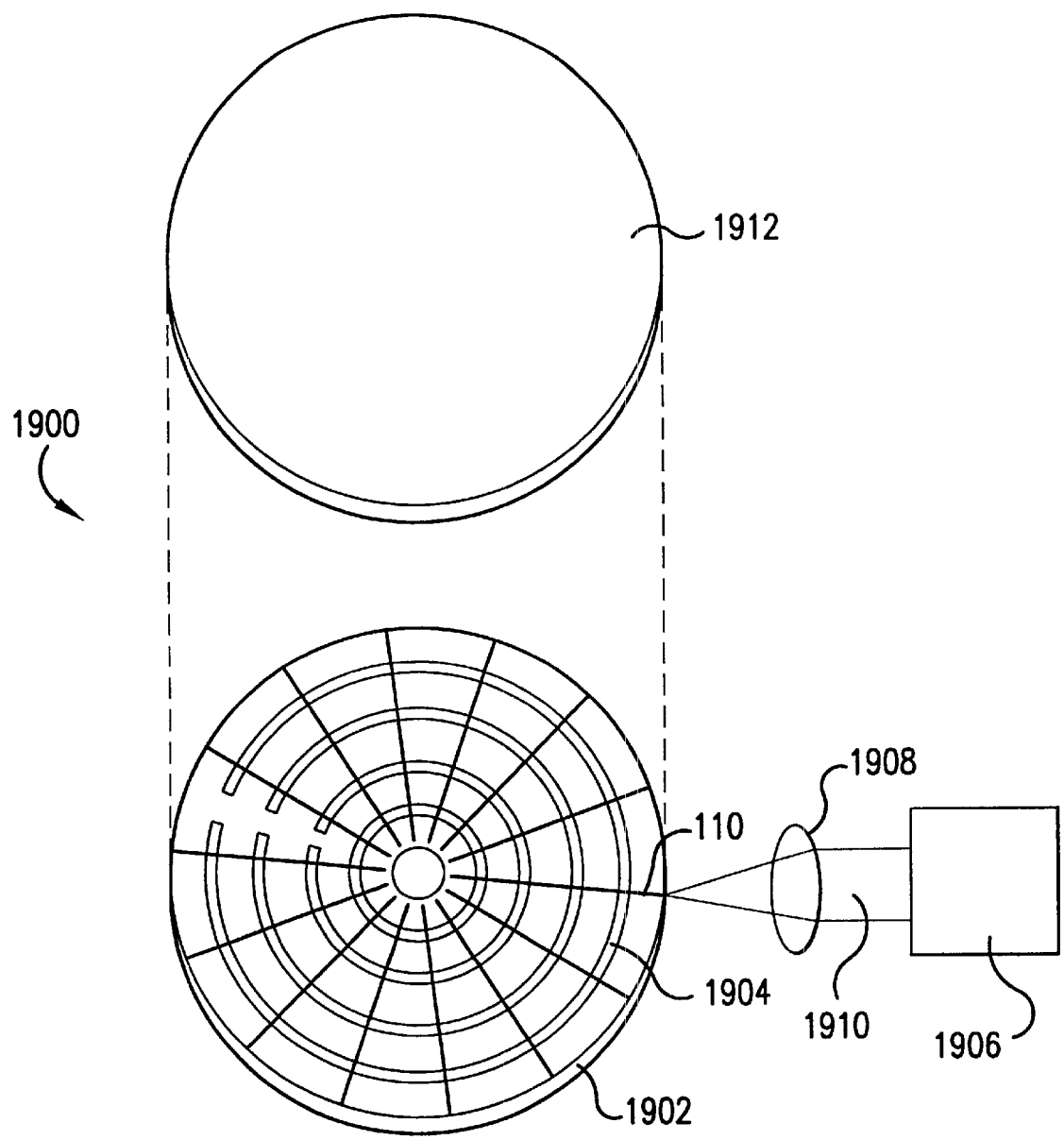
FIG. 19 is another embodiment of a fiber array according to the present invention.

FIG. 19 is still another embodiment of a fiber array according to the present invention. The fiber array 1900 comprises a circular support plate 1902 with the fibers 110 radially disposed on the support plate 1902 such that one end of each fiber 110 is near the center of the support plate 1902 and the other end of the fiber 110 is near the outer perimeter of the support plate 1902. The fiber array 1900 also comprises a plurality of channels 1904 in the support plate 1902. Although the channels 1904 may be arranged in any fashion or pattern on the support plate 1902, preferably, the channels 1904 are arranged in concentric circles; however, it should be appreciated that it is not necessary to have a channel which traverses an entire concentric circle. For example, a channel 1904 may simply be the length of a portion of a concentric circle or an arc. The light source 1906 and focusing lens 1908 act to project and direct the beam of light 1910 to the end of each of the fibers 110. In this embodiment, rather than move the light source 1906 and the focusing lens 1908 to align the beam of light 1910 with each fiber 110, the support plate 1902 is rotated such that each fiber 110 is aligned with the beam of light 1910. Again, a motion detection system (not shown) having motion sensors may be used to monitor the exact positioning of the support plate 1902 to provide exact alignment with the beam of light 1910. A cover 1912 may also be provided.

No image is necessary for the various readers, so a single diode may collect the information. The signal from this diode can be quickly converted from analog to digital and recorded, reducing the amount of data as compared to a camera system. Since the detection system is simple and inexpensive, it is feasible to detect many channels simultaneously, greatly increasing the throughput.

Furthermore, because the evanescence wave does not travel far beyond the fiber surface, the sample can remain in the channel during hybridization, avoiding washing and allowing real-time reading. Thus, the fluorescent signal can be monitored while temperature is ramped. Rather than a snap-shot information, information on hybridization over time is collected, providing much higher specificity and real time monitoring.

The fiber arrays may contain 100,000 or more fibers that could be quickly detected by these readers and many channels may be read simultaneously, resulting in a high density of information.

The light-source may also directly illuminate the mix points through the fiber to reduce stray light and unwanted reflections. Thus, reducing the noise level. In a desirable contrast, the signal level is higher because the cylindrical shape of the fiber focuses fluorescence rays passing through it. This focusing results in the collection of fluorescence rays that otherwise would be lost.

Furthermore, only the fibers are illuminated, avoiding the wasteful process of flood illuminating the entire surface area, and thus, reducing the amount of illumination power needed.

Any of the above reader embodiments may include an adaptive filter to filter out common noise such as reflecting light. To calibrate the system all detectors are activated when no chemical species is present. All detectors are then set to zero using mathematical manipulation such as a transfer function. The chemical species is then added to the system. Any change in signal from the detectors is therefore caused by the added chemicals species.

Figure 27:
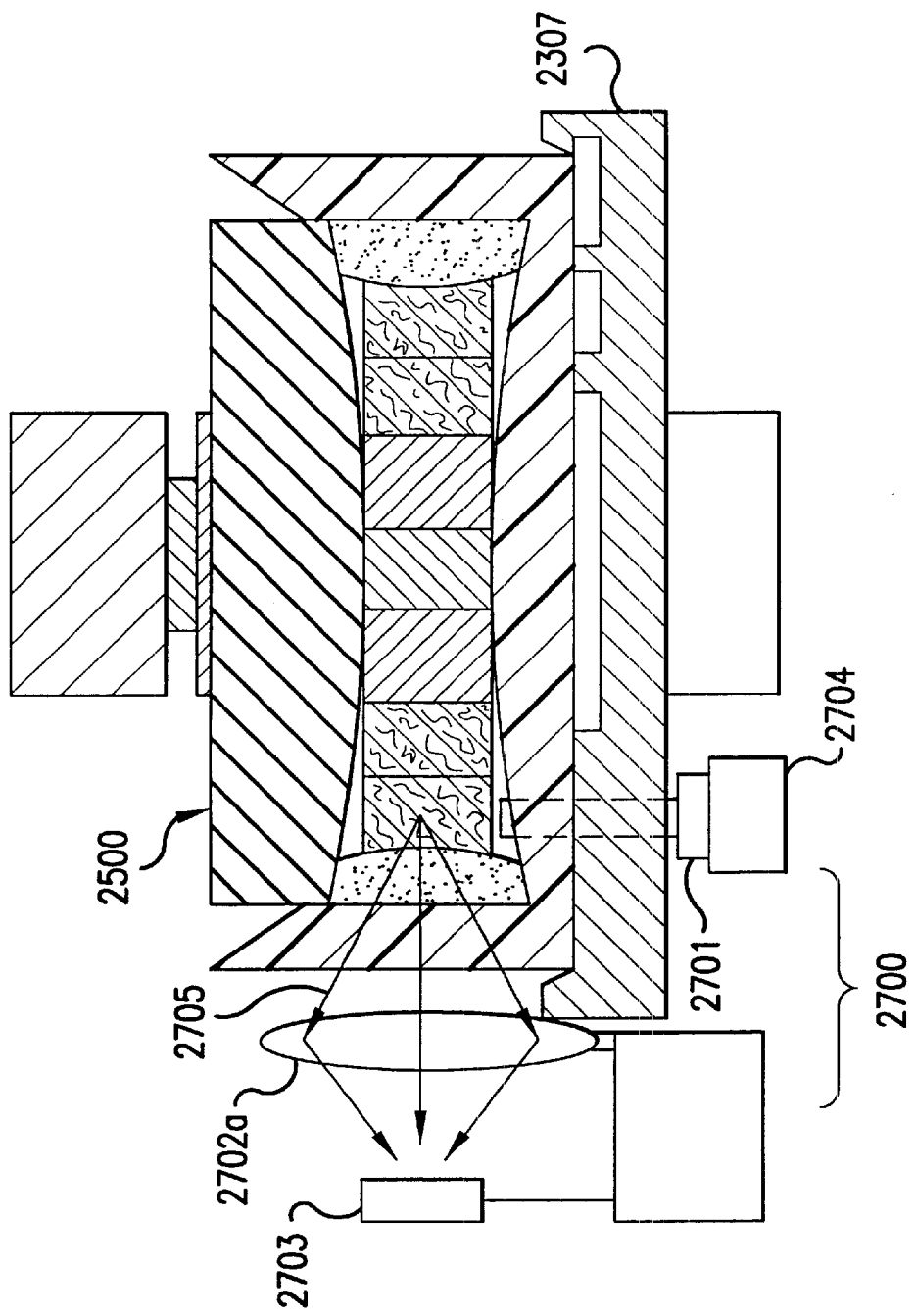
FIG. 27 is a light evaluating system according to one embodiment of the present invention.
Figure 28:
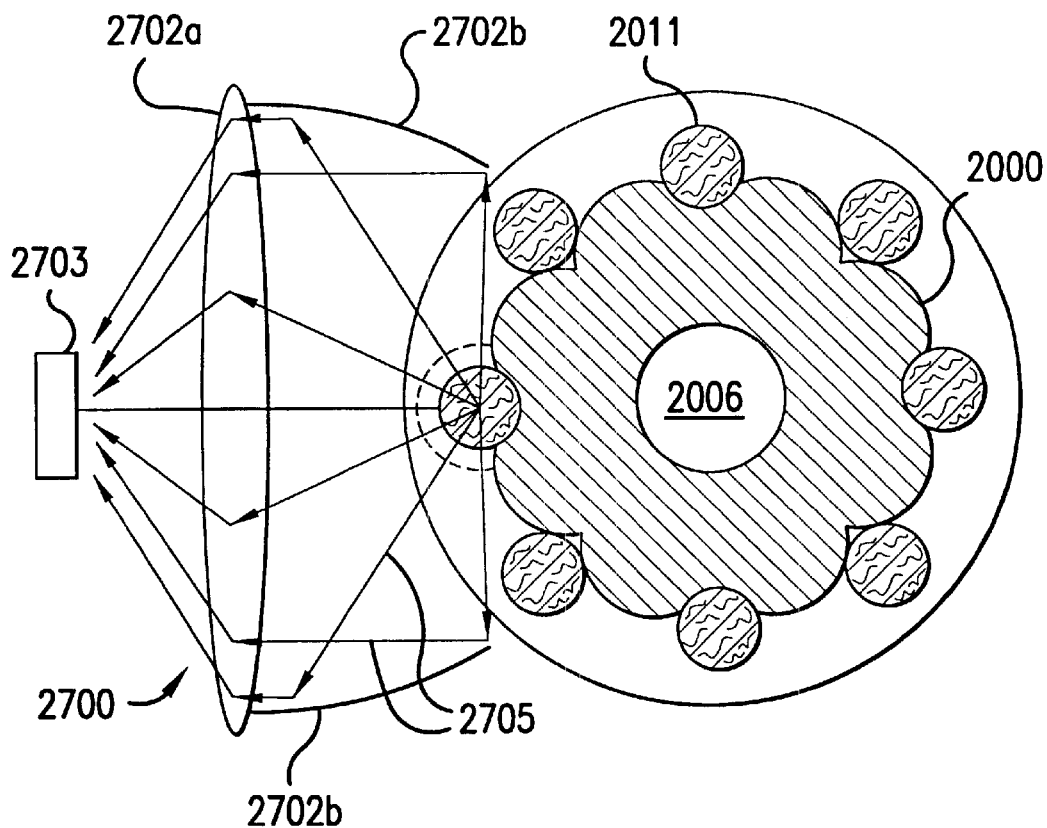
FIG. 28 is another embodiment of the light evaluating system of FIG. 27.
Figure 29:
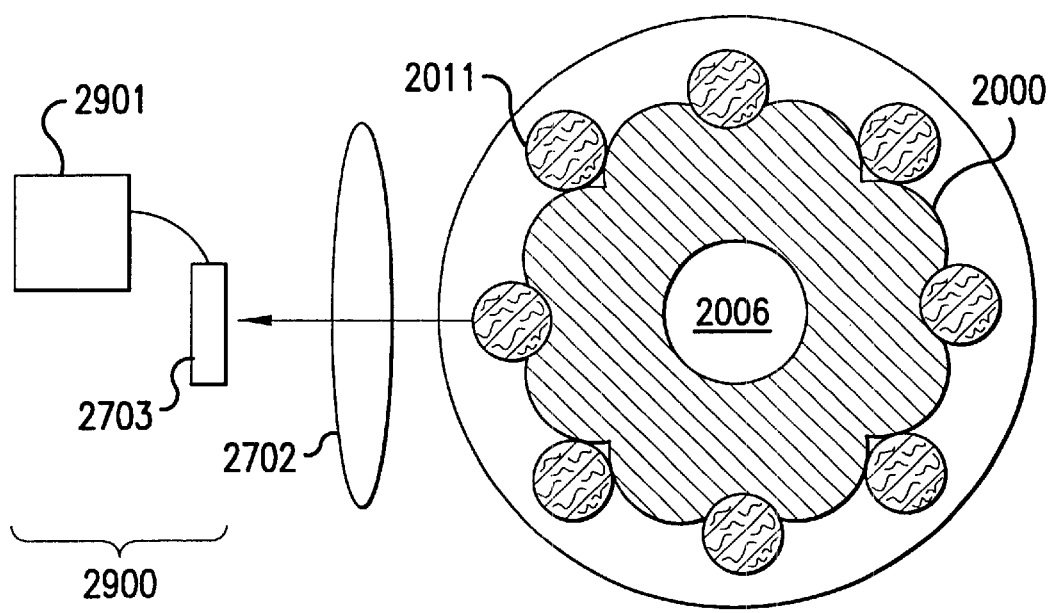
FIG. 29 is yet another embodiment of a light evaluating system according to the present invention.

In yet another aspect of the invention, the fibers 110, which have been described above, are incorporated into a fiber wheel mixing system for contacting at least two chemical species. It should be appreciated that the fiber wheel mixing system may be used for any of the chemical interactions described previously in connection with the fiber array. The fiber wheel mixing system generally includes a container for receiving a mobile chemical species and a wheel including fibers having a chemical species immobilized thereon. FIGS. 20 through 26 and 30 and 31 show various embodiments of the fiber wheel mixing system. FIGS. 27 to 29 show various embodiments of a light evaluating system for detecting and evaluating light signals generated as a result of mixing between two chemical species.

Figure 20:
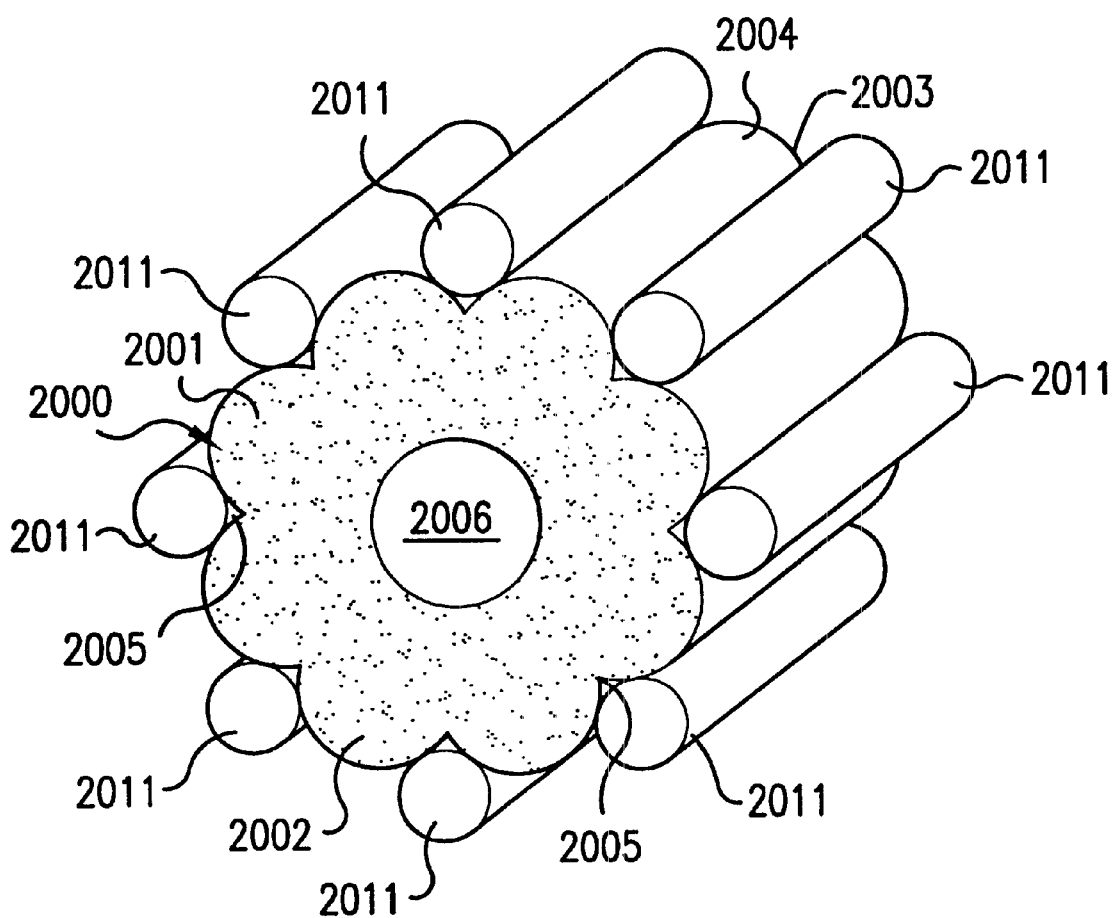
FIG. 20 is a perspective view of a wheel according to one embodiment of the present invention.

FIG. 20 is a perspective view of a wheel 2000 having a plurality of fibers 2011 each of which has a chemical species immobilized thereon. The wheel 2000 has a top 2002, a bottom 2003, a perimeter sidewall 2004, and a longitudinal axis (not shown) that runs through a center wheel aperture 2006 in a direction parallel to the fibers 2011. Although the wheel 2000 may be shaped and sized to have any desired diameter and height, it is preferred to have an aspect ratio greater than 1.0, where the aspect ratio is defined as a ratio of the wheel diameter to the wheel height (i.e., the vertical distance between the top 2002 and the bottom 2003 of the wheel 2000). The size of the wheel 2000 may be adjusted in order to accommodate the desired number of fibers 2011 to be disposed thereon and the pre-determined spacing therebetween. For example, a wheel having a diameter of about 63 mm can accommodate on its sidewall up to 1,000 fibers (200 $\mu$m or less in diameter) while maintaining 200 $\mu$m of center-to-center distance between the adjacent fibers. The wheel diameter may range from 5 to 10 cm, although greater or less wheel diameters may be preferred depending on the number of fibers 2011 to be disposed and desirable spacing therebetween. The wheel 2000 may also include the center wheel aperture 2006 for handling purposes which will be discussed in greater detail below.

Still referring to FIG. 20, a plurality of the fibers 2011 are disposed on the perimeter sidewall 2004 of the wheel 2000 via mechanical and/or chemical bonding. The fibers 2011 are preferably aligned parallel to each other and in a direction parallel to the longitudinal axis of the wheel 2000. The fibers 2011 may also be arranged to maintain a uniform spacing therebetween. The sidewall 2004 may include a plurality of grooves 2005, each of which extends from the top 2002 and terminates at the bottom 2003 of the wheel 2000. The grooves 2005 are shaped and sized to receive the fibers 2011 and to facilitate the alignment of the fibers 2011. The grooves 2005 may also be shaped to retain the fibers 2011. In addition, it should be appreciated that the grooves may being optically curvatious to reflect the light into the detectors in a manner which promotes optimum collection efficiency. It should be appreciated that any geometic curvature of the grooves may be used to reflect light to the detectors.

Figure 21:
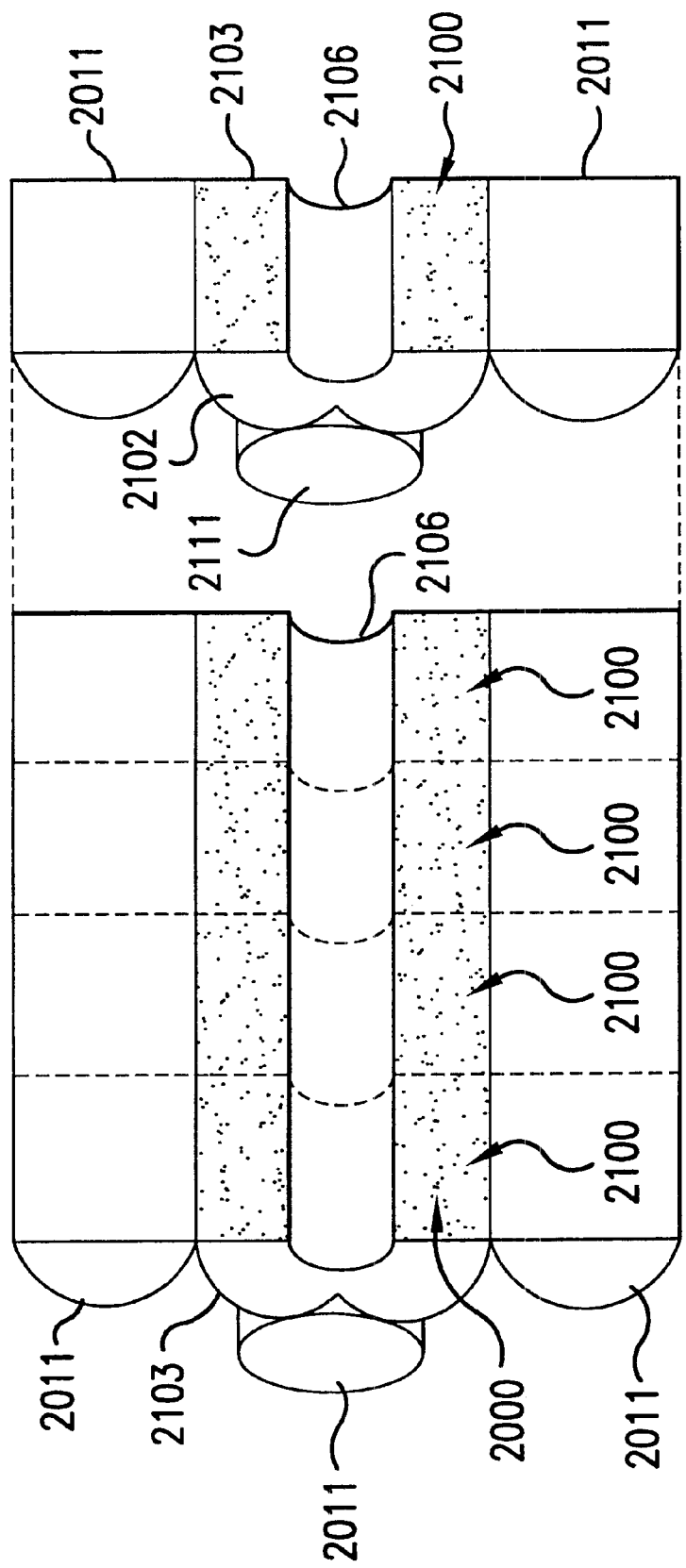
FIG. 21 is a perspective view of a cylinder according to one embodiment of the present invention.

FIG. 21 is a perspective view of a cylinder 2100 having a plurality of fibers 2011 each having immobilized thereon a chemical species. The cylinder 2100 preferably has a length much greater than its diameter such that the fibers 2011 can be of any desired length along a surface 2103 of the cylinder 2100. For example, the fibers 2011 may be 5 to 10 centimeters in length on the surface 2103 of the cylinder 2100 which may have a diameter of about 63 mm. The cylinder 2100 may include a center cylinder aperture 2106 for ease of handling. Once disposed with the fibers 2011, the cylinder 2100 may be pre-cut and/or pre-perforated at pre-described lengths in order to pre-form a plurality of wheels 2000 readily separable in a direction perpendicular to a longitudinal axis of the cylinder 2100. It should be appreciated that the cylinder may be comprised of separate wheels that are connected using a fastener, such as a snap, or adhesive, such as glue or tape, so that after the fibers are placed on the cylinder, the wheel may be easily separated. The wheel 2000 having a predescribed height can then be prepared by separating an end wheel unit 2000 from the rest of the cylinder 2100, for example, by applying mechanical force, such as a knife or water jet, heat, such as laser cutting, or by other separation methods known in the art. One or more wheels 2000 can be separated from the cylinder 2100 with care taken not to contaminate the chemical species from one fiber onto another. Wheels 2000 and cylinders 2100 may be made of a materials similar to that of the fiber array. The surface of the wheel 2000 and the cylinder 2100 may also be provided with features such as low-fluorescence or a reflective coating, for example, the cylinder may be made of plastic having a vapor deposited gold coating.

Figure 22:
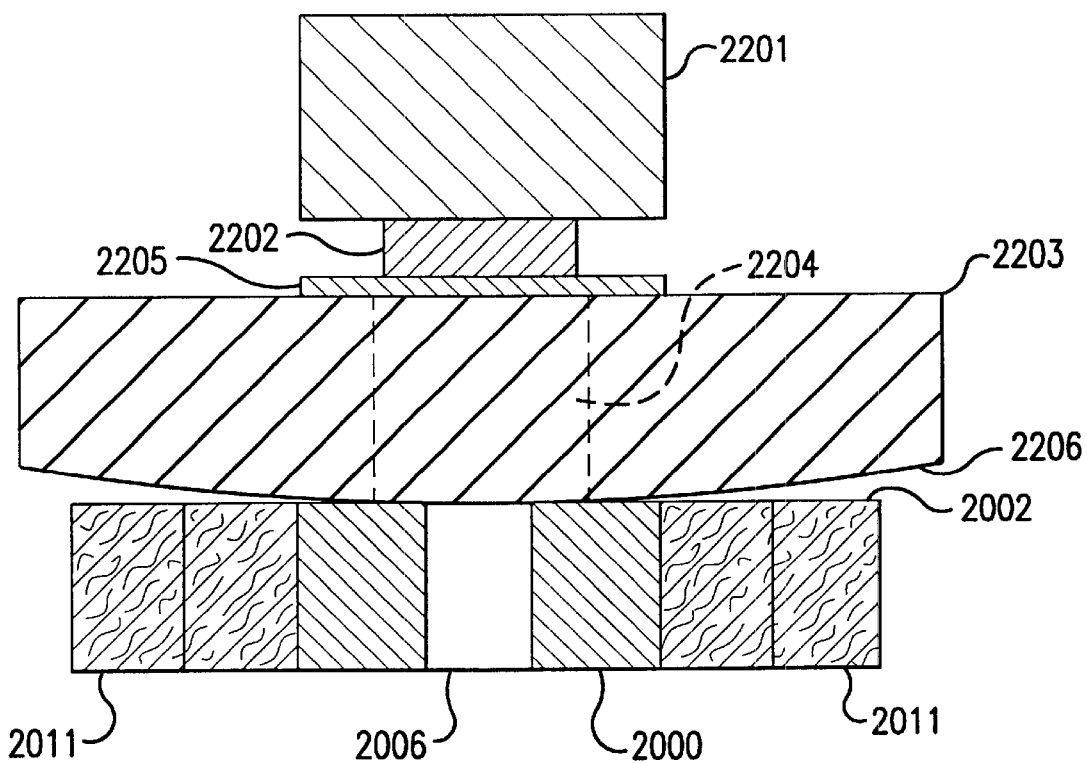
FIG. 22 is a cross-sectional view of a wheel coupled to a wheel rotation device according to one embodiment of the present invention.

FIG. 22 is a cross-sectional view of a wheel 2000 coupled to a wheel rotation device 2201 through a rotational coupler, such as an axle 2202 positioned therebetween. By coupling one end of the axle 2202 to the wheel rotation device 2201 and by fixedly coupling the other end of the axle 2202 to the wheel 2000 through its center wheel aperture 2006, the wheel 2000 can be rotated by the wheel rotation device 2201, such as an electric motor, a manual rotation assembly, or other rotation devices known in the art. A sealing disk 2203 may be positioned between the wheel 2000 and the wheel rotation device 2201. The disk 2203 is preferably shaped and sized according to the dimension of the container such that the disk 2203 may serve as a cover plate that sealingly engages the container, as will be described later. The disk 2203 is loosely constrained by the axle 2202 which passes through a center disk aperture 2204. A bottom surface of the disk 2203 may be shaped to be concave toward the top 2002 of the wheel 2000 in order to minimize rotational friction therebetween. A lock washer 2205 may also be provided on top of the disk 2203 and arranged to lightly press both the wheel 2000 and the disk 2203 downwardly. It should be appreciated that the axle 2202 is only one example of the rotational coupler that may be used to couple the wheel 2000 to the wheel rotation device 2201. For example, a cylinder 2100 and a wheel 2000 may be fabricated without any center apertures 2006, 2106 therein. One of skill in the art would recognize that such wheels 2000 without center wheel aperture 2006 can be coupled to and rotated by the wheel rotation device 2201 using other rotational couplers such as a vacuum chuck, magnet, and other rotatable coupling elements known in the art.

Figure 23:
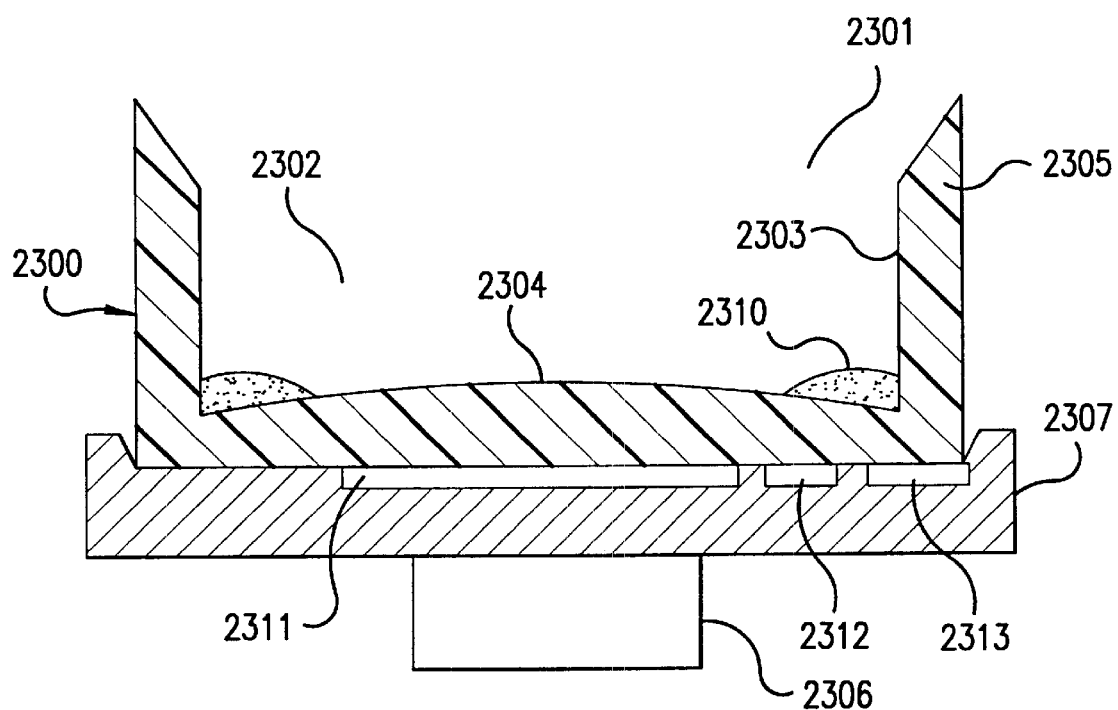
FIG. 23 is a cross-sectional view of a container coupled to a container rotation device according to one embodiment of the present invention.
Figure 25:
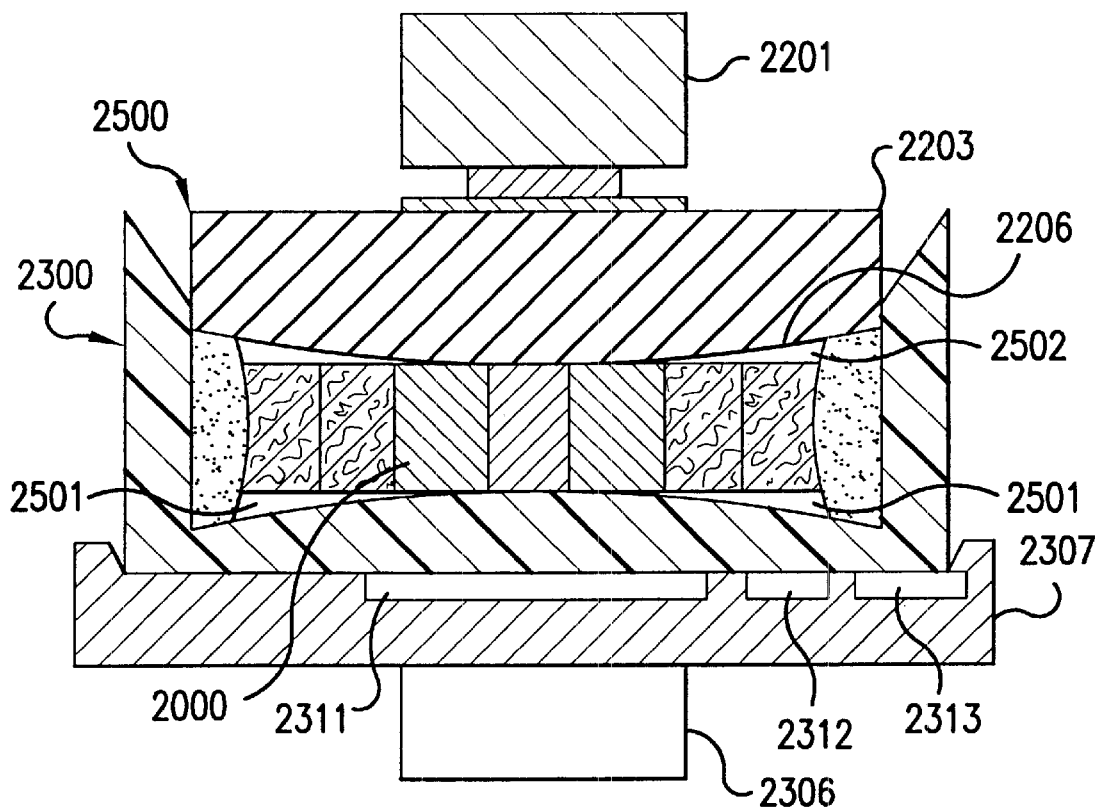
FIG. 25 is a cross-sectional view of a fiber wheel mixing system according to one embodiment of the present invention.

FIG. 23 is a cross-sectional view of a container 2300 coupled to a container rotation device 2306. The container 2300 is capable of receiving and storing the mobile chemical species therein and receiving at least a portion of the perimeter sidewall 2004 of the wheel 2000. The container 2300 is preferably an open cylinder having a top opening 2301, a cavity 2302, and container sidewalls 2305. The cavity 2302 is defined by a cavity sidewall 2303 and a cavity bottom surface 2304. Because the container 2300 is to receive the wheel 2000 therein, the configuration of the container 2300 is determined by the shape and size of the wheel 2000. In addition, the container 2300 is also arranged to form an annular chamber gap with pre-described dimensions between the cavity sidewall 2303 and the perimeter sidewall 2004 of the wheel 2000 (the chamber gap is shown in FIG. 25, i.e., an annular ring-shaped space that upon rotation will be filled with the mobile chemical species 2310). The chamber gap generally has a thickness less than a few centimeters and preferably within the range of 0.5 to 1.5 mm. The cavity bottom surface 2304 may be shaped to be concave upward to minimize rotational friction against the bottom 2003 of the wheel 2000 and to preferentially displace the mobile chemical species 2310 toward the cavity sidewall 2303. The container 2300 is generally made of inert material and preferably of low cost material so that it can be disposed after use. The container sidewall 2305 and/or cavity sidewall 2303 may be made of flexible material similar to that of the fiber arrays. It should be appreciated that the container may generally be made of materials the same as or similar to the fiber arrays.

Still referring to FIG. 23, the container 2300 is mechanically coupled to the container rotation device 2306 through a platform 2307 positioned therebetween. A top surface of the platform 2307 is shaped and sized to receive the container 2300 such that the container rotation device 2306 can rotate the platform 2307 along with the container 2300. The platform 2307 may include a heating element 2311, a temperature sensor 2312 or a temperature controller 2313 for heating the fluid stored in the container 2300 and controlling the temperature thereof.

Figure 24:
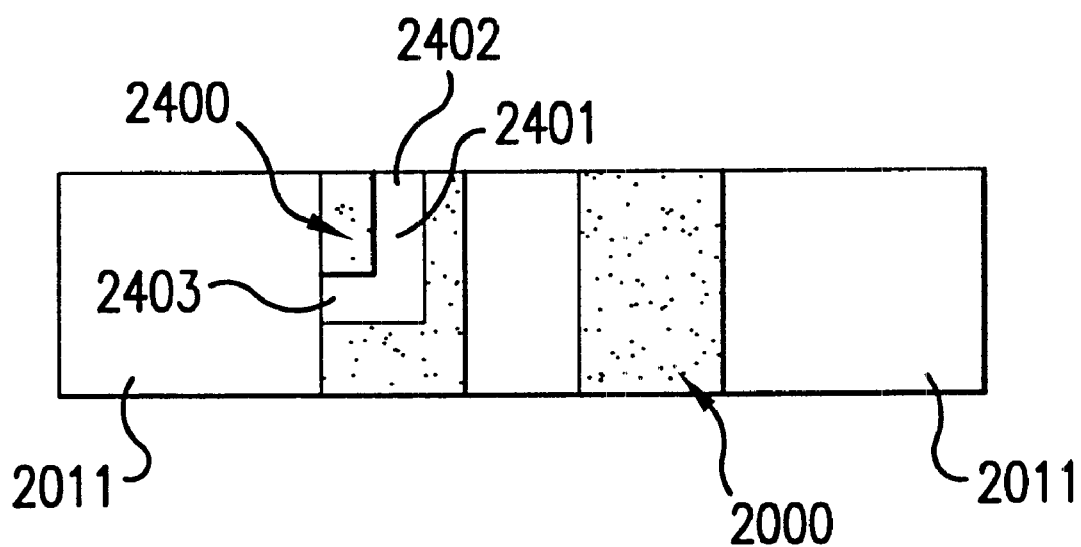
FIG. 24 is a cross-sectional view of a fluid delivery system according to one embodiment of the present invention.

FIG. 24 is a cross-sectional view of a fluid delivery system 2400 according to the present invention. In general, a fluid pathway 2401 is embedded inside the wheel 2000 and terminates at one or more inlet ports 2402 and outlet ports 2403. The mobile chemical species is loaded through the inlet port 2402, moves through the fluid pathway 2401 toward the outlet port 2403, and is discharged into the chamber gap (shown in FIG. 25) formed between the cavity sidewall 2303 and the perimeter sidewall 2004 of the wheel 2000. Gravity, capillary force, centrifugal force, and/or electomotive force may be used as the driving force for moving the mobile chemical species through the fluid pathway 2401. A filter (not shown) may be provided at the inlet and/or outlet ports 2402, 2403, or along the fluid pathway 2401 in order to remove undesirable substances from the mobile chemical species. Filtration may be accomplished by adsorption, absorption, filtration or other filtering mechanisms known in the art.

Figure 26:
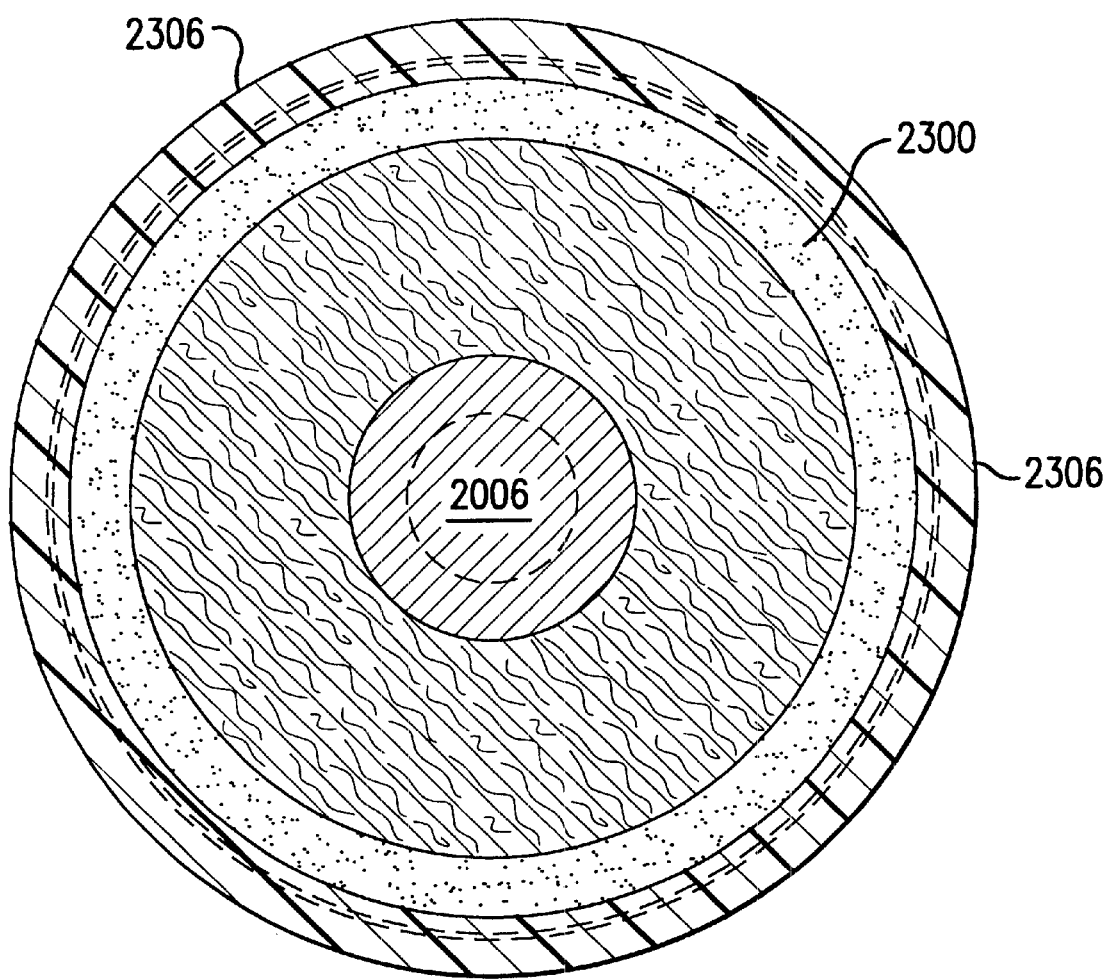
FIG. 26 is a top plan view of the fiber wheel mixing system of FIG. 25.

FIGS. 25 and 26 are a cross-sectional view and a top-plan view of a fiber wheel mixing system 2500, respectively. In operation, the mobile chemical species 2310 is loaded into the cavity 2302 of the container 2300 by the fluid delivery system 2400 described above (shown in FIG. 31). Alternatively, the mobile chemical species 2310 may be directly loaded into the container cavity 2302 with a syringe or pipette or by other manual or automated means. As illustrated in FIGS. 25 and 26, the fiber wheel mixing system 2500 is assembled by positioning the wheel 2000 inside the container cavity 2302, by fitting the disk 2203 onto the top opening 2301 of the container 2300, by sealingly engaging the disk 2203 around the top opening 2301, and by forming a closed space for containing the mobile chemical species 2310. The wheel 2000 and the container 2300 are rotated by the corresponding rotation devices 2201, 2306. The speed and duration of the rotation may vary depending on the chemical reaction rates and may range from seconds to hours. The mobile chemical species 2310 is then displaced toward the cavity sidewall 2303 by the centrifugal force, and forms an annular column of fluid 2310. In general, the thickness of the fluid column is determined by several factors such as the cavity diameter, cavity height, chamber gap dimension, and the amount of the mobile chemical species 2310 loaded into the container cavity 2302. By filling the chamber gap with a pre-described amount of the mobile chemical species 2310, the chemical species immobilized on the fibers 2011 of the wheel 2000 can contact the mobile chemical species 2310.

It is appreciated that the wheel 2000 and the container 2300 are preferably counter-rotated at a speed enough to generate a turbulent mixing zone at the mix points. The turbulent mixing increases the contact efficiency and minimizes the amount of the chemical species required for efficient mixing therebetween. Rotational speeds necessary to form the turbulent mixing zone can be easily determined and confirmed by introducing an indicator or dye into the mixing zone and observing the mixing pattern therein, or by analyzing the intensity of the light signals emanating from the fibers 2011 which will be discussed in greater detail below. One of skill in the art would recognize that rotating only one of the wheel 2000 or the container 2300 can also generate a similar turbulent mixing zone.

Clearances 2501, 2502 may be provided at the contacting zones between the disk 2203 and the wheel 2000, and between the wheel 2000 and the cavity bottom surface 2304. These clearances 2501, 2502 minimize the rotational friction and may serve as an additional fluid channel through which the mobile chemical species 2310 can be displaced during rotation from a cavity center toward the cavity sidewall 2303.

FIGS. 27 and 28 show two embodiments of a light evaluating system 2700 for detecting light signals generated as a result of mixing two or more chemical species. The light evaluating system 2700 typically includes a light source 2701, light guiding devices 2702ba, 2702b, and a light detecting device 2703. The light source 2701, such as a laser or an arc lamp, produces a beam of light 2705 with the desired wavelength that is directed to one end of the fiber 2711. Appropriate light source 2701 and desired wavelength of the light can be selected by methods similar to those described above in connection with the fiber array 100. For purposes of the present invention, the fibers 2011 are preferably optical fibers, details of which have already been described above. The light source 2701 is located under the platform 2307 such that the light beam 2705 is directed to the end of the fiber 2011 and internally reflects therein. The reflected light beam 2705 creates an evanescent wave on a surface of the fiber 2011 illuminating the chemical species attached thereto. Because the intensity of the evanescent wave exponentially dissipates with distance from the surface of the fiber 2011 (almost disappearing beyond 300 nm), the chemical species is illuminated but not the material surrounding the fiber 2011, i.e., only the fiber 2011 fluoresces. More specifically and as described above, only those locations along each fiber 2011 where some type of interaction between the chemical species has occurred will produce a detectable signal such as fluorescence. The light guiding device such as a focusing lens 2702a and a reflecting mirror 2702b may be used to collect photons generated by fluorescence from the fibers 2011 and to focus the photons into the light detecting device 2703. Examples of such light guiding devices include, but are not limited to, lenses, mirrors, prisms, and other optical elements known in the art. The light guiding device 2702a, 2702b as well as optional reflective coating on the perimeter sidewall 2704 of the wheel 2000 directs more photons into the light detecting device 2703, thereby improving the signal-to-noise ratio of the detected light signals.

In operation, after measuring the light signal at a given mix point or along a given fiber 2711, the wheel 2000 is sequentially rotated either manually or automatically. The rotation places a new mix point and/or a new fiber into the field of the light evaluating system 2700 and aligns the light beam 2705 into an end of the new fiber. It is appreciated that an optional light guiding device may be positioned between the light source 2701 and the platform 2307 to focus the light beam 2705 on the end of the fiber 2011. An optional motion device 2704 may be used to move the light source 2701 and/or the light guiding devices 2702a, 2702b along a perimeter of the wheel 2000 to properly align the light beam 2705 with the end of each fiber 2011. In addition, an optional motion detecting system with motion sensors (not shown), such as infrared light sensors, may be used to monitor the position of the motion device 2704.

FIG. 29 shows another embodiment of a light evaluating system 2900. The photons collected into the light detecting device 2703 generate electric current in proportion to the number of photons detected. This electrical signal is amplified, processed, and plotted over time by an electrical device 2901, e.g., an oscilloscope or computer. As described above, after measuring the light signal at a given mix point or along a given fiber 2011, the wheel 2000 is sequentially rotated and a new mix point or a new fiber is brought into the field of the light evaluating system 2900. The light beam 2705 is aligned into an end of the new fiber and the above procedures are repeated.

Figure 30:
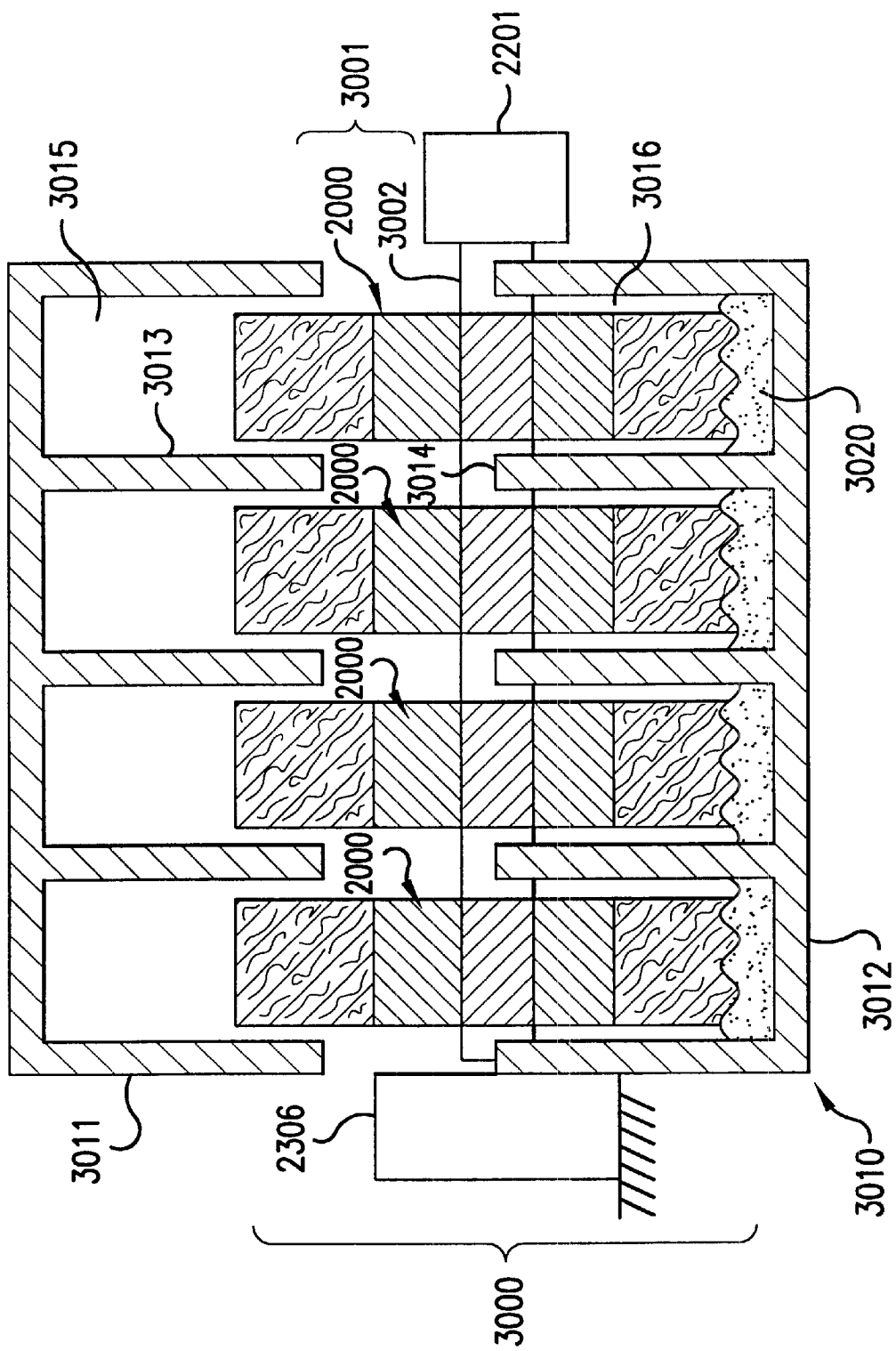
FIG. 30 is a cross-sectional view of another embodiment of a fiber wheel mixing system including a wheel assembly and a multi-cavity container according to the present invention.
Figure 31:
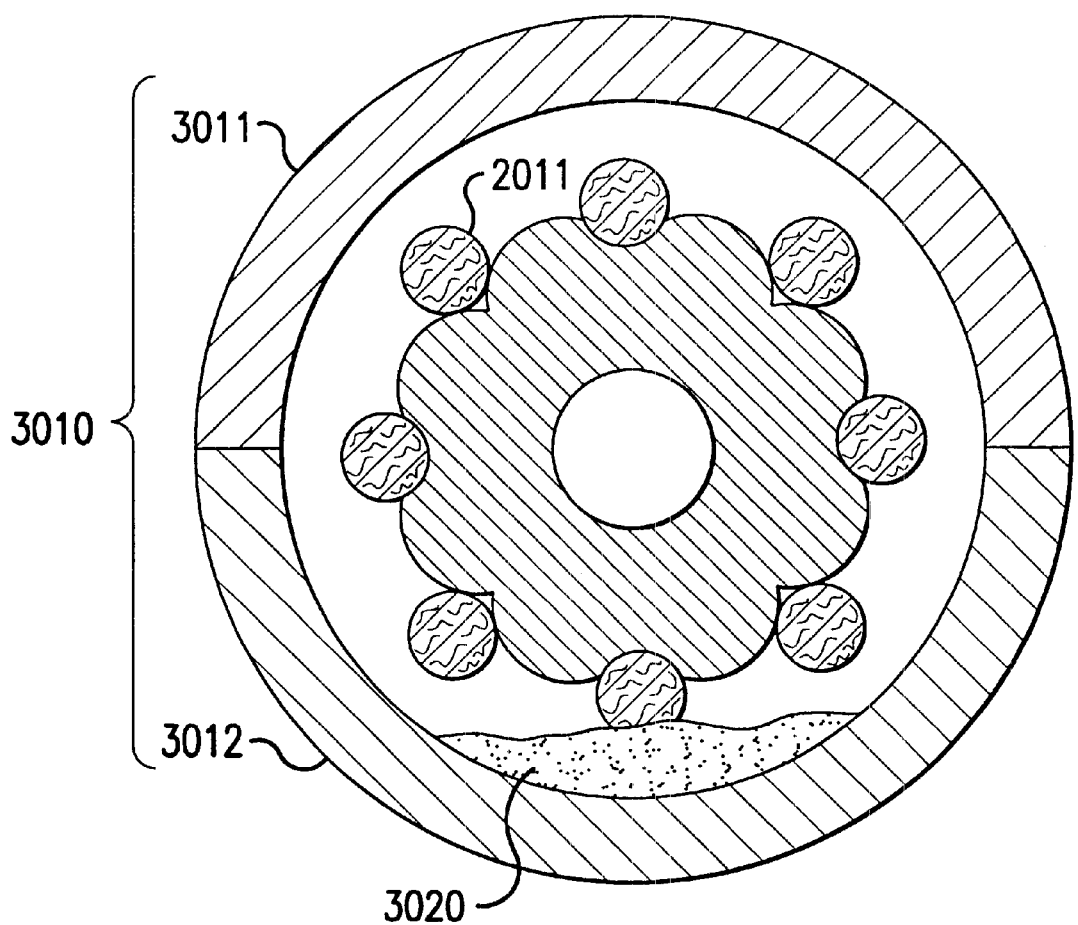
FIG. 31 is another cross-sectional view of the fiber wheel mixing system of FIG. 30.

FIGS. 30 and 31 illustrate another embodiment of a fiber wheel mixing system 3000 including a wheel assembly 3001 and a multi-cavity container 3010. FIG. 30 is a cross-sectional view of the system 3000 along a rotational coupler, such as a rotation axle 3002. FIG. 31 is a cross-sectional view of the system 3000 in a direction perpendicular to the rotation axle 3002 of FIG. 30. The wheel assembly 3001 includes multiple wheels 2000 vertically positioned along the rotation axle 3002 through their center wheel apertures 2006, and is rotatably coupled to the wheel rotation device 2201. The multi-cavity container 3010 consists of a top portion 3011 and a bottom portion 3012, and each of top and bottom portions 3011, 3012 includes top and bottom dividers 3013, 3014, respectively. The top portion 3011 and top dividers 3013 are arranged to fit over the bottom portion 3012 and corresponding bottom dividers 3014 such that multiple cavities 3015 form within the container 3010. The multi-cavity container 3010 may also be rotatably coupled to the container rotation device 2306.

In operation, the wheel assembly 3001 is assembled and positioned inside the bottom portion 3012 of the multi-cavity container 3010 such that about a lower half of each wheel 2000 is received by a corresponding cavity 3015 of the bottom portion 3012. The top portion 3011 is then sealingly engaged over the bottom portion 3012, and each cavity 3015 sealingly separates a corresponding wheel 2000 from its neighbors. The mobile chemical species 3010 is loaded into each cavity 3015 either directly with a syringe or pipette or through a fluid delivery system similar to the one described in FIG. 24. At least one of the wheel assembly 3001 or the multicavity container 3010 is rotated by the corresponding rotation devices 2201, 2306, thereby contacting the second immobilized chemical species with the mobile chemical species 3020 stored in the cavities 3015. One skilled in the art would recognize that each cavity 3015 may be loaded with different chemical species and that each wheel 2000 may be disposed with fibers immobilized with different chemical species. Because the processing time for multiple samples is not much greater than that for processing a single sample, the multi-wheel-multi-chamber system of FIGS. 30 and 31 offers a benefit of reducing labor cost per sample. It is appreciated that other features and advantages of the fiber wheel mixing system 2000 described in FIGS. 20 through 27 equally apply to the multi-wheel-multi-chamber system 3000 of FIGS. 30 and 31. For example, the wheel assembly 3001 and the multi-cavity container 3010 can be counter-rotated at a speed enough to generate a turbulent mixing zone at the mix points.

In a further embodiment of the invention, instead of fibers, an array of spots or dots of a chemical species may be incorporated into the wheel mixing system. These spots preferably form a cylindrical micro-array on an outer surface of a wheel. The spots may be immobilized onto a distinct substrate which is capable of transmitting light, or directly onto the outer perimeter of the wheel itself, where the wheel is made of a light transmitting material. The chemical species immobilized onto the substrate may either be directly applied onto the wheel, onto the substrate positioned around the circumference of the wheel or onto a flat substrate which is later conformed to the shape of the wheel. Light entering the light transmitting material from a laser, forms an evanescent wave close to the perimeter surface of the wheel which using the reader described above, is used to detect binding of the chemical species. The light transmitting material is preferably a glass material.

The fiber wheel mixing apparatus provides a high-quality apparatus for contacting different chemical species. Because the fibers can be easily tested to determine the quality of immobilization of the chemical species on the fiber, high quality fibers can be preferentially selected for use on the wheel.

In addition, the fibers of the present invention are completely dried after being immobilized with a chemical species and before being disposed on the wheel. Accordingly, contamination between mix points may be prevented, since there is little possibility of splattering one chemical species onto another, as can be the case with robot spotting.

The fiber wheel mixing apparatus is also relatively easy to use. The sample containing a mobile chemical species is simply loaded into the container with a syringe or pipette or by an appropriate fluid delivery apparatus. The wheel is placed into the container and a rotation device is activated. In case post-mixing washing should be necessary, the wheel can be removed from the container and dipped into a washing solution. Signals generated as a result of mixing can be detected and evaluated in a number of ways. The container can be discarded after use, thus eliminating the need for washing containers and reducing the potential for contamination.

Furthermore, by rotating both the wheel and the container in opposite directions, the fiber wheel mixing apparatus creates a turbulent mixing zone around the mix points. The turbulent mixing dramatically increases the contact efficiency. Due to such a highly efficient mixing mechanism, only a minimum amount of the second immobilized chemical species is required for mixing and analysis, which is far less than that of more conventional approaches.

The fiber wheel mixing apparatus also significantly improves the signal-to-noise ratio of the signals. For example, the light detecting device can analyze the light signals directly emanating from the mix points. With little stray to cause undesirable reflections, the noise collected by the light detecting device should be very low. In a desirable contrast, the amount of photons collected into the light detecting device is high because the wheel geometry, lenses, mirrors, and reflectors focus very high percentages of the light signal into the light detecting device. The high signal-to-noise ratio also provides significant improvement in the dynamic range and sensitivity of the fiber wheel mixing apparatus by two orders of magnitude over typical conventional spotting techniques.

Those of skill in the art will recognize that the fiber arrays of the invention can be used in virtually any assay where detecting interactions between to chemical species is desired. For example, the fiber arrays can be conveniently used to screen for and identify compounds which bind a receptor of interest, such as peptides which bind an antibody, organic compounds which bind an enzyme or receptor or complementary polynucleotides which bind (hybridize to) one another. However, the arrays of the invention are not limited to applications in which one chemical species binds another. The arrays of the invention can also be used to screen for and identify compounds which catalyze chemical reactions, such as antibodies capable of catalyzing certain reactions, and to screen for and identify compounds which give rise to detectable biological signals, such as compounds which agonize a receptor of interest. The only requirement is that the interaction between the two chemical species give rise to a detectable signal. Thus, the fiber arrays of the invention are useful in any applications that take advantage of arrays or libraries of immobilized compounds, such as the myriad solid-phase combinatorial library assay methodologies described in the art. For a brief review of the various assays for which the fiber arrays of the invention can be readily adapted, see Gallop et al., 1994, J. Med. Chem. 37:1233–1251; Gordon et al., 1994, J. Med. Chem. 37:1385–1401; Jung, 1992, Agnew Chem. Pat. Ed. 31:367–386; Thompson & Ellman, 1996, Chem Rev. 96: 555–600, and the references cited in all of the above.

The fiber arrays of the invention are particularly useful for applications involving hybridization of nucleic acids, especially those applications involving high density arrays of immobilized polynucleotides, including, for example, de novo sequencing by hybridization (SBH) and detection of polymorphisms. In these applications, conventional immobilized polynucleotide arrays typically used in the art can be conveniently and advantageously replaced with the fiber arrays of the invention. For a review of the various array-based hybridization assays in which the fiber arrays of the invention find use, see U.S. Pat. Nos. 5,202,231; 5,525,464; WO 98/31836, and the references cited in all of the above.

Based on the above, those of skill in the art will recognize that the chemical species immobilized on the fiber can be virtually any types of compounds, ranging from organic compounds such as potential drug candidates, polymers and small molecule inhibitors, agonists and/or antagonists, to biological compounds such as polypeptides, polynucleotides, polycarbohydrates, lectins, proteins, enzymes, antibodies, receptors, nucleic acids, etc. The only requirement is that the chemical species be capable of being immobilized on the fiber.

In a preferred embodiment, the chemical species immobilized on the fiber is a polynucleotide. Typically, the polynucleotide will be of a strandedness and length suitable for format II and format III SBH and related applications. Thus, the polynucleotide will generally be single-stranded and be composed of between about 4 to 30, typically about 4 to 20, and usually about 5, 6, 7, 8, 9, 10, 11, 12, 13, 14, or 20 nucleotides. However, it will be recognized that the fiber arrays of the invention are equally well suited for use with format I SBH, and related applications, where an immobilized target nucleic acid is interrogated with solution-phase oligonucleotide probes. Thus, the polynucleotide can be any number of nucleotides in length and be either single- or double-stranded, depending on the particular application.

The polynucleotide may be composed entirely of deoxyribonucleotides, entirely of ribonucleotides, or may be composed of mixtures of deoxy- and ribonucleotides. However, due to their stability to RNases and high temperatures, as well as their ease of synthesis, polynucleotides composed entirely of deoxyribonucleotides are preferred.

The polynucleotide may be composed of all natural or all synthetic nucleotide bases, or a combination of both. While in most instances the polynucleotide will be composed entirely of the natural bases (A, C, G, T or U), in certain circumstances the use of synthetic bases may be preferred. Common synthetic bases of which the polynucleotide may be composed include 3-methlyuracil, 5,6-dihydrouracil, 4-thiouracil, 5-bromouracil, 5-thorouracil, 5-iodouracil, 6-dimethyl amino purine, 6-methyl amino purine, 2-amino purine, 2,6-diamino purine, 6-amino-8-bromo purine, inosine, 5-methyl cytosine, and 7-deaza quanosine. Additional non-limiting examples of synthetic bases of which the polynucleotide can be composed can be found in Fasman, CRC Practical Handbook of Biochemistry and Molecular Biology, 1985, pp. 385–392.

Moreover, while the backbone of the polynucleotide will typically be composed entirely of "native" phosphodiester linkages, it may contain one or more modified linkages, such as one or more phosphorothioate, phosphoramidite or other modified linkages. As a specific example, the polynucleotide may be a peptide nucleic acid (PNA), which contains amide interlinkages. Additional examples of modified bases and backbones that can be used in conjunction with the invention, as well as methods for their synthesis can be found, for example, in Uhlman & Peyman, 1990, Chemical Review 90(4):544–584; Goodchild, 1990, Bioconjugate Chem. 1(3):165–186; Egholm et al., 1992, J. Am. Chem. Soc. 114:1895–1897; Gryaznov et al., J. Am. Chem. Soc. 116:3143–3144, as well as the references cited in all of the above.

While the polynucleotide will often be a contiguous stretch of nucleotides, it need not be. Stretches of nucleotides can be interrupted by one or more linker molecules that do not participate in sequence-specific base pairing interactions with a target nucleic acid. The linker molecules may be flexible, semi-rigid or rigid, depending on the desired application. A variety of linker molecules useful for spacing one molecule from another or from a solid surface have been described in the art (and have been described more thoroughly supra); all of these linker molecules can be used to space regions of the polynucleotide from one another. In a preferred embodiment of this aspect of the invention, the linker moiety is from one to ten, preferably two to six, alkylene glycol moieties, preferably ethylene glycol moieties.

The polynucleotide can be isolated from biological samples, generated by PCR reactions or other template-specific reactions, or made synthetically. Methods for isolating polynucleotides from biological samples and/or PCR reactions are well-known in the art, as are methods for synthesizing and purifyng synthetic polynucleotides. Polynucleotides isolated from biological samples and/or PCR reactions may, depending on the desired mode of immobilization, require modification at the 3'- or 5'-terminus, or at one or more bases, as will be discussed more thoroughly below. Moreover, since the polynucleotide must typically be capable of hybridizing to another target nucleic acid, if not already single stranded, it should preferably be rendered single stranded, either before or after immobilization on the fiber.

Depending on the identity of the chemical species and the fiber material, the chemical species can be immobilized by virtually any means known to be effective for immobilizing the particular type of chemical species on the particular type of fiber material. For example, the chemical species can be immobilized via absorption, adsorption, ionic attraction or covalent attachment. The immobilization may also be mediated by way of pairs of specific binding molecules, such as biotin and avidin or streptavidin. Methods for immobilizing a variety of chemical species to a variety of materials are known in the art. Any of these art-known methods can be used in conjunction with the invention.

For adsorption or absorption, fiber 11 can be conveniently prepared by contacting the fiber with the chemical species to be immobilized for a time period sufficient for the chemical species to adsorb or absorb onto the fiber. Following optional wash steps, the fiber is then dried. When the chemical species is a polynucleotide, the various methods described in the dot-blot or other nucleic acid blotting arts for immobilizing nucleic acids onto nitrocellulose or nylon filters can be conveniently adapted for use in the present invention.

For immobilization by ionic attraction, if not inherently charged, the fiber is first activated or derivatized with charged groups prior to contacting it with the chemical species to be immobilized, which is either inherently oppositely charged or has been modified to be oppositely charged.

For immobilization mediated by way of specific binding pairs, the fiber is first derivatized and/or coated with one member of the specific binding pair, such as avidin or streptavidin, and the derivatized fiber is then contacted with a chemical species which is linked to the other member of the specific binding pair, such as biotin. Methods for derivatizing or coating a variety of materials with binding molecules such as avidin or streptavidin, as well as methods for linking myriad types of chemical species to binding molecules such as biotin are well known in the art. For polynucleotide chemical species, biotin can be conveniently incorporated into the polynucleotide at either a terminal and/or internal base, or at one or both of its 5'- and 3'- termini using commercially available chemical synthesis or biological synthesis reagents.

In a preferred embodiment of the invention, the chemical species is covalently attached to the fiber, optionally be way of one or more linking moieties. Unless the fiber inherently contains reactive functional groups capable of forming a covalent linkage with the chemical species, it must first be activated or derivatized with such reactive groups. Typical reactive groups useful for effecting covalent attachment of chemical species to the fiber include hydroxyl, sulfonyl, amino, cyanate, isocyanate, thiocyanate, isothiocyanate, epoxy and carboxyl groups, although other reactive groups as will be apparent to those of skill in the art may also be used.

A variety of techniques for activating myriad types of fiber materials with reactive groups suitable for covalently attaching chemical species thereto, particularly biological molecules such as polypeptides, proteins, polynucleotides and nucleic acids, are known in the art and include, for example, chemical activation, corona discharge activation; flame treatment activation; gas plasma activation and plasma enhanced chemical vapor deposition. Any of these techniques can be used to activate the fiber with reactive groups. For a review of the many techniques that can be used to activate or derivatize the fiber, see Wiley Encyclopedia of Packaging Technology, 2d Ed., Brody & Marsh, Ed., "Surface Treatment," pp. 867–874, John Wiley & Sons, 1997, and the references cited therein. Chemical methods suitable for generating amino groups on preferred glass optical fibers are described in Atkinson & Smith, "Solid Phase Synthesis of Oligodeoxyribonucleotides by the Phosphite Triester Method," In: Oligonucleotide Synthesis: A Practical Approach, M J Gait, Ed., 1985, IRL Press, Oxford, particularly at pp. 45–49 (and the references cited therein); chemical methods suitable for generating hydroxyl groups on preferred optical glass fibers are described in Pease et al., 1994, Proc. Natl. Acad. Sci. USA 91:5022–5026 (and the references cited therein); chemical methods suitable for generating functional groups on fiber materials such as polystyrene, polyamides and grafted polystyrenes are described in Lloyd-Williams et al., 1997, Chemical Approaches to the Synthesis of Peptides and Proteins, Chapter 2, CRC Press, Boca Raton, Fla. (and the references cited therein). Additional methods are well-known, and will be apparent to those of skill in the art.

For fibers coated with a conductor, such as gold, the chemical species can be attached to the conductor using known chemistries. For example, a polynucleotide can be covalently attached to a gold-coated fiber using the methods described in Herne & Taylor, 1997, J. Am. Chem. Soc. 119:8916–8920. This chemistry can be readily adapted for covalently immobilizing other types of chemical species onto a gold-coated fiber.

Depending on the nature of the chemical species, it can be covalently immobilized on the activated fiber following synthesis and/or isolation, or, where suitable chemistries are known, it may be synthesized in situ directly on the activated fiber. For example, a purified polypeptide may be covalently immobilized on an amino-activated fiber, conveniently by way of its carboxy terminus or a carboxyl-containing side chain residue. Alternatively, the polypeptide can be synthesized in situ directly on an amino-activated fiber using conventional solid-phase peptide chemistries and reagents (see Chemical Approaches to the Synthesis of Peptides and Proteins, Lloyd-Williams et al., Eds., CRC Press, Boca Raton, Fla., 1997 and the references cited therein). Similarly, a purified polynucleotide bearing an appropriate reactive group at one or more of its bases or termini can be covalently immobilized on an isothiocyanate- or carboxy-activated fiber, or alternatively, the polynucleotide can be synthesized in situ directly on a hydroxyl-activated fiber using conventional oligonucleotide synthesis chemistries and reagents (see Oligonucleotide Synthesis: A Practical Approach, 1985, supra, and the references cited therein). Other types of compounds which can be conveniently synthesized by solid phase methods can also be synthesized in situ directly on a fiber. Non-limiting examples of compounds which can be synthesized in situ include Bassenisi and Ugi condensation products (WO 95/02566), peptoids (Simon et al., 1992, Proc. Natl. Acad. Sci. USA 89:9367–9371), non-peptide non-oligomeric compounds (Dewitt et al., 1993, Proc. Natl. Acad. Sci. USA 90:6909–6913) and 1,4 benzodiazepines and derivatives (Bunin et al., 1994, Proc. Natl. Acad. Sci. USA 91:4708–4712); Bunin & Ellman, 1992, J. Am. Chem. Soc. 114:10997–10998).

Those of skill in the art will recognize that when using in situ chemical synthesis, the covalent bond formed between the immobilized chemical species and the fiber must be substantially stable to the synthesis and deprotection conditions so as to avoid loss of the chemical species during synthesis and/or deprotection. For polynucleotides, one such stable bond is the phosphodiester bond, which connects the various nucleotides in a polynucleotide, and which can be conveniently formed using well-known chemistries (see, e.g., Oligonucleotide Synthesis: A Practical Approach, 1985, supra). Other stable bonds suitable for use with hydroxyl-activated fibers include phosphorothiate, phosphoramidite, or other modified nucleic acid interlinkages. For fibers activated with amino groups, the bond could be a phosphoramidate, amide or peptide bond. For fibers activated with epoxy functional groups, a stable C-N bond could be formed. Suitable reagents and conditions for forming such stable bonds are well known in the art.

In one particularly convenient embodiment, a polynucleotide is immobilized on a fiber by in situ synthesis on a hydroxyl-activated fiber using commercially available phosphoramidite synthesis reagents and standard oligonucleotide synthesis chemistries. In this mode, the polynucleotide is covalently attached to the activated fiber by way of a phosphodiester linkage. The density of polynucleotide covalently immobilized on the filter can be conveniently controlled by adding an amount of the first synthon (e.g., N-protected 5'-O-dimethoxytrityl-2'-deoxyribonucleotide-3'-O-phosphoramidite) sufficient to provide the desired number of synthesis groups on the fiber, and capping any unreacted hydroxyl groups on the fiber with a capping reagent (e.g., 1,4-diaminopyridine; DMAP). After the excess hydroxyls have been capped, the trityl group protecting the 5'-hydroxyl can be removed and synthesis of the polynucleotide carried out using standard techniques. Following synthesis, the polynucleotide is deprotected using conventional methods.

In an alternative embodiment, a polynucleotide is covalently attached to the activated fiber through a post-synthesis or post-isolation conjugation reaction. In this embodiment, a pre-synthesized or isolated polynucleotide which is modified at its 3'-terminus, 5-terminus and/or at one of its bases with a reactive functional group (e.g. epoxy, sulfonyl, amino or carboxyl) is conjugated to an activated fiber via a condensation reaction, thereby forming a covalent linkage. Again, substantially stabile (i.e., non-labile) covalent linkages such as amide, phosphodiester and phosphoramidate linkages are preferred. Synthesis supports and synthesis reagents useful for modifying the 3'- and/or 5'-terminus of synthetic polynucleotides, or for incorporating a base modified with a reactive group into a synthetic polynucleotide, are well-known in the art and are even commercially available.

For example, methods for synthesizing 5'-modified oligonucleotides are described in Agarwal et al., 1986, Nucl. Acids Res. 14:6227–6245 and Connelly, 1987, Nucl. Acids Res. 15:3131–3139. Commercially available products for synthesizing 5'-amino modified oligonucleotides include the N-TFA-C6-AminoModifer™, N-MMT-C6-AminoModifer™ and N-MMT-C12-AminoModifier™ reagents available from Clontech Laboratories, Inc., Palo Alto, Calif.

Methods for synthesizing 3'-modified oligonucleotides are described in Nelson et al., 1989, Nucl. Acids Res. 17:7179–7186 and Nelson et al., 1989, .Nucl. Acids Res. 17:7187–7194. Commercial products for synthesizing 3'-modified oligonucleotides include the 3'-Amino-ONm controlled pore glass and Amino Modifier II™ reagents available from Clontech Laboratories, Inc., Palo Alto, Calif.

Other methods for modifying the 3' and/or 5' termini of oligonucleotides, as well as for synthesizing oligonucleotides containing appropriately modified bases are provided in Goodchild, 1990, Bioconjugate Chem. 1:165–186, and the references cited therein. Chemistries for attaching such modified oligonucleotides to materials activated with appropriate reactive groups are well-known in the art (see, e.g., Ghosh & Musso, 1987, Nucl. Acids Res. 15:5353–5372; Lund et al., 1988, Nucl. Acids Res. 16:10861–10880; Rasmussen et al., 1991, Anal. Chem. 198:138–142; Kato & Ikada, 1996, Biotechnology and Bioengineering 51:581–590; Timofeev et al., 1996, Nucl. Acids Res. 24:3142–3148; O'Donnell et al., 1997, Anal. Chem. 69:2438–2443).

Methods and reagents for modifying the ends of polynucleotides isolated from biological samples and/or for incorporating bases modified with reactive groups into nascent polynucleotides are also well-known and commercially available. For example, an isolated polynucleotide can be phosphorylated at its 5'-terminus with phosphorokinase and this phosphorylated polynucleotide covalently attached onto an amino-activated fiber through a phosphoramidate or phosphodiester linkage. Other methods will be apparent to those of skill in the art.

In one convenient embodiment of the invention, a polynucleotide modified at its 3'- or 5'-terminus with a primary amino group is conjugated to a carboxy-activated fiber. Chemistries suitable for forming carboxamide linkages between carboxyl and amino functional groups are well-known in the art of peptide chemistry (see, e.g., Atherton & Sheppard, Solid Phase Peptide Synthesis, 1989, IRL Press, Oxford, England and Lloyd-Williams et al., Chemical Approaches to the Synthesis of Peptides and Proteins, 1997, CRC Press, Boca Raton, Fla. and the references cited therein). Any of these methods can be used to conjugate an amino-modified polynucleotide to a carboxy-activated fiber.

In one embodiment, the carboxamide linkage is generated using N,N,N',N'-tetramethyl (succinimido) uronium tetrafluoroborate ("TSTU") as a coupling reagent. Reaction conditions for the formation of carboxyamides with TSTU that can be used in conjunction with nucleic acids are described in Knorr et al., 1989, Tet. Lett. 30(15):1927–1930; Bannworth & Knorr, 1991, Tet. Lett. 32(9):1157–1160; and Wilchek et al., 1994, Bioconjugate Chem. 5(5):491–492.

Whether synthesized directly on the activated fiber or immobilized on the activated fiber post-synthesis or post-isolation, the chemical species can optionally be spaced away from the porous substrate by way of one or more linkers. As will be appreciated by those having skill in the art, such linkers will be at least bifunctional, i.e., they will have one functional group or moiety capable of forming a linkage with the activated fiber and another functional group or moiety capable of forming a linkage with another linker molecule or the chemical species. The linkers may be long or short, flexible or rigid, charged or uncharged, hydrophobic or hydrophilic, depending on the particular application.

In certain circumstances, such linkers can be used to "convert" one functional group into another. For example, an amino-activated fiber can be converted into a hydroxyl-activated fiber by reaction with, for example, 3-hydroxy-propionic acid. In this way, fiber materials which cannot be readily activated with a specified reactive functional group can be conveniently converted into a an appropriately activated fiber. Chemistries and reagents suitable for "converting" such reactive groups are well-known, and will be apparent to those having skill in the art.

Linkers can also be used, where necessary, to increase or "amplify" the number of reactive groups on the activated fiber. For this embodiment, the linker will have three or more functional groups. Following attachment to the activated fiber by way of one of the functional groups, the remaining two or more groups are available for attachment of the chemical species. Amplifying the number of functional groups on the activated fiber in this manner is particularly convenient when the activated fiber contains relatively few reactive groups.

Reagents for amplifying the number of reactive groups are well-known and will be apparent to those of skill in the art. A particularly convenient class of amplifying reagents are the multifunctional epoxides sold under the trade name DENACOL™ (Nagassi Kasei Kogyo K.K.). These epoxides contain as many as four, five, or even more epoxy groups, and can be used to amplify fibers activated with reactive groups that react with epoxides, including, for example, hydroxyl, amino and sulfonyl activated fibers. The resulting epoxy-activated fibers can be conveniently converted to a hydroxyl-activated fiber, a carboxy-activated fiber, or other activated fiber by well-known methods.

Linkers suitable for spacing biological or other molecules, including polypeptides and polynucleotides, from solid surfaces are well-known in the art, and include, by way of example and not limitation, polypeptides such as polyproline or polyalanine, saturated or unsaturated bifunctional hydrocarbons such as 1-amino-hexanoic acid and polymers such as polyethylene glycol, etc. For polynucleotide chemical species, a particularly preferred linker is polyethylene glycol (MW 100 to 1000). 1,4-Dimethoxytrityl-polyethylene glycol phosphoramidites useful for forming phosphodiester linkages with hydroxyl groups of hydroxyl-activated fibers, as well as methods for their use in nucleic acid synthesis on solid substrates, are described, for example in Zhang et al., 1991, Nucl. Acids Res. 19:3929–3933 and Durand et al., 1990, Nucl. Acids Res. 18:6353–6359. Other methods of attaching polyethylene glycol linkers to activated fibers will be apparent to those of skill in the art.

Regardless of the mode of immobilization, fibers 11 can be prepared in a batch-wise fashion where lengths of fiber are immersed in the solutions necessary to effect immobilization of the chemical species. Alternatively, fibers 11 can be prepared in a flow-through method in which the fiber is continuously flowed through reservoirs containing the solutions necessary to effect immobilization.

Figure 32:
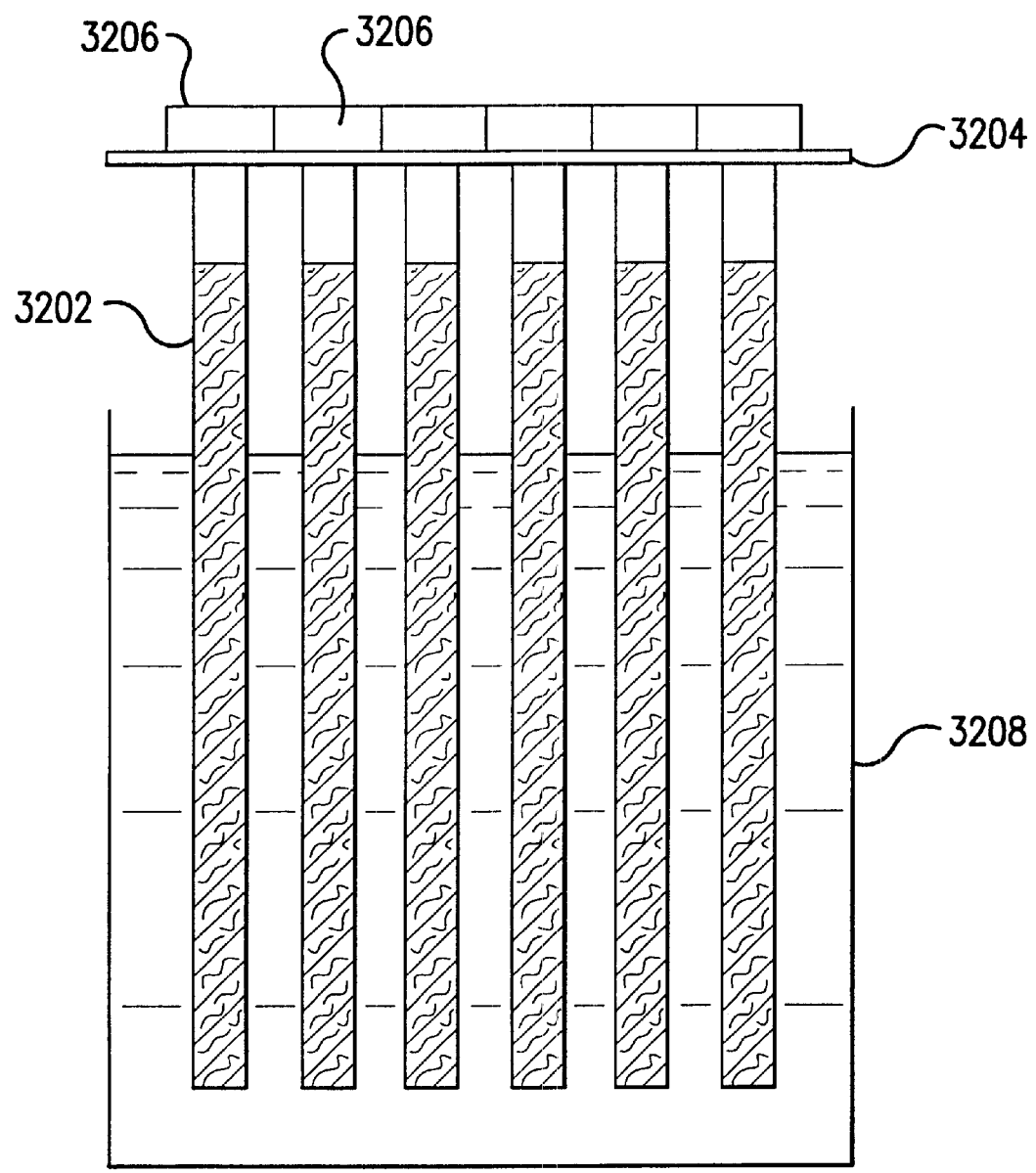
FIG. 32 shows one embodiment for preparing a fiber for use in a fiber array according to the present invention.

FIG. 32 is one embodiment for preparation of the fiber for use in the fiber array according to the present invention in a batch-wise fashion. The fibers 3202 are attached to a fiber holder 3204 comprising fiber grippers 3206 which hold the fiber 3202. The fiber holder 3204 permits the fiber to be easily supported and transported and can be attached to any mechanical device (not shown) to automatically transport the fibers 3202. A dipping vessel 3208 is a vessel that can contains a fluid to be contacted with the fibers 3202. In operation, the fibers 3202 are attached to the fiber grippers 3206, and the fiber holder 3204 lowers the fibers 3202 into a solution contained in the dipping vessel 3208. The fiber holder [1304] 3204 then removes the fibers [1302] 3202 from the dipping vessel [1308] 3208. It should be appreciated that the fibers may be sequentially placed into different dipping vessels each containing different solutions depending upon the chemical species to be immobilized on the fibers and the method used for immobilization. After the chemical species has been immobilized on the fibers, the fibers may be loaded onto a support plate or stored for future use. If the fibers are stored, refrigeration may be necessary depending upon the chemical species on the fibers.

It is projected that with the present invention, once the fibers have been prepared as described, 100 fibers, each 10 cm in length, could be laid per second on a 10 cm support plate thereby producing 1,000,000 contact points. It should be appreciated that laying the fibers on the support plate only requires accurate placement in a direction parallel to the channels to insure the fiber rests in the grooves on the channel walls. Since the fiber can be placed anywhere in the direction parallel to the fiber, placing the fiber on the support plate is relatively simple.

Figure 33:
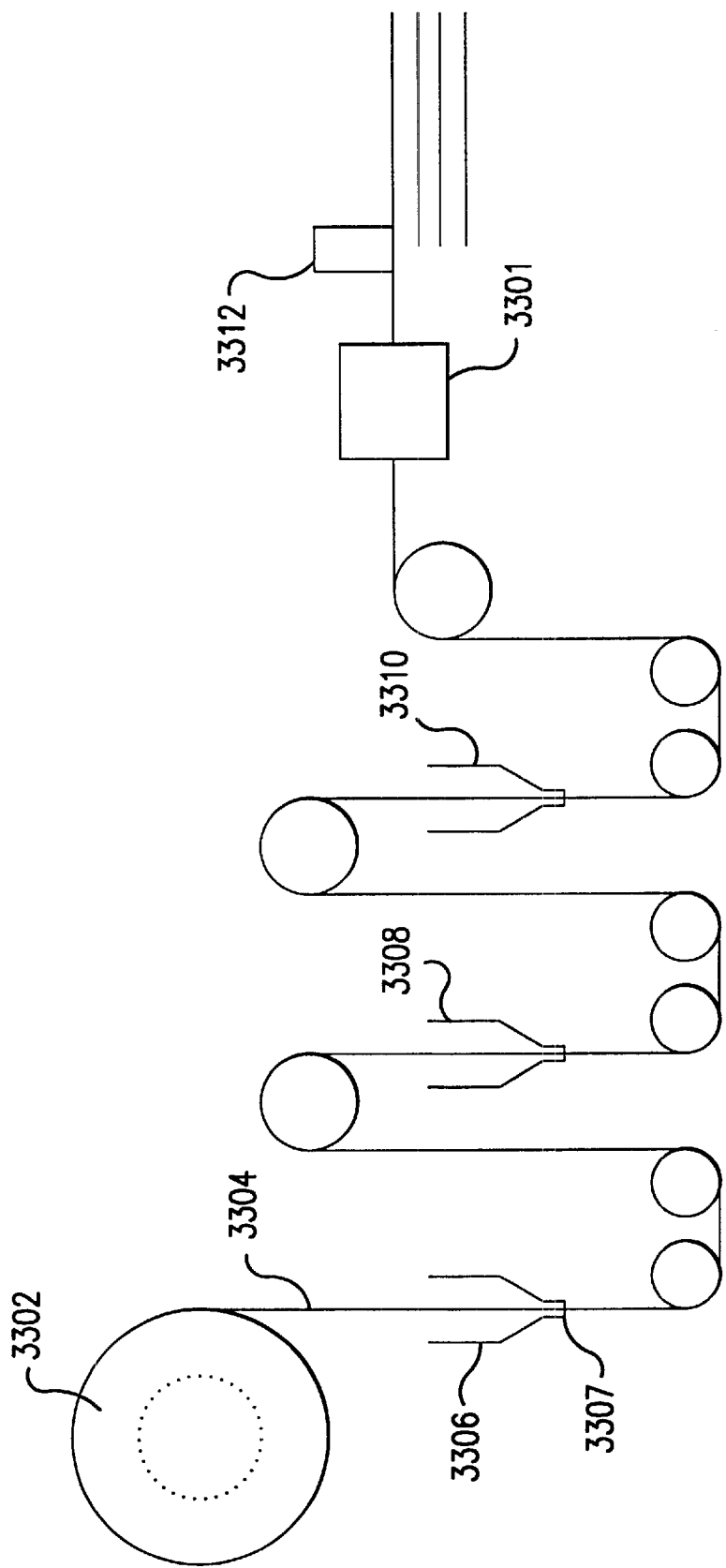
FIG. 33 shows another embodiment for preparing a fiber for use in the fiber array according to the present invention.

FIG. 33 is a process flow diagram of another embodiment for preparation of the fiber in a flow-through method for use in the fiber array according to the present invention. A motor 3301 is used to pull a fiber 3304 from a fiber spool 3302 containing a length of material desired to be used for the fibers 3304. If it is desired to coat the fiber 3304 with a conductive coating, the fiber 3304 is first pulled through a conductive coating vat 3306 which contains a pool of conductive material to be coated on the fiber 3304. More specifically, the conductive coating vat 3306 utilizes meniscus coating to apply the conductive coating to the fiber 3304, wherein the fiber 3304 is pulled through a narrow opening 3307 which only permits a thin layer of metal coating to be applied to the fiber 3304. It should be appreciated that a conductive coating is not required for use of the fiber array of the present invention. However, to utilize electro-osmosis, a metal or electrically conductive oxide coating is preferred.

The fiber 3304 is then passed through a series of coating vats 3308, 3310 depending upon the chemical species to be immobilized on the fibers and the method used for immobilization. Each coating vat may contain a different solution required to prepare the fiber and immobilize a given chemical species on the fiber.

Lastly, the fiber 3304 is fed past the motor 3301 and is cut into desired lengths by cutting apparatus 3312. It should be appreciated that any length of fiber may be generated depending upon the size of the fiber array matrix. The cutting apparatus 3312 may be a laser or other means known in the art for cutting fibers or optical fibers. It should be appreciated that it is important to obtain a very clean and straight cut if the fiber 3304 is an optical fiber so that in use the beam of light directed at the end of the fiber is able to enter the fiber at the correct angle. Once cut, the fibers 1404 may be loaded onto a support plate or stored for later use. If the fibers are stored, refrigeration may be necessary depending upon the materials deposited on the fibers.

Following preparation by either of the methods described above, a length of fiber can be conveniently analyzed to verify the quality of the immobilization process. For example, the chemical species immobilized on a portion of the fiber can be removed using conventional means and analyzed using any of a variety of analytical techniques, including, for example, gel electrophoresis (for polypeptides and polynucleotides), nuclear magnetic resonance, column chromatography, mass spectroscopy, gas chromatography, etc. Of course, the actual analytical means used to analyze the fiber will depend on the nature of the chemical species attached thereto, and will be apparent to those of skill in the art.

While not preferred, fibers 110 may also be prepared, i.e., the chemical species may be immobilized to the fibers, while the fibers are disposed within the fiber array. In this embodiment, once the fibers are disposed in the support plate, the various fluids necessary to activate and/or immobilize the chemical species to the fiber are flowed into channels 108 to contact the fiber. This method is particularly convenient when it is desirable to immobilize different chemical species at different spatial addresses along the length of the fiber.

The present invention is further directed to an apparatus and method for synthesizing a chemical compound on a fiber. The synthesized fibers are then used to fabricate fiber arrays discussed supra. This apparatus is a fiber array multiplicative synthesizer that implements a direct process of moving a fiber through a plurality of coating modules that synthesize one base onto the fiber. The coating modules can be stacked into columns with a fiber passing out of one module into the next module. Each module sequentially adds one base to the oligo. In one configuration, many columns of coating modules can be grouped into hubs, and those hubs can be rotated relative to each other such that the number of different oligos generated is much greater than the number of coating modules deployed, thus the name multiplicative synthesis. The fibers extracted from the multiplicative synthesizer system are directly loaded into a fiber array. After sealing, the fiber array is immediately ready as an analysis tool. In a second configuration, the modules are programmable to provide complex oligo configurations on-demand.

Figure 34:
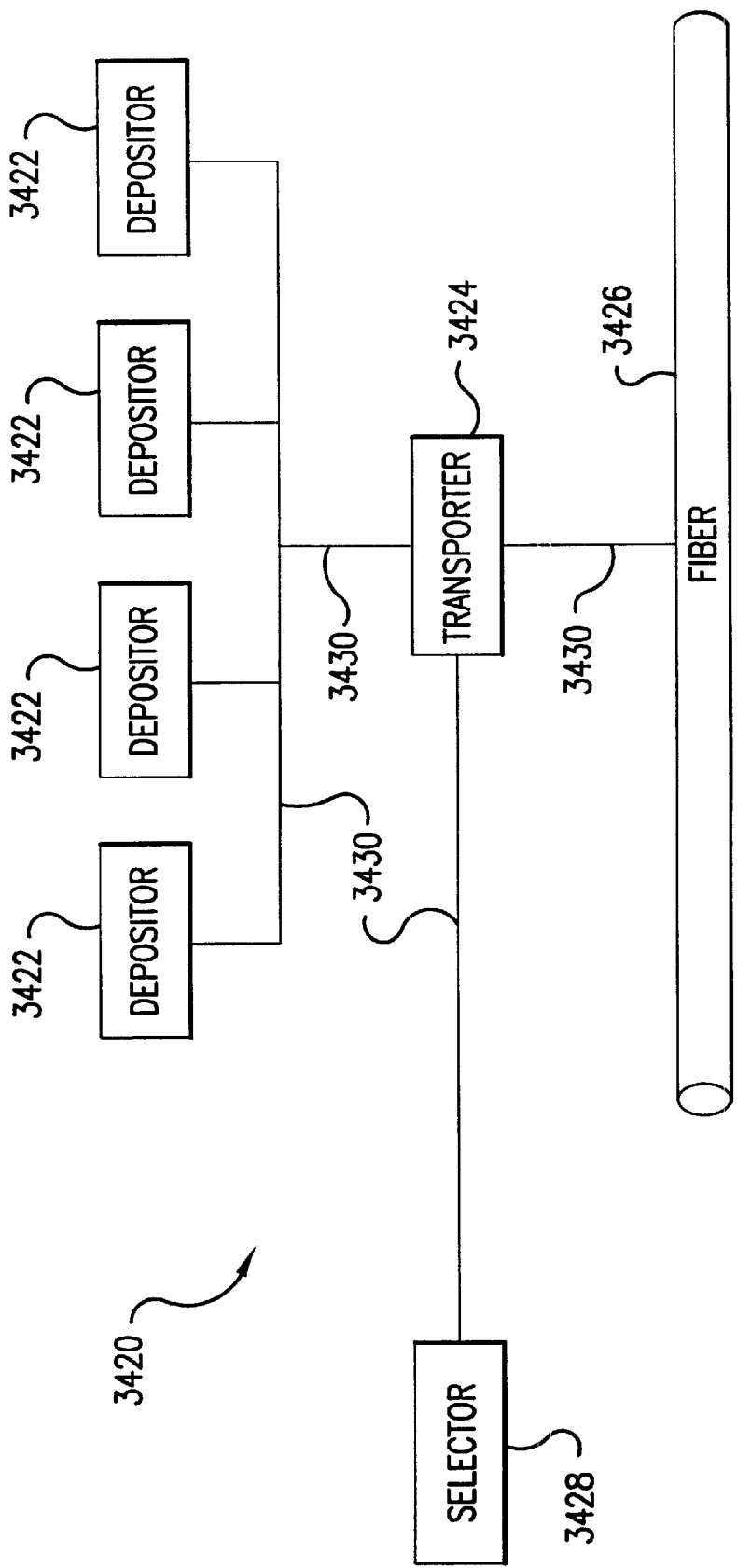
FIG. 34 is a diagrammatic view of the invention.

FIG. 34 is a diagrammatic drawing of a multiplicative fiber array synthesizer 3420 according to the present invention. The fiber array synthesizer 3420 comprises at least one, but preferably a plurality of, depositors 3422 where each of the depositors 3422 is capable of depositing a chemical species on a fiber 3426. The depositors 3422, as explained in further detail below, may comprise a plurality of baths, spray chambers, wicking mechanisms, or the like. The multiplicative fiber array synthesizer 3420 further comprises a transporter 3424. The transporter 3424 may bring the fiber 3426 and the depositors 3422 into proximity with one another, as indicated by control lines 3430, in order to deposit at least one chemical species precursor on the fiber 3426 to form the chemical species. The transporter 3424 may move the depositors 3422 into proximity with the fiber 3426, the fiber 3426 into proximity with the depositors 3422, or both the depositors 3422 and the fiber 3426 relative to one another. Alternatively, the transporter may comprise a fluid delivery system for delivering the chemical species precursors to each of said depositors 3422 the control of which is again indicated by the control lines 3430. Specific examples of the transporter 3424 will be discussed in further detail below. A selector 3428 controls the order in which each of the at least one chemical species precursor is deposited on the fiber 3426 from each of the depositors 3422. This may be done by controlling the transporter 3424 to move the depositors 3422 into proximity with the fiber 3426 in a predetermined order or by controlling the transporter 3424 to move the fiber 3426 into proximity with the depositors 3422 in a predetermined order. The selector 3428 may also control the order in which each of the at least one chemical species precursor is supplied to each of the depositors 3422 by the fluid delivery system.

Figure 35A:
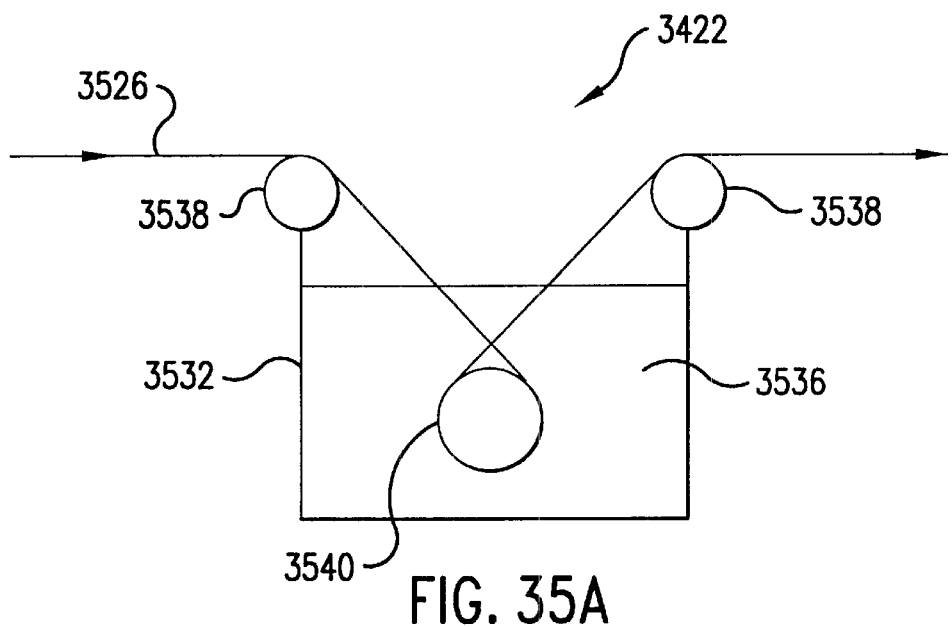
FIG. 35 is a side view of one embodiment of the invention.

FIG. 35A is a side view of one embodiment of depositors 3422 shown in FIG. 34. In this embodiment, each of the depositors 3422 comprise of at least one bath 3532 containing a chemical species precursor 3536. The chemical species precursor 3536 may for example comprise of a solution containing phosphoramodites or other solutions such as washing solvents. In a preferred embodiment, the transporter 3424 of FIG. 34 comprises a dipping mechanism for positioning the fiber 3526 in the bath 3532. The dipping mechanism may comprise a conveyor system such as a series of rollers 3538 and 340 which frictionally engage with the fiber 3526 to push the fiber 3526 through the bath 3532 and hence into contact with the chemical species 3536. The dipping mechanism may alternatively comprise a mechanism for dipping substantially straight lengths, or coils of the fiber 3526 directly into the bath 3532 and the chemical species 3536. The fiber 3526 may be wound multiple times around an immersed roller 3540 to vary the resonance time of the fiber 3526, as the fiber 3526 is moved through the bath 3532 at a constant speed. This means that the more times the fiber 3526 is wound around the roller 3540, the longer the fiber 3526 is exposed to the chemical species 3536. The roller 3540 may comprise of a cage like device which allows all points along the fiber 3526 at some time or another, to be exposed to the chemical species 3536.

Figure 35B:
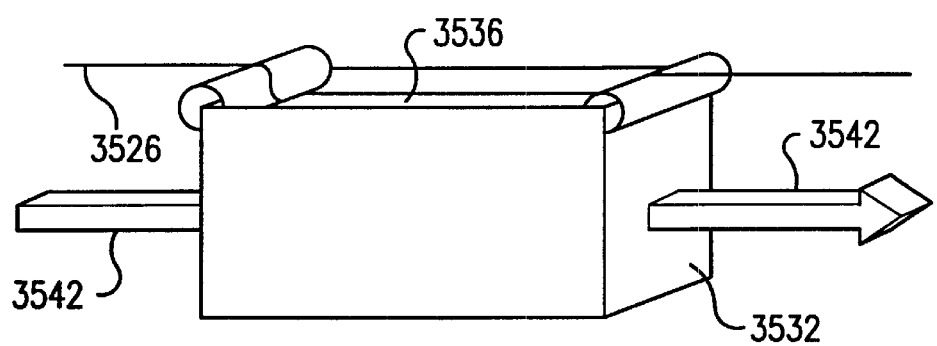

FIG. 35B is a perspective view of another embodiment of the invention. In this embodiment, the transporter 3424 of FIG. 34 comprises a bath transporter 3542 for moving the bath 3532, such that the chemical species precursor 3536 is brought into contact with the fiber 3526.

Figure 35C:
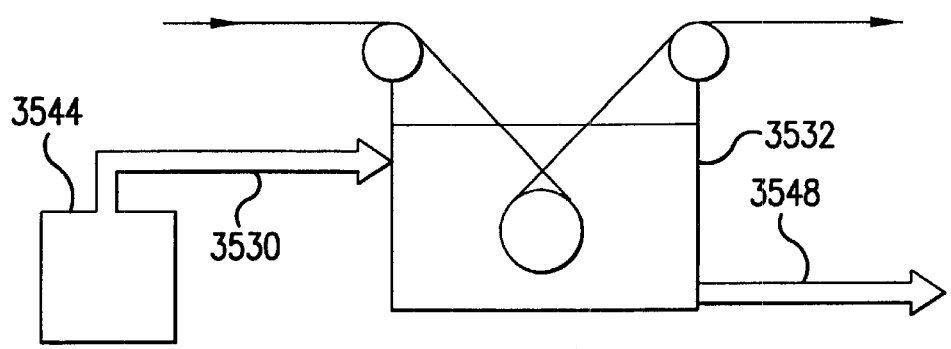

FIG. 35C is a side view of yet another embodiment of the invention. In this embodiment, the transporter 3424 of FIG. 34 comprises a fluid delivery system 3544 which delivers different chemical species precursors or solutions into 3530 and out of 3548 the bath 3532.

Figure 36A:
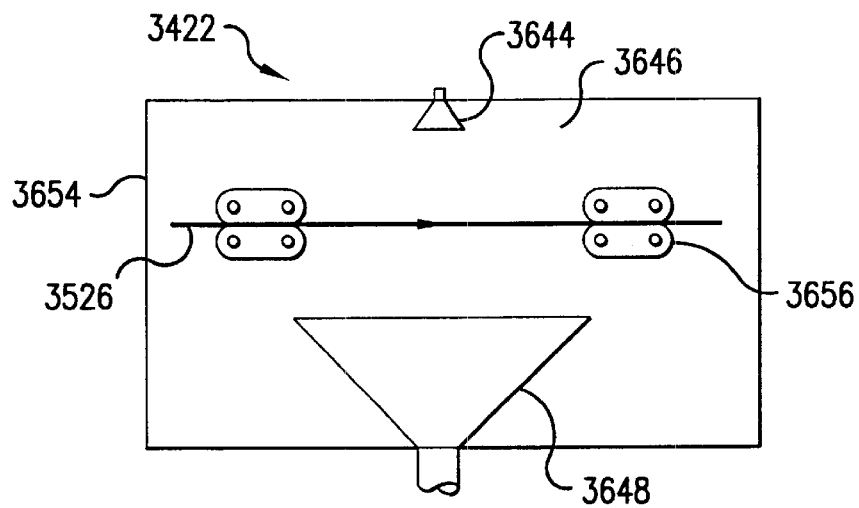
FIG. 36 is a side view of another embodiment of the invention.

FIG. 36A is a side view of an embodiment of depositors 3422 shown in FIG. 34. In this embodiment, each of the depositors 3422 comprise of at least one spray chamber 3654 and a spray mechanism 3644 for spraying the chemical species precursor 3646 onto the fiber 3526. Again the chemical species precursor 3646 may for example comprise of a solution containing phosphoramodites or other solutions such as washing solvents. In one embodiment, the transporter 3424 of FIG. 34 comprises a fiber transportation mechanism such as a conveyor system 3656 which frictionally engages with the fiber 3526 to push the fiber 3526 through the spray chamber 3654.

Figure 36B:
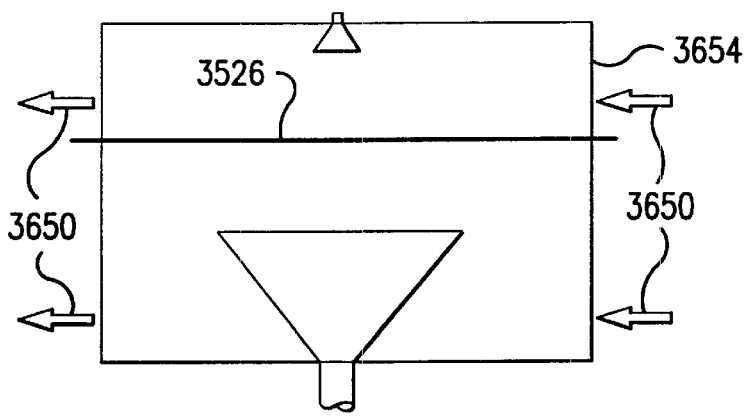

FIG. 36B is a side view of another embodiment of depositors 3422 shown in FIG. 34. The transporter 3424 of FIG. 34 may alternatively comprise of a spray chamber transporter 3650 for bringing the spray chamber 3654 into proximity with the fiber 3526.

Figure 36C:
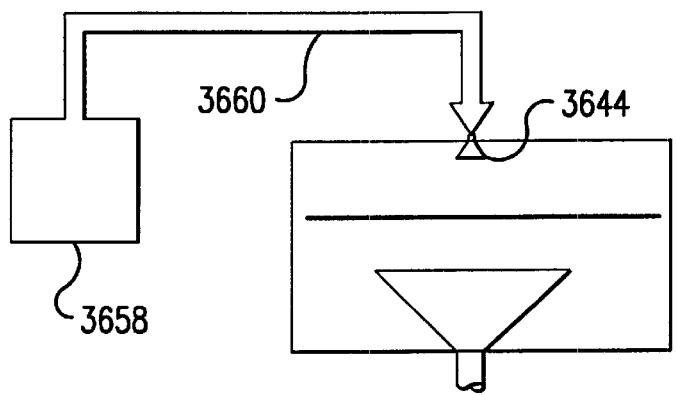

FIG. 36C is a side view of yet another embodiment of depositors 3422 shown in FIG. 34. In this embodiment, the transporter 3424 of FIG. 34 comprises a fluid delivery system 3658 which delivers 3660 different chemical species precursors or solutions to the spray mechanism 3644.

Figure 37A:
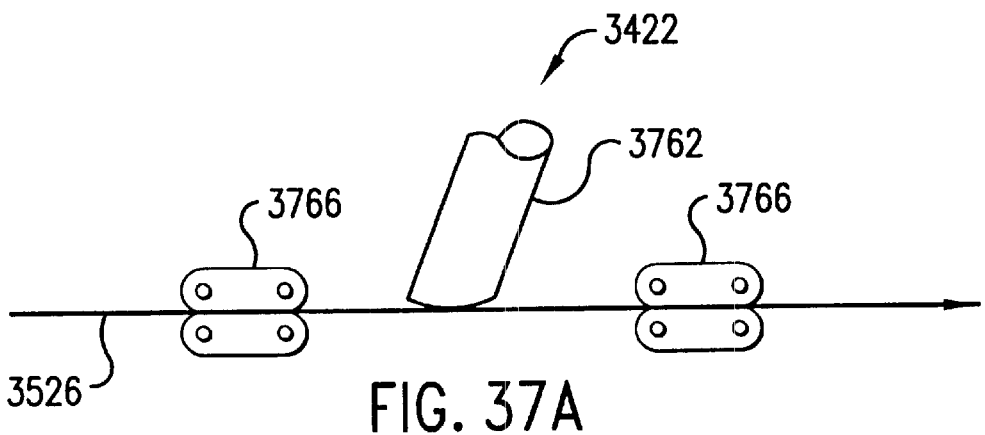
FIG. 37 is a side view of yet another embodiment of the invention.

FIG. 37A is a side view of an embodiment of depositors 3422 shown in FIG. 34. In this embodiment, each of the depositors 3422 comprise of at least one wicking mechanism 3762 for wicking a chemical species precursor 3764 onto the fiber 3526. Yet again the chemical species precursors may for example comprise of a solution containing phosphoramodites or other solutions such as washing solvents. The transporter 3424 of FIG. 34 comprises a fiber transportation mechanism such as a conveyor system 3766 which frictionally engages with the fiber 3526.

Figure 37B:
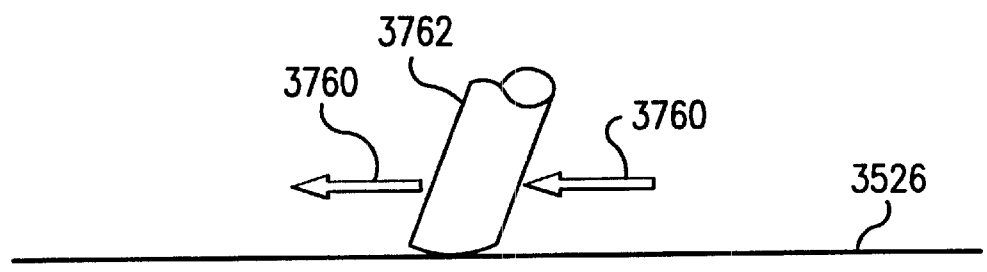

FIG. 37B is a side view of another embodiment of depositors 3422 shown in FIG. 34. The transporter 3424 of FIG. 34 comprises a wicking mechanism transporter 3760 for bringing the wicking mechanism 3762 into proximity with the fiber 3526.

Figure 37C:
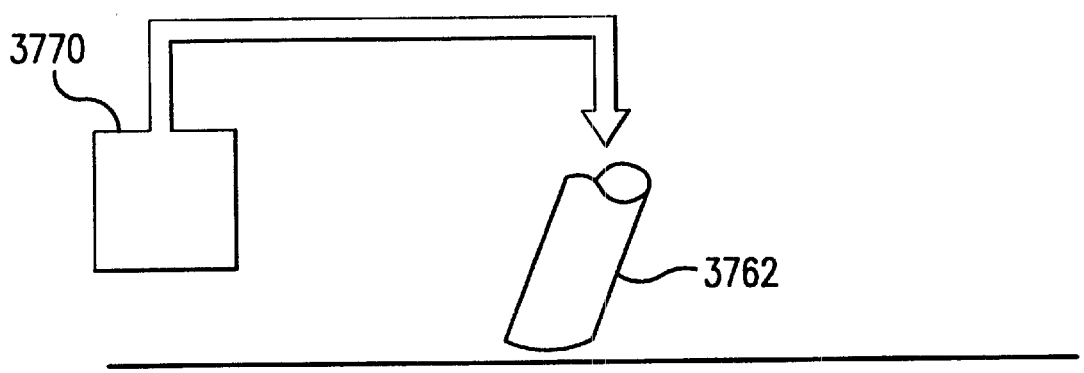

FIG. 37C is a side view of another embodiment of depositors 3422 shown in FIG. 34. The transporter 3524 of FIG. 34 comprises a fluid delivery system 3770 which delivers different chemical species or solutions to the wicking mechanism 3762.

In each of the above embodiments shown in FIGS. 35A to 37C, a mechanism to vary the resonance time of the fiber 3526 may be provided. The selector 3428 of FIG. 34 may controls the transporter, in all of it's alternative embodiments, to vary the order in which each of the plurality of chemical species precursors are deposited on the fiber 3526.

Figure 38:
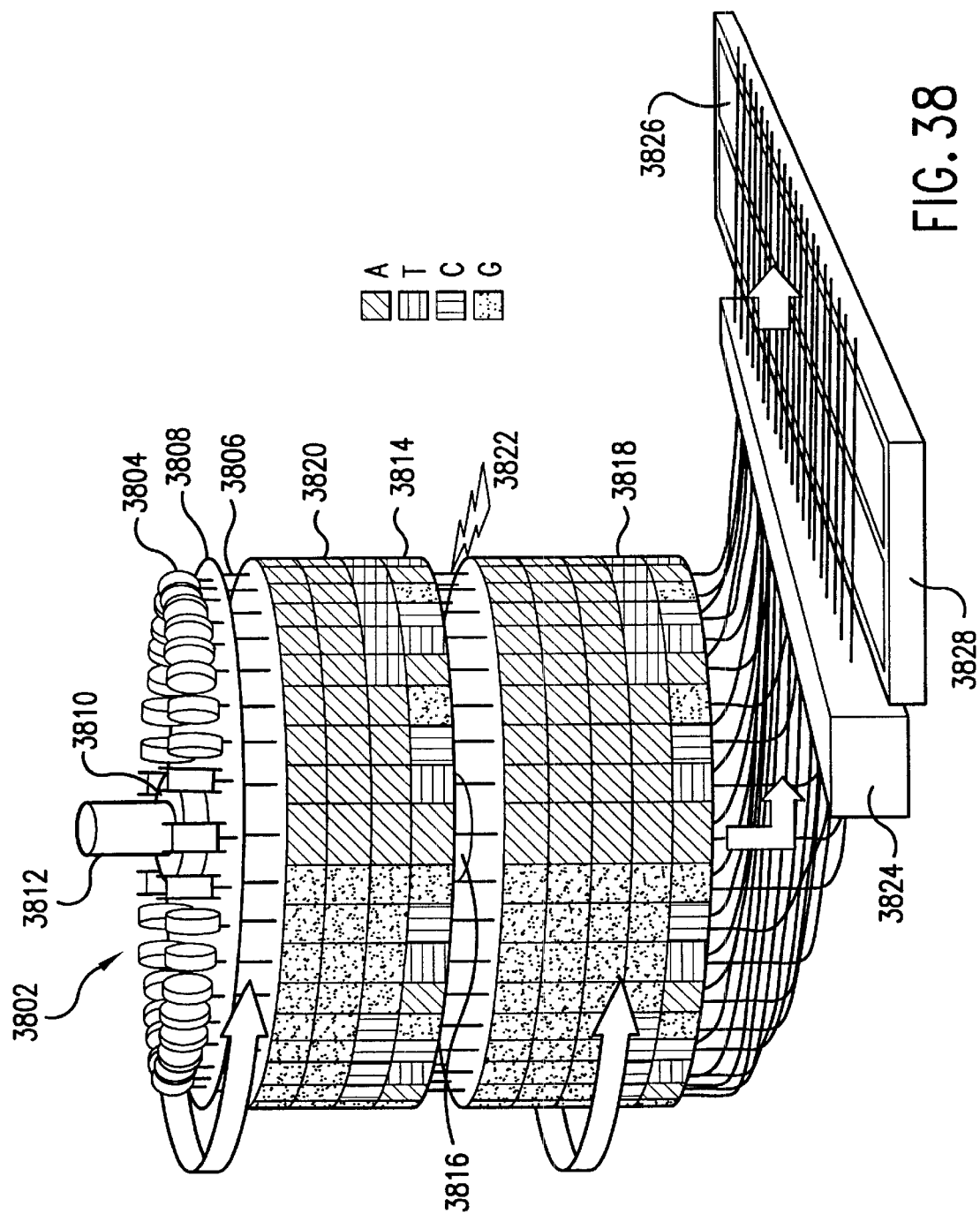
FIG. 38 is a perspective view of a preferred embodiment of the invention.

FIG. 38 is a perspective view of a preferred embodiment of the invention, namely a fiber array multiplicative synthesizer 3802. Multiple spools 3804 containing reeled-up fiber 3806 are mounted on a rotary platform 3808. The fibers 3806 typically comprise a flexible thread like material, such as for example plastic or glass, and are wrapped around spools 3804 such that many meters can be stored but readily retrieved. The spools 3804 are equally spaced in a circular pattern about the platform 3808 with the fibers 3806 passing through the platform 3808. The platform 3808 is fixed to motor 3810, and the motor 3810 is fixed to a support shaft 3812 that passes through the centers of the platform 3808 and both hubs 3814, 3818. Motor 3816 is also fixed to the support shaft 3812. The platform 3808 is rotatable about the support shaft 3812. The platform 3808 maybe rotated by a first rotation means 3810, such as a motor or the like. An upper hub 3814 is also rotatable about the support shaft 3812 and maybe rotated by a second rotation means 3816, such as a motor or the like. A lower hub 3818 is also rotatable about the support shaft 3812 and may be rotated by a third rotation means (not shown), such as a motor or the like. Hubs 3814 and 3818 both contain multiple coating modules 3820, preferably arranged in a cylindrical manner about support shaft 3812. Each coating module 3820 further comprises a series of depositors (best seen in FIG. 40) extending radially from the support shaft 3812. The fibers 3806 continuously pass through a set of coating modules 3820 with each module 3820 synthesizing a predetermined chemistry sequence or compound onto the fiber. The fibers 3806 pass through both hubs 3814 and 3818. Fiber cutting devices 3822 (best seen in FIG. 39) are provided between the platform 3808 and hub 3814 and between hubs 3814 and 3818. The fiber cutting devices 3822 sever the fibers 3806 when a new synthesis sequence or chemical compound is desired. After the fibers 3806 pass through both hubs 3814 and 3818, they enter a deprotection/quality-control module 3824 and thereafter are supplied to the end-product, for example another spool or a fiber array 3826. A motor 3828 moves the end-product to position multiple fibers thereon. It should be appreciated that hubs 3814 and 3818 are preferably cylindrical but may be of any suitable shape.

Corresponding to the circular arrangement of the fiber spools 3804, the coating modules 3820 are arranged to receive fiber 3806, continuously synthesizing one compound onto it, and output the fiber 3806 such that it can be introduced into an adjacent coating module 3820. For each fiber 3806, the modules 3820 are stacked on top of one another to generate the desired synthesis or compound. When a new synthesis sequence for the fibers 3806 is desired, the cutting modules 3822 (FIG. 39) sever each fiber 3806, and the lower hub 3818 is rotated relative to the upper hub 3814. This rotation of the lower hub 3818 causes the fibers 3806 from the upper hub 3814 to enter another module in the lower hub 3818 as the fibers 3806 of cut-length continues to pass through the lower hub 3818. In other words, the motion of fiber 3806 through the system is not interrupted to change to a new synthesis sequence. The fiber may initially be manually fed through the modules, and once the fiber is cut, the fiber from the upper hub may naturally feed into the lower hub after it has rotated. Alternatively, the fiber may be fused with the end of an adjacent fiber located in the lower hub after it has been rotated. The fusing of fiber ends may be accomplished by mechanical, chemical or thermal means.

Figure 39:
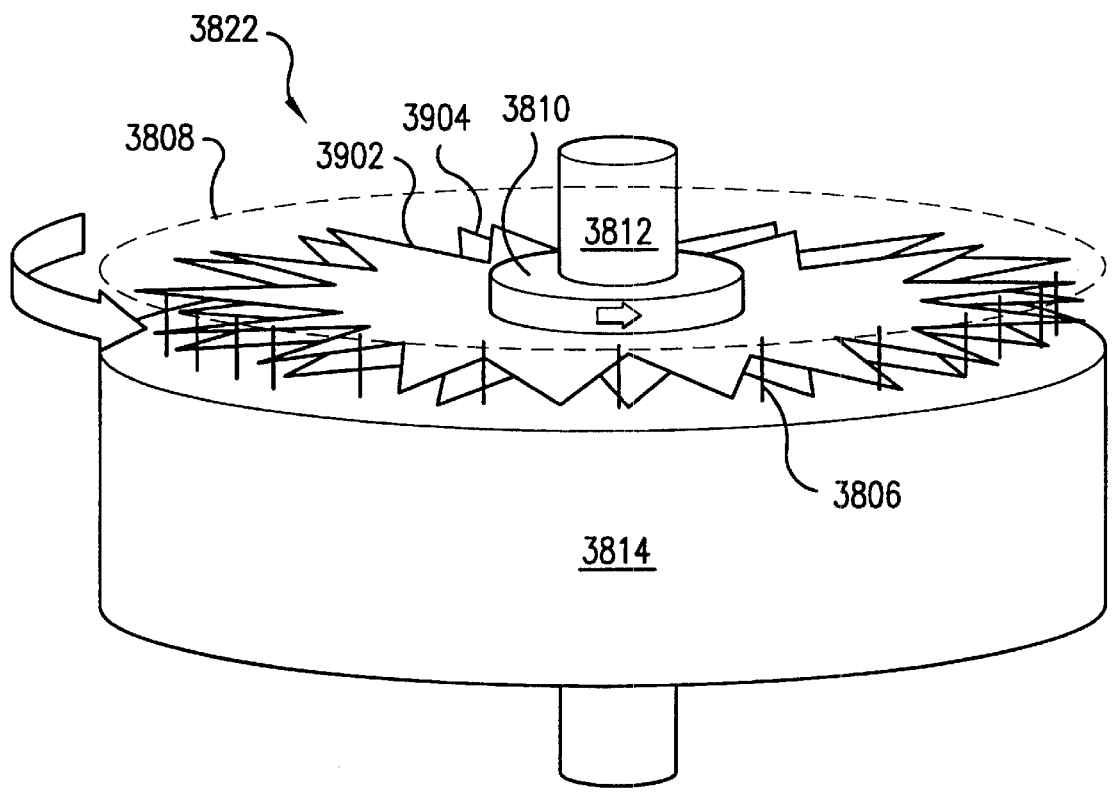
FIG. 39 is an enlarged perspective view of the fiber cutting device illustrated in FIG. 38.

FIG. 39 is an enlarged perspective view of the fiber cutting device 3822 illustrated in FIG. 38. The fiber cutting device 3822 consists of a top 3902 and bottom 3904 circular saw blades in the location between the platform 3808 and the upper hub 3814. The top blade 3902 may be fixed to the motor 3810 that rotates the platform 3808 about the support shaft 3812. The bottom blade 3904 may be fixed to the stationary hub 3814. When the platform 3808 rotates to a new position, the fiber cutting device 3822 cuts all the fibers 3806 simultaneously between the platform 3808 and the upper hub 3814. A similar fiber cutting device 3822 may also be located between hubs 3814 and 3818. The top blade 3902 of the fiber cutting device 3822 may be fixed to the upper hub 3814. The bottom blade 3904 rotates with the lower hub 3818, cutting the fibers 3806 as it rotates.

Figure 40:
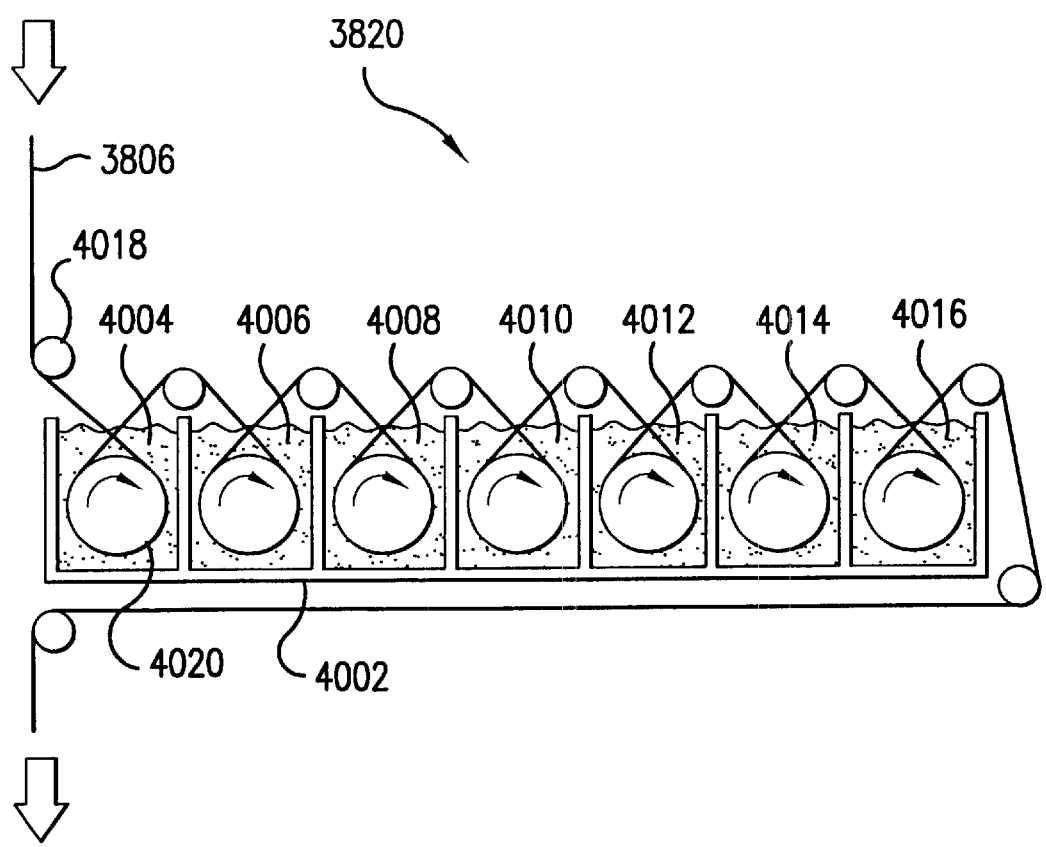
FIG. 40 is a side view of the coating module illustrated in FIG. 38.

FIG. 40 is a side view of the coating module illustrated in FIG. 38. The coating module 3820 preferably consists of multiple containers 4002 containing liquids 4004–4016 through which a fiber 3806 maybe continuously passed. The fiber 3806 is guided through the liquids 4004–4016 by small rollers 4018 and large rollers 4020. The liquids 4004–4016 are of the correct chemical composition and concentration to add a DNA base to the fiber 3806. A preferred arrangement of liquids 4004–4016, listed in order of fiber contact, are: detritylation 4004, activator 4006, phosphoramidite (base) 4008, capping agent A & B 4010, washing solution 4012, oxidizer 4014, and a second washing solution 4016. The fiber 3806 preferably exits the coating module 3820 at the same rate that it enters, and at a composition that allows a subsequent (or the same) module 3820 to chemically add or synthesize another base onto the DNA chain.

Figure 41:
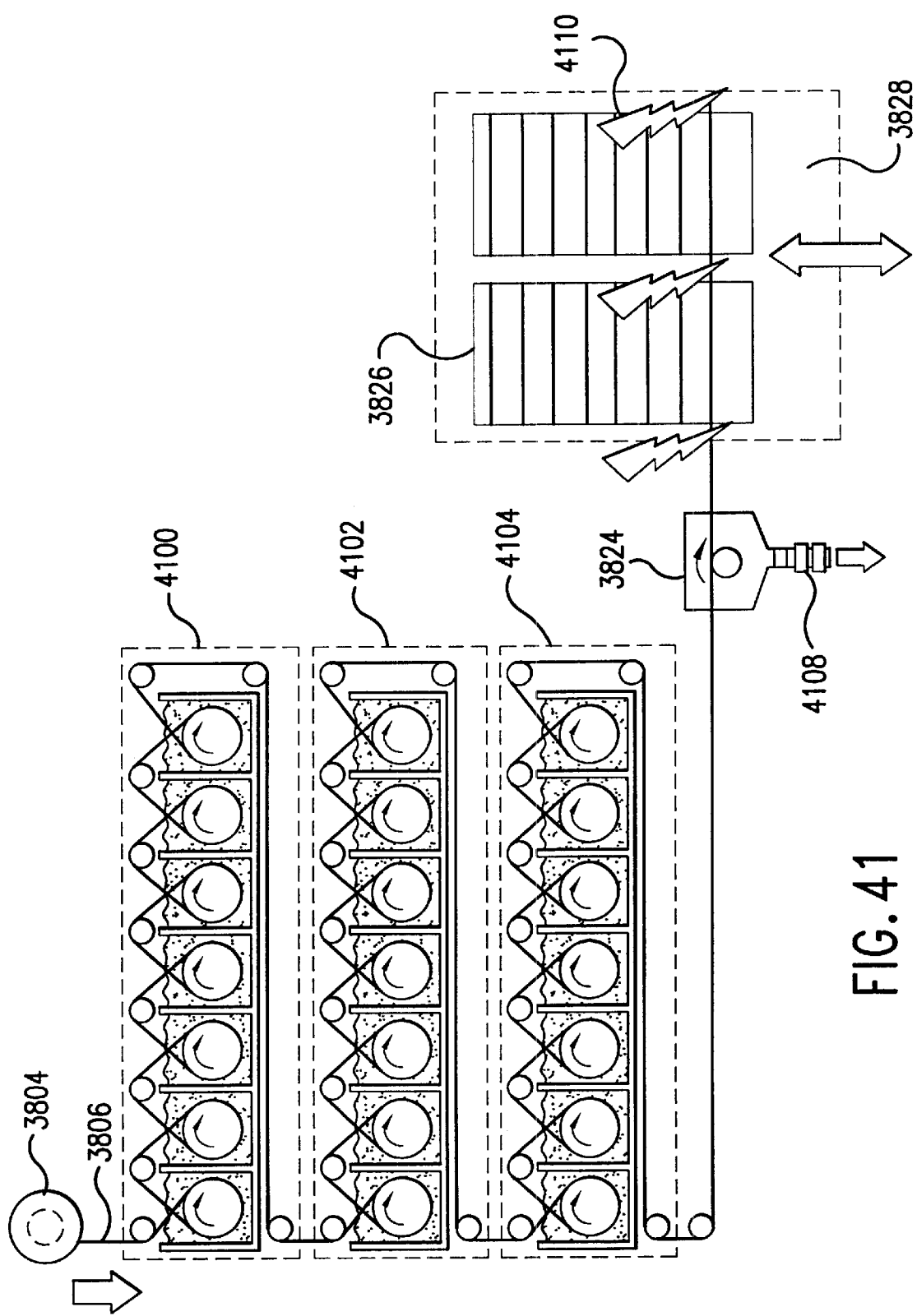
FIG. 41 is a side view of the stacked coating modules illustrated in FIG. 38.

A plurality of modules 3820 can be stacked to add as many DNA bases onto a fiber 3806 as desired. For example, FIG. 41 shows three modules 4100–4104 stacked so as to synthesize three bases onto the fiber 3806. The fiber 3806 is introduced from a spool 3804 that may contain many meters of fiber 3806.

After the bases are synthesized onto the fiber 3806, the fiber 3806 passes through a deprotection module 3824 where protection chemicals are removed. The removal process releases a small percentage of oligos that are tested by quality control sensors 4108. After deprotection, the fiber 3806 is positioned in channels on a plurality of fiber array substrates 3826. A motor 3828 moves the fiber arrays 3826 such that the fibers fill all of the channels. Cutting means 4110 are provided before and between the fiber arrays 3826 to sever the fiber into short segments.

Figure 42:
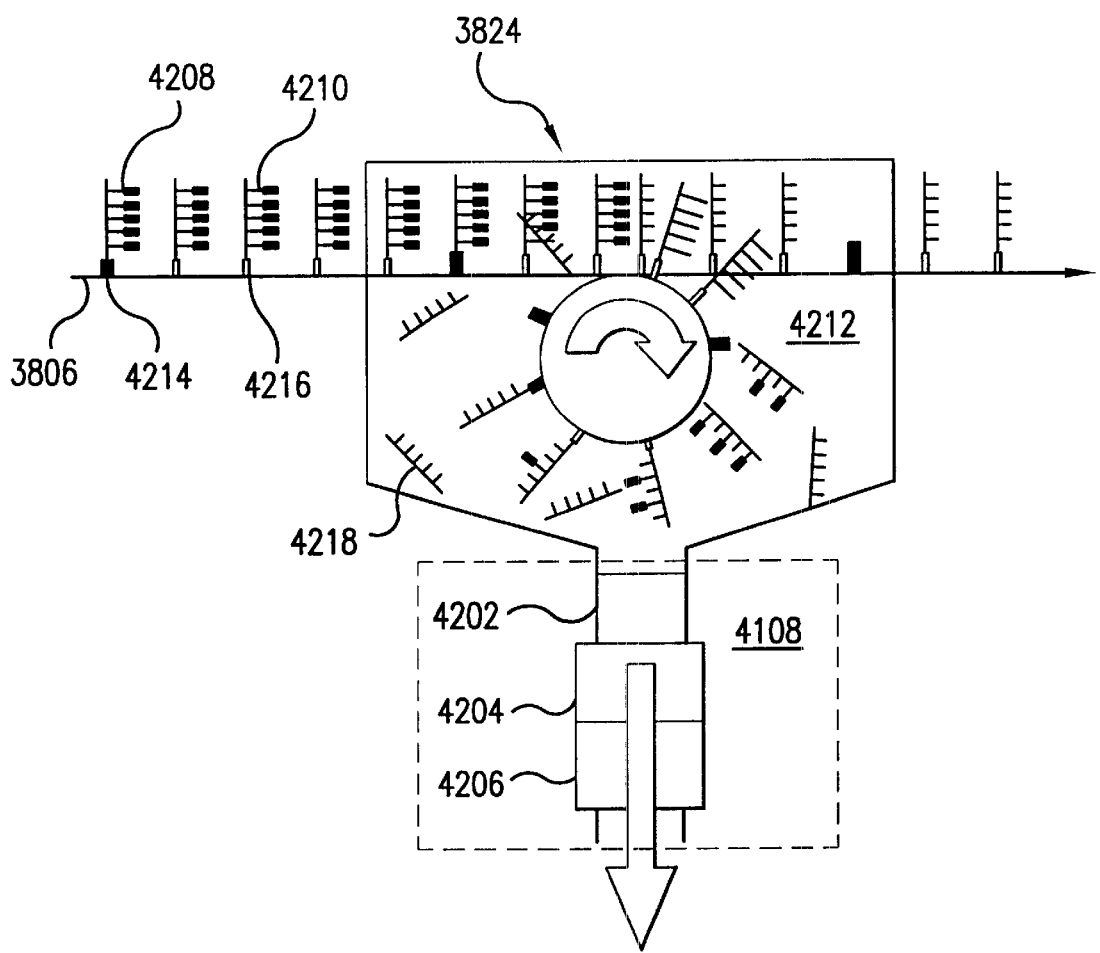
FIG. 42 is an enlarged side view of the deprotection module illustrated in FIG. 38.

FIG. 42 is an enlarged side view of the deprotection module illustrated in FIG. 38. The deprotection module 3824 removes deprotection groups 4208 that were added to an oligo 4210 during synthesis. This removal is implemented by exposing the oligos 4210 to a deprotection composition 4212 such as methyl aminine, to dissolve the deprotection groups 4208. In addition, to removing deprotection groups 4208, some of the oligos 4218 are extracted from the fiber 3806 for quality control purposes. This removal is implemented by applying two different types of linkers to hold the oligos 4210 onto the fibers 3806, namely cleavable 4214 and permanent 4216 linkers. The clevable linkers 4214 dissolve during the deprotection process while the permanent linkers 4216 do not. Most of the linkers are preferably permanent linkers 4216 such that only a small percentage of oligos 4210 are removed from the fiber 3806. The oligos 4218 removed will be passed through various quality control sensors 2008, such as for example a liquid chromatography column 4202 for purity measurement, with an ultraviolet light detector 4204 and a mass spectrometer 4206 for identification.

Figure 43:
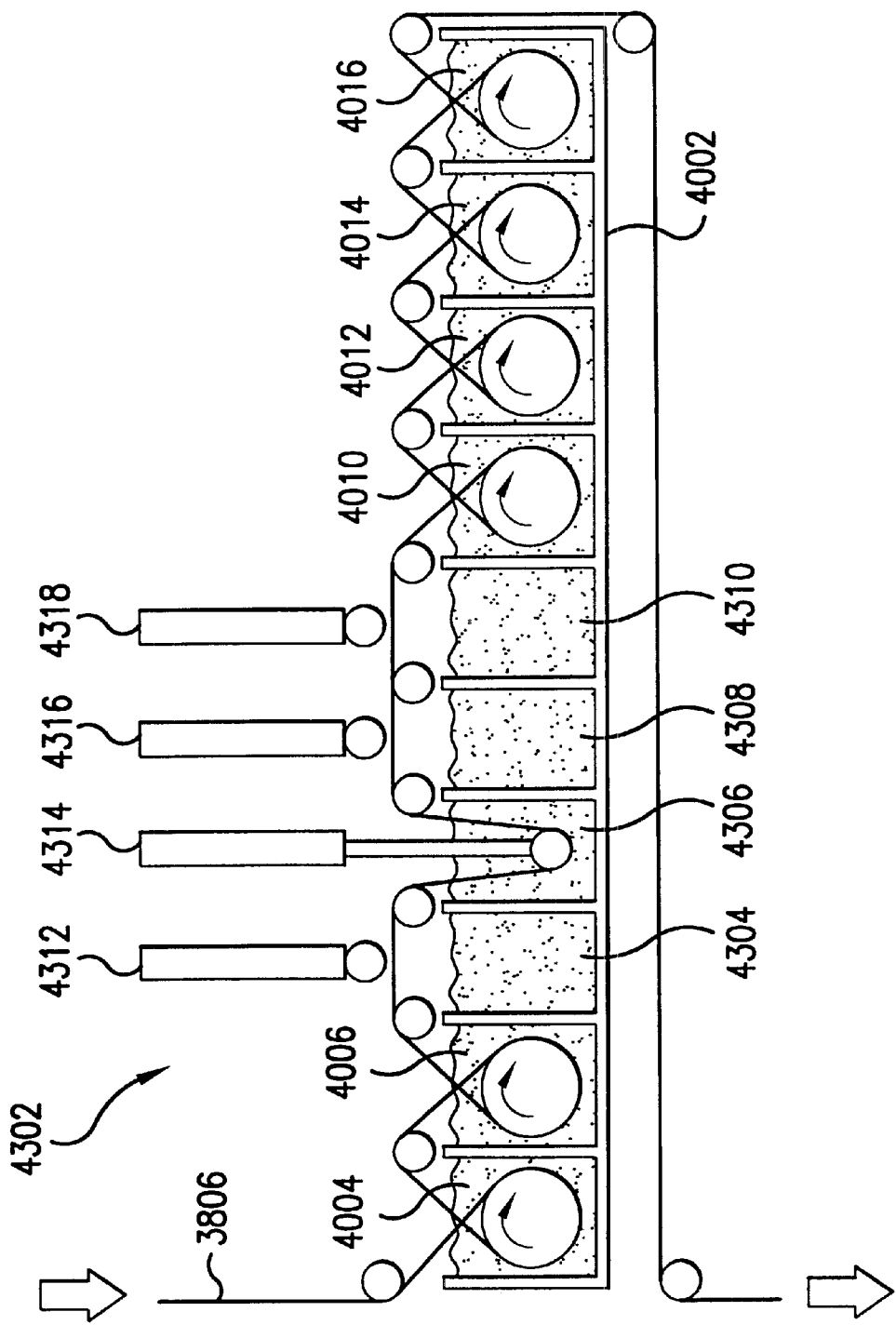
FIG. 43 is an enlarged side view of another embodiment of a coating module according to the present invention.
Figure 44:
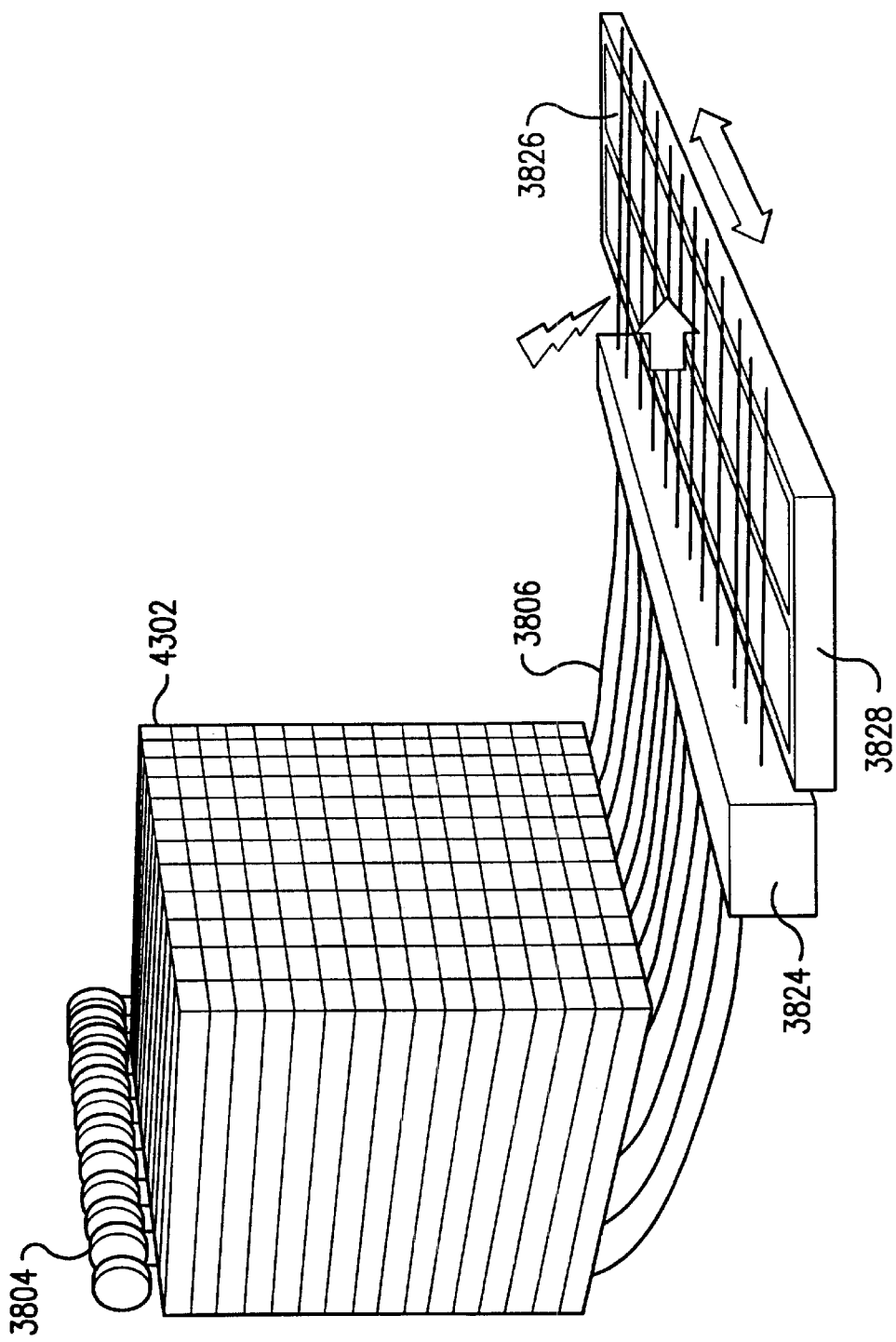
FIG. 44 is a perspective view of the embodiment of the invention illustrated in FIG. 43.

FIG. 43 is an enlarged side view of another embodiment of a coating module 4302. In this configuration, the coating module 4302 is programmed to synthesize one of multiple bases solutions 4304–4310, as selected by an operator, onto the fiber 3806. The base solutions preferably would be oglios A, C, G or T. The module 4302 may still contain the detritylation 4004, activator 4006, capping agents 4010, wash-one 4012, oxidizer 4014, and wash-two 4016- solutions. However, the module 4302 may additionally contain a bath for all bases 4304–4310 instead of only a bath containing one base 4008 as described in relation to the first configuration 3820 (FIG. 40). The selector 3428 (shown in FIG. 34) selects one of multiple actuators 4312–4318 to push the fiber 3806 into contact with one of the multiple base solutions 4304–4310, adding that base in the same process as described above. When a different base is desired, the extended actuator 4312, 4314, 4316 or 4318 is retracted and another actuator 4312, 4314, 4316 or 4318 extends the fiber into contact with a different base solution 4304–4310. This process is repeated as often as desired to synthesize an oglionucleotide onto the fiber 3806. This type of coating module 4302 can be stacked as shown in FIG. 44, with fiber spools 3804, deprotection modules 3824, and motor 3828 to lay the fibers 3806 into a plurality of fiber arrays 3826.

One application for the present invention is DNA synthesis, in particular making every combination of a certain DNA length. For example, every combination of a 9 base long DNA fragment (oligo) would generate 262,144 different oligos (4 to the ninth power). Eight modules per fiber could generate a 9-base oligo if the fibers are loaded into the machine with one base already attached (see FIG. 17). However, to make 262,144 stacks of 8-high modules would be daunting. But, with this device, a relatively small set of modules can be arranged to multiply the number of different combinations generated. For example, 256 fibers can be passed through the upper hub with four-modules per fiber to synthesis every combination of four bases on those fibers (256). If the lower hub is arranged the same way (256 fibers×4 modules), the system would synthesize 256, 9-base oligos simultaneously—a small subset of the 262,144 combinations required. However, when a subset of fibers is made, the fibers can be cut, and the lower hub rotated to make a second subset of fiber combinations. By repeating this process 256 times, 65,536 combinations of a 9-mer will have been synthesized (255×256). Now, the platform is rotated one fiber position and the whole process repeated another three times to synthesize every 9-mer combination of 262,144.

Various embodiments of the invention have been described. The descriptions are intended to be illustrative of the present invention. It will be apparent to one of skill in the art that modifications may be made to the invention as described without departing from the scope of the claims set out below. For example, it is to be understood that although the invention has described various geometries for the support plate and the arrangement of the fibers and channels, other geometries are possible and are contemplated to fall within the scope of the invention. Further, although the invention has been illustrated with particular reference to oligonucleotides and nucleic acid sequencing, any use for contacting at least two chemical species is contemplated to fall within the scope of the invention.

What is claimed is:

1. A method for making a microchip having a plurality of contact points, comprising:
   immobilizing each of a plurality of known chemical species on a separate fiber; and
   placing each of said fibers on a support having a plurality of parallel and fluidly independent channels for receiving an analyte, wherein said plurality of fibers are arranged in parallel on said support and substantially normal to said plurality of channels, thereby forming a matrix of contact positions between a portion of each of said fibers and each of said plurality of channels, such that each of said fibers is contacted by said analyte.

2. The method of claim 1 wherein said plurality of known chemical species are polynucleotide probes.

3. The method of claim 2 wherein said fibers are optical fibers.

4. A method for making a microchip having a plurality of contact points, comprising:
   providing a support having a plurality of substantially parallel and fluidly independent channels configured to receive an analyte therein;
   immobilizing a first chemical species on a first fiber;
   immobilizing a second chemical species on a second fiber; and
   placing said first and second fibers on said support substantially parallel to each other and substantially perpendicular to said channels, thereby forming a matrix of contact positions between portions of each of said first and second fibers and each of said channels.

5. The method of claim 4 wherein said first and second chemical species are polynucleotide probes.

6. The method of claim 4 wherein said first and second fibers are optical fibers.

7. A method for synthesizing a chemical species on a optical fiber comprising the steps of:

determining an order for depositing a plurality of chemical species precursors on a optical fiber;

sequentially transporting said fiber into proximity with each of said plurality of chemical species precursors, in accordance with said order; and sequentially depositing each of said plurality of chemical species precursors on said fiber in said order to synthesize a predetermined chemical species on said fiber.

8. A method according to claim 7, wherein said method further comprises the step of contacting said fiber with a preparatory solution.

9. A method according to claim 7, wherein said method further comprises the step of contacting said fiber with a post depositing solution.

10. A method according to claim 7, wherein said method further comprises synthesizing an oligonucleotide on the fiber.

11. A method according to claim 7, wherein said method further comprises the steps of:

applying a detritylation chemical to the fiber;
   binding a base chemical to the fiber;
   coating the fiber with an activation chemical;
   covering the fiber with a caping agent;
   washing the fiber with a solvent;
   discharging a oxidizer onto the fiber; and
   cleansing the fiber with a solvent.

12. A method according to claim 7, further comprising the step of removing deprotection groups from the fiber.

13. A method according to claim 7, further comprising the step of extracting part of the predetermined chemical species from the fiber.

14. A method according to claim 13, further comprising the step of analyzing said extracted part of said chemical compound.

15. A method according to claim 7, further comprising the step, prior to said determining step, of dispensing a optical fiber from a spool.

16. A method according to claim 7, further comprising the step, prior to said determining step, of arranging the fibers in a fiber array.

17. A method according to claim 7, wherein said transporting step further comprises the steps of:

passing a first optical fiber through a plurality of cylindrical hubs rotatable about a central axis, where each of said hubs comprises at least one bath containing a chemical species precursor, until a first predetermined chemical species is synthesized on said first fiber;

rotating at least one of said hubs; and passing a second optical fiber through said plurality of cylindrical hubs until a second predetermined chemical compound is synthesized on said second fiber.

* * * * *